(12) United States Patent
Foster et al.

(10) Patent No.: US 10,538,746 B2
(45) Date of Patent: Jan. 21, 2020

(54) POLYPEPTIDES AND VARIANTS HAVING IMPROVED ACTIVITY, MATERIALS AND PROCESSES RELATING THERETO

(71) Applicant: INVISTA North American S.á r.l., Wilmington, DE (US)

(72) Inventors: Alexander Brett Foster, Wilton (GB); Adriana Leonora Botes, Rosedale East (GB)

(73) Assignee: INVISTA North America S.à r.l., Wilmington, DE (US)

( * ) Notice: Subject to any disclaimer, the term of this patent is extended or adjusted under 35 U.S.C. 154(b) by 0 days.

(21) Appl. No.: 15/460,414

(22) Filed: Mar. 16, 2017

(65) Prior Publication Data

US 2017/0298325 A1    Oct. 19, 2017

Related U.S. Application Data

(60) Provisional application No. 62/309,689, filed on Mar. 17, 2016.

(51) Int. Cl.
*C12N 9/02* (2006.01)
*C07C 59/147* (2006.01)
*C12P 7/40* (2006.01)

(52) U.S. Cl.
CPC .......... *C12N 9/0008* (2013.01); *C07C 59/147* (2013.01); *C12P 7/40* (2013.01); *C12Y 102/99006* (2013.01)

(58) Field of Classification Search
None
See application file for complete search history.

(56) References Cited

U.S. PATENT DOCUMENTS

| 4,554,101 | A  | 11/1985 | Hopp |
| 7,169,588 | B2 | 1/2007  | Burch et al. |
| 2007/0264688 | A1 | 11/2007 | Venter et al. |
| 2007/0269862 | A1 | 11/2007 | Glass et al. |

FOREIGN PATENT DOCUMENTS

| WO | 2013/152052 A2 | 10/2013 |
| WO | 2014/105797 A2 | 7/2014 |
| WO | 2015/175698 A1 | 11/2015 |
| WO | 2017/161112 A1 | 9/2017 |
| WO | 2017/161112 A8 | 10/2017 |

OTHER PUBLICATIONS

Unipro Accession No. E5XUS9, Mar. 2011.*
Akhtar et al., "Carboxylic Acid Reductase is a Versatile Enzyme for the Conversion of Fatty Acids Into Fuels and Chemical Commodities", Proceedings of the National Academy of Sciences, vol. 110, No. 1, Jan. 2, 2013, pp. 87-92.
Altschul et al., "Gapped BLAST and PSI-BLAST: A New Generation of Protein Database Search Programs", Nucleic Adds Research (NCB NLM NIH), Bethesda Md., NAR, vol. 25, No. 17, Jul. 16, 1997, pp. 3389-3402.
Ausubel et al., "Current Protocols in Molecular Biology", Greene Publishing Associates/Wiley Interscience, New York, Supplement 30, Section 7.7.18, 1987, 1 page.
Ausubel et al., "Computer Manipulation of DNA and Protein Sequences", Current Protocois in Molecular Biology, John Wiley & Sons, Inc., 1995, 23 pages.
Buffle et al., "Source Apportionment of Atmospheric Particles", IUPAC Environmental Analytical Chemistry Series (Lewis Publishers, Inc.), vol. 1, 1992, 74 pages.
Creighton, P., "Chemical Properties of Polypeptides", Proteins, W.H. Freeman and Co., 1984, 19 pages.
Devereaux et al., "A Comprehensive Set of Sequence Analysis Programs for the VAX", Nucleic Acids Research, vol. 12, No. 1, 1984, pp. 387-395.
Ishizuka et al., "Putrescine Oxidase of Micrococcus Rubens : Primaty Structure and *Escherichia Coli*", Journal of General Microbiology, vol. 139, 1993, pp. 425-432.
Kyte et al., "A Simple Method for Displaying the Hydropathic Character of a Protein", Journal of Molecular Biology, vol. 157, No. 1, 1982, pp. 105-132.
Myers et al., "Optimal Alignments in Linear Space", Bioinformatics, Computer Applications in the Biosciences, vol. 4, No. 1, 1988, pp. 11-17.
Pearson et al., "Improved Tools for Biolog ofical Sequence Comparison", Proceedings of the National Academy of Sciences, Biochemistry, vol. 85, Apr. 1988, pp. 2444-2448.
Sambrook et al., "Molecular Cloning: A Laboratory Manual", Cold Spring Harbor Laboratory Press, 3rd Edition, vol. 1, 2 and 3, 2001, 3 pages.
Sambrook et al., "Molecular Cloning: A Laboratory Manual", Cold Spring Harbor Laboratory Press, 4th Edition, vol. 1, 2012, 34 pages.
Stuiver et al., "Discussion Reporting of 14 C Data", Radiocarbon, vol. 19, No. 3, 1977, pp. 355-363.
"Segniliparus Rotundus DSM 44985 Thioester Reductase Domain Protein", EBI Accession No. UNIPROT: D6ZDT1, retrieved from <https://www.ebi.ac.uk/ena/data/view/ADG99338&display=text>, on Dec. 6, 2017, 3 pages.
"Segniliparus Rugosus ATCC BAA-974 Thioester Reductase Domain-Containing Protein", EBI Accession No. UNIPROT: E5XUS9, retrieved from <https://www.ebi.ac.uk/ena/data/view/EFV11917&display=text>, on Dec. 6, 2017, 3 pages.
Kim, Jong-Seok et al., "Differential Immune Responses to Segniliparus rotundus and Segniliparus rugosus Infection and Analysis of Their Comparative Virulence Profiles", PLOS One, vol. 8, Issue 3, Mar. 2013, pp. 1-19.
International Search Report and Written Opinion received for PCT Patent Application No. PCT/US2017/022697, dated Sep. 6, 2017, 20 pages.

* cited by examiner

*Primary Examiner* — Richard G Hutson
(74) *Attorney, Agent, or Firm* — Finnegan, Henderson, Farabow, Garrett & Dunner LLP

(57) ABSTRACT

The disclosure relates to polypeptides having carboxylic acid reductase (CAR) activity, including enzymes that catalyse the irreversible reduction of carboxylic acids, such as pimelic acid and adipic acid, to their respective semialdehydes. The enzymes have been engineered to have higher activity over a corresponding wild type enzyme. Provided herein are novel polypeptides and uses thereof related to the same.

4 Claims, 5 Drawing Sheets
(2 of 5 Drawing Sheet(s) Filed in Color)
Specification includes a Sequence Listing.

FIG. 3A

```
SrugCAR      MGDGEERAKRFFQRIGELSATDPQFAAAAPDPAVVEAVSDPSLSFTRYLDTLMRGYAERP
SrotCAR      MGSGADRAKLFFQKIEELTAADPQFAAAVPDQEVVAAVSDPTLSFTRYLDTLMRGYADRP SrugCAR      ALAHRVGAGYETISYGELWARVGAIAAAWQADGLAPGDFVATVGFTSPDYVAVDLAAARS
SrotCAR      ALAHRVGDYATISYGELWSRVGAIAAAWSADGLEPGDFVATIGFTSPDYTALDLAATRS SrugCAR      GLVSVPLQAGASLAQLVGILEETEPKVLAASASSLEGAVACALAAPSVQRLVVFDLRGPD
SrotCAR      GLVSVPLQAGASVAQLSAILEETAPKVFAASAESLEGAVDCVLRTPSVQRLVIFDLR---

SrugCAR      ASESAADERRGALADAEEQLA------RAGRAVVVETLADLAARGEALPEAPLFEPAEGE
SrotCAR      ----DDSPEHRAALAAAKAKLAQPQNPEQARGPVAVETLDELVARGAALPEPPVFEPAEGE SrugCAR      DPLALLIYTSGSTGAPKGAMYSQRLVSQLWGRTPVVPGMPNISLHYMPLSHSYGRAVLAG
SrotCAR      DPLALLIYTSGSTGTPKGAMYSQRLVSRFWPRTPVVAQLPSISLHYMPLSHSYGRAVLCG SrugCAR      ALSAGGTAHFTANSDLSTLFEDIALARPTFLALVPRVCEMLFQESQRGQDVAELRERVLG
SrotCAR      TLAAGGTAHFTAHSDLSTLFEDIALARPTFLALVPRVCEMLLHESRRARDLAELRERVLG S.rugCAR69                   S        E
SrugCAR      GRLLVAVCGSAPLS EMRAFMEEVL FPLLDGYGSTEALGVMRNGIIQRPPVIDYKLVDV
SrotCAR      ERLLVAVCGSAPLAPETRAFMEELLGFPLLDGYGSTEALSLMRDGVIQRPPVIDYKLVDV SrugCAR      PELGYRTTDKPYPRGELCIRSTSLISGYYKRPEITAEVFDAQGYYKTGDVMAEIAPDHLV
SrotCAR      PELGYFTTDKPHPRGELLIRSESLVSGYYKRPELTAEMFDEQGYYKTGDVMAEIAPDRLV SrugCAR      YVDRSKNVLKLSQGEFVAVAKLEAAYGTSPYVKQIFVYGNSERSFLLAVVVPNAEVLGAR
SrotCAR      YVDRSKNVLKLSQGEFVAVAKLEAAFGASPYVKQIFVYGNSERSFLLAVVVPNAELVGRL SrugCAR      DQ----EEAKPLIAASLQKIAKEAGLQSYEVPRDFLIETEPFTTQNGLLSEVGKLLRPKL
SrotCAR      DTVQALAEVKPLIADSLAAIAKESGLQSYEVPRDFIVETEPFTTGNGLLSEVGKLLRPKL S.rugCAR69                                L
SrugCAR      KARYGEALEARYDEIAHGQADELRALRD AGQRPVVETVVRAAVAISGSEGAEVGPEANF
SrotCAR      KERYGERLEALYDQIAQGQADELRALREQAGERPVIDTVRKAAAAVVGSSGADFRPDANF S.rugCAR69                                              R
SrugCAR      ADLGGDSLSALSLANLLHDVFEVEVPVRIIIGPTASLAGIA HIE---AERAGASAPTAA
SrotCAR      ADLGGDSLSALGFANLLQDVFGVETPVRIIIGPTASLAGIAEHIERALGGRPGEAAPNSA SrugCAR      SVHGAGATRIRASELTLEKFLPEDLLAAAKGLP-AADQVRTVLLTGANGWLGRFLALEQL
SrotCAR      SVHGAGAEVIRASDLTLDKFLDAQALEAAQSLPRPTGSHRTVLLTGANGWLGRFLALEQL SrugCAR      ERLARSGQDGGKLICLVRGKDAAAARRRIEETLGTDPALAARFAELAEGRLEVVPGDVGE
SrotCAR      QRLEAT----GGKLICLVRGKDAASARARVEEALGTDPALAARFAELAADRLEVVPGDVGE SrugCAR      PKFGLDDAAWDRLAEEVDVIVHPAALVNHVLPYHQLFGPNVVGTAEIIRLAITAKRKPVT
SrotCAR      PKFGLDDRTWDRLAGEVDAVVHSGALVNHVLPYHQLFGSNVVGVAEIIRFAVASKLKPVA
```

FIG. 3B

```
SrugCAR    YLSTVAVAAGVEPSSFEEDGDIRAVVPERPLGDGYANGYGNSKWAGEVLLREAHELVGLP
SrotCAR    YLSTVAVAAGADPAAFDEDGDIREVVPQRPVDDSYANGYGNSKWAGEVLLREAHERTGLP SrugCAR    VAVFRSDMILAHTRYTGQLNVPDQFTRLVLSLLATGIAPKSFYQQGAAGERQRAHYDGIP
SrotCAR    VRVFRSDMILAHRQHTGQLNATDQFTRLILSLLATGLAPKSFYQLDPQGRRQRAHYDGIP SrugCAR    VDFTAEAITTLGAEPSWFDGGAGFRSFDVFNPHHDGVGLDEFVDWLIEAGHPISRIDDHK
SrotCAR    VDFTAEAIVALAAE-----GNNGHRSYNVFNPHHDGVGLDEFVDWLIEAGHPITRIEDHA SrugCAR    EWFARFETAVRGLPEAQRQHSLLPLLRAYSFPHPPVDGSVYPTGKFQGAVKAAQVGSDHD
SrotCAR    TWFARFTTALRALPEKQRQLSLLPLAQVYSFPHPAVDGSPFRNAVFRADVQRARIGKDHD SrugCAR    VPHLGKALIVKYADDLKALGLL
SrotCAR    IPHLTRELILKYAADLAALGLL
```

FIG. 4

| Variant | Pimelic Acid [Z-factors] | [slope/min] | Adipic acid [Z-factors] | [slope/min] |
|---|---|---|---|---|
| T371F | | | 1.44 | -0.057 |
| S284I | | | | -0.058 |
| H237I | | | 1.44 | -0.057 |
| M334V | 1.61 | -0.067 | 1.64 | -0.059 |
| P592G | | | 1.41 | -0.057 |
| K495V | 1.31 | -0.066 | 1.33 | -0.056 |
| K495V | 1.15 | -0.063 | 1.30 | -0.056 |
| G579E | 1.15 | -0.063 | 0.99 | -0.053 |
| L379V | 1.11 | -0.063 | 1.03 | -0.053 |
| V491L | 1.24 | -0.064 | 0.89 | -0.052 |
| D647S | 1.08 | -0.062 | 1.01 | -0.053 |
| P592G | 1.02 | -0.061 | 1.06 | -0.053 |
| T780S | 1.22 | -0.064 | 0.85 | -0.051 |
| D647G | 0.96 | -0.061 | 1.03 | -0.053 |
| K495V | 0.97 | -0.061 | 0.98 | -0.052 |
| | 0.86 | -0.060 | 1.02 | -0.053 |
| D647S | 1.01 | -0.061 | 0.89 | -0.051 |
| not OK | 1.15 | -0.063 | 0.73 | -0.050 |
| | 1.00 | -0.061 | 0.84 | -0.051 |
| | 0.93 | -0.060 | 0.86 | -0.051 |
| L383V | 0.92 | -0.060 | 0.86 | -0.051 |
| L383T | 0.81 | -0.059 | 0.78 | -0.050 |
| D647S | 0.77 | -0.058 | 0.78 | -0.050 |
| | 0.67 | -0.057 | 0.88 | -0.051 |
| | 0.85 | -0.059 | 0.64 | -0.049 |
| M334G | 0.85 | -0.059 | 0.64 | -0.049 |
| N481D | 1.64 | -0.067 | -0.08 | -0.042 |
| | 0.79 | -0.058 | 0.67 | -0.049 |
| P592A | 0.81 | -0.059 | 0.61 | -0.049 |
| L590V | 1.02 | -0.061 | 0.35 | -0.046 |
| V491L | 0.83 | -0.059 | 0.49 | -0.048 |
| L893V | 0.33 | -0.053 | 0.97 | -0.052 |
| H337D | 0.85 | -0.060 | 0.41 | -0.047 |
| L338F | 0.59 | -0.056 | 0.55 | -0.048 |
| G386A | 0.41 | -0.054 | 0.71 | -0.050 |
| R591G | 1.00 | -0.061 | 0.11 | -0.044 |
| F453A | 0.53 | -0.056 | 0.32 | -0.046 |
| D607S | 0.37 | -0.054 | 0.47 | -0.047 |
| V491L | 0.49 | -0.055 | 0.24 | -0.045 |
| V474R | 0.32 | -0.053 | 0.35 | -0.046 |
| A703H | 0.44 | -0.053 | 0.21 | -0.045 |
| | 0.28 | -0.053 | 0.38 | -0.046 |
| T780N | 0.29 | -0.053 | 0.25 | -0.045 |
| A902I | 0.21 | -0.052 | 0.25 | -0.045 |
| E566G | 0.15 | -0.052 | 0.20 | -0.045 |
| | 0.14 | -0.051 | 0.19 | -0.045 |
| | 0.09 | -0.050 | 0.18 | -0.044 |
| L1086A | 0.01 | -0.050 | 0.16 | -0.044 |
| G579V | 0.15 | -0.051 | 0.01 | -0.043 |
| | 0.10 | -0.051 | 0.01 | -0.043 |
| P711D | 0.18 | -0.052 | -0.12 | -0.041 |
| V476L | 0.02 | -0.050 | 0.05 | -0.043 |
| G781D | -0.07 | -0.049 | -0.09 | -0.042 |
| | -0.11 | -0.048 | -0.09 | -0.042 |
| R780L | 0.00 | -0.049 | -0.21 | -0.040 |
| E574D | -0.16 | -0.048 | -0.13 | -0.041 |
| A737N | -0.15 | -0.048 | -0.26 | -0.040 |
| | -0.22 | -0.047 | -0.31 | -0.039 |
| A494V | 0.36 | -0.054 | -0.92 | -0.033 |
| | -0.25 | -0.047 | -0.36 | -0.039 |
| V474G | -0.67 | -0.042 | -0.55 | -0.037 |
| K635W | -1.13 | -0.038 | -1.19 | -0.031 |
| L602G | -2.65 | -0.018 | -2.66 | -0.016 |

SEQUENCE LISTING

<160> NUMBER OF SEQ ID NOS: 12

<210> SEQ ID NO 1
<211> LENGTH: 1148
<212> TYPE: PRT
<213> ORGANISM: Segniliparus rugosus

<400> SEQUENCE: 1

```
Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
        35                  40                  45

Leu Asp Thr Leu Met Arg Gly Tyr Ala Glu Arg Pro Ala Leu His
        50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Ala Trp Gln Ala Asp Gly Leu Ala Pro
                85                  90                  95

Gly Asp Phe Val Ala Thr Val Gly Phe Thr Ser Pro Asp Tyr Val Ala
                100                 105                 110

Val Asp Leu Ala Ala Ala Arg Ser Gly Leu Val Ser Val Pro Leu Gln
            115                 120                 125
```

```
Ala Gly Ala Ser Leu Ala Gln Leu Val Gly Ile Leu Glu Glu Thr Glu
        130                 135                 140

Pro Lys Val Leu Ala Ala Ser Ala Ser Leu Glu Gly Ala Val Ala
145                 150                 155                 160

Cys Ala Leu Ala Ala Pro Ser Val Gln Arg Leu Val Val Phe Asp Leu
                    165                 170                 175

Arg Gly Pro Asp Ala Ser Glu Ser Ala Ala Asp Glu Arg Arg Gly Ala
                180                 185                 190

Leu Ala Asp Ala Glu Glu Gln Leu Ala Arg Ala Gly Arg Ala Val Val
            195                 200                 205

Val Glu Thr Leu Ala Asp Leu Ala Ala Arg Gly Glu Ala Leu Pro Glu
        210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                    245                 250                 255

Gln Arg Leu Val Ser Gln Leu Trp Gly Arg Thr Pro Val Val Pro Gly
                260                 265                 270

Met Pro Asn Ile Ser Leu His Tyr Met Pro Leu Ser His Ser Tyr Gly
            275                 280                 285

Arg Ala Val Leu Ala Gly Ala Leu Ser Ala Gly Gly Thr Ala His Phe
        290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                    325                 330                 335

Gln Glu Ser Gln Arg Gly Gln Asp Val Ala Glu Leu Arg Glu Arg Val
                340                 345                 350

Leu Gly Gly Arg Leu Leu Val Ala Val Cys Gly Ser Ala Pro Leu Ser
            355                 360                 365

Pro Glu Met Arg Ala Phe Met Glu Glu Val Leu Gly Phe Pro Leu Leu
        370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                    405                 410                 415

Leu Gly Tyr Arg Thr Thr Asp Lys Pro Tyr Pro Arg Gly Glu Leu Cys
                420                 425                 430

Ile Arg Ser Thr Ser Leu Ile Ser Gly Tyr Tyr Lys Arg Pro Glu Ile
            435                 440                 445

Thr Ala Glu Val Phe Asp Ala Gln Gly Tyr Tyr Lys Thr Gly Asp Val
        450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                    485                 490                 495

Glu Ala Ala Tyr Gly Thr Ser Pro Tyr Val Lys Gln Ile Phe Val Tyr
                500                 505                 510

Gly Asn Ser Glu Arg Ser Phe Leu Leu Ala Val Val Val Pro Asn Ala
            515                 520                 525

Glu Val Leu Gly Ala Arg Asp Gln Gly Glu Ala Lys Pro Leu Ile Ala
        530                 535                 540

Ala Ser Leu Gln Lys Ile Ala Lys Glu Ala Gly Leu Gln Ser Tyr Glu
```

```
            545                 550                 555                 560
Val Pro Arg Asp Phe Leu Ile Glu Thr Glu Pro Phe Thr Thr Gln Asn
                    565                 570                 575

Gly Leu Leu Ser Glu Val Gly Lys Leu Leu Arg Pro Lys Leu Lys Ala
                    580                 585                 590

Arg Tyr Gly Glu Ala Leu Glu Ala Arg Tyr Asp Glu Ile Ala His Gly
                    595                 600                 605

Gln Ala Asp Glu Leu Arg Ala Leu Arg Asp Gly Ala Gly Gln Arg Pro
                    610                 615                 620

Val Val Glu Thr Val Val Arg Ala Ala Val Ala Ile Ser Gly Ser Glu
625                 630                 635                 640

Gly Ala Glu Val Gly Pro Glu Ala Asn Phe Ala Asp Leu Gly Gly Asp
                    645                 650                 655

Ser Leu Ser Ala Leu Ser Leu Ala Asn Leu Leu His Asp Val Phe Glu
                    660                 665                 670

Val Glu Val Pro Val Arg Ile Ile Ile Gly Pro Thr Ala Ser Leu Ala
                    675                 680                 685

Gly Ile Ala Lys His Ile Glu Ala Glu Arg Ala Gly Ala Ser Ala Pro
                    690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Leu Ala Ala Ala
                    725                 730                 735

Lys Gly Leu Pro Ala Ala Asp Gln Val Arg Thr Val Leu Leu Thr Gly
                    740                 745                 750

Ala Asn Gly Trp Leu Gly Arg Phe Leu Ala Leu Glu Gln Leu Glu Arg
                    755                 760                 765

Leu Ala Arg Ser Gly Gln Asp Gly Gly Lys Leu Ile Cys Leu Val Arg
                    770                 775                 780

Gly Lys Asp Ala Ala Ala Arg Arg Ile Glu Glu Thr Leu Gly
785                 790                 795                 800

Thr Asp Pro Ala Leu Ala Ala Arg Phe Ala Glu Leu Ala Glu Gly Arg
                    805                 810                 815

Leu Glu Val Val Pro Gly Asp Val Gly Glu Pro Lys Phe Gly Leu Asp
                    820                 825                 830

Asp Ala Ala Trp Asp Arg Leu Ala Glu Glu Val Asp Val Ile Val His
                    835                 840                 845

Pro Ala Ala Leu Val Asn His Val Leu Pro Tyr His Gln Leu Phe Gly
                    850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
                    885                 890                 895

Val Glu Pro Ser Ser Phe Glu Glu Asp Gly Asp Ile Arg Ala Val Val
                    900                 905                 910

Pro Glu Arg Pro Leu Gly Asp Gly Tyr Ala Asn Gly Tyr Gly Asn Ser
                    915                 920                 925

Lys Trp Ala Gly Glu Val Leu Leu Arg Glu Ala His Glu Leu Val Gly
                    930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
                    965                 970                 975
```

```
Ser Leu Leu Ala Thr Gly Ile Ala Pro Lys Ser Phe Tyr Gln Gln Gly
            980                 985                 990

Ala Ala Gly Glu Arg Gln Arg Ala  His Tyr Asp Gly Ile  Pro Val Asp
        995                 1000                1005

Phe Thr  Ala Glu Ala Ile Thr  Thr Leu Gly Ala Glu  Pro Ser Trp
    1010                 1015                1020

Phe Asp  Gly Gly Ala Gly Phe  Arg Ser Phe Asp Val  Phe Asn Pro
    1025                 1030                1035

His His  Asp Gly Val Gly Leu  Asp Glu Phe Val Asp  Trp Leu Ile
    1040                 1045                1050

Glu Ala  Gly His Pro Ile Ser  Arg Ile Asp Asp His  Lys Glu Trp
    1055                 1060                1065

Phe Ala  Arg Phe Glu Thr Ala  Val Arg Gly Leu Pro  Glu Ala Gln
    1070                 1075                1080

Arg Gln  His Ser Leu Leu Pro  Leu Leu Arg Ala Tyr  Ser Phe Pro
    1085                 1090                1095

His Pro  Pro Val Asp Gly Ser  Val Tyr Pro Thr Gly  Lys Phe Gln
    1100                 1105                1110

Gly Ala  Val Lys Ala Ala Gln  Val Gly Ser Asp His  Asp Val Pro
    1115                 1120                1125

His Leu  Gly Lys Ala Leu Ile  Val Lys Tyr Ala Asp  Asp Leu Lys
    1130                 1135                1140

Ala Leu  Gly Leu Leu
    1145

<210> SEQ ID NO 2
<211> LENGTH: 1148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gly Ser Gly Ala Asp Arg Ala Lys Leu Phe Phe Gln Lys Ile Glu
1               5                   10                  15

Glu Leu Thr Ala Ala Asp Pro Gln Phe Ala Ala Val Pro Asp Gln
            20                  25                  30

Glu Val Val Ala Ala Val Ser Asp Pro Thr Leu Ser Phe Thr Arg Tyr
            35                  40                  45

Leu Asp Thr Leu Met Arg Gly Tyr Ala Asp Arg Pro Ala Leu Ala His
    50                  55                  60

Arg Val Gly Asp Gly Tyr Ala Thr Ile Ser Tyr Gly Glu Leu Trp Ser
65                  70                  75                  80

Arg Val Gly Ala Ile Ala Ala Trp Ser Ala Asp Gly Leu Glu Pro
                85                  90                  95

Gly Asp Phe Val Ala Thr Ile Gly Phe Thr Ser Pro Asp Tyr Thr Ala
                100                 105                 110

Leu Asp Leu Ala Ala Thr Arg Ser Gly Leu Val Ser Val Pro Leu Gln
        115                 120                 125

Ala Gly Ala Ser Val Ala Gln Leu Ser Ala Ile Leu Glu Glu Thr Ala
        130                 135                 140

Pro Lys Val Phe Ala Ala Ser Ala Glu Ser Leu Glu Gly Ala Val Asp
145                 150                 155                 160

Cys Val Leu Arg Thr Pro Ser Val Gln Arg Leu Val Ile Phe Asp Leu
```

```
            165                 170                 175
Arg Asp Asp Ser Pro Glu His Arg Ala Ala Leu Ala Ala Ala Lys Ala
                180                 185                 190

Lys Leu Ala Gln Pro Gln Asn Pro Glu Gln Ala Arg Gly Pro Val Ala
            195                 200                 205

Val Glu Thr Leu Asp Glu Leu Val Ala Arg Gly Ala Ala Leu Pro Glu
        210                 215                 220

Pro Pro Val Phe Glu Pro Ala Glu Gly Glu Asp Pro Leu Ala Leu Leu
225                 230                 235                 240

Ile Tyr Thr Ser Gly Ser Thr Gly Thr Pro Lys Gly Ala Met Tyr Ser
                245                 250                 255

Gln Arg Leu Val Ser Arg Phe Trp Pro Arg Thr Pro Val Val Ala Gln
            260                 265                 270

Leu Pro Ser Ile Ser Leu His Tyr Met Pro Leu Ser His Ser Tyr Gly
        275                 280                 285

Arg Ala Val Leu Cys Gly Thr Leu Ala Ala Gly Gly Thr Ala His Phe
        290                 295                 300

Thr Ala His Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Leu
                325                 330                 335

His Glu Ser Arg Arg Ala Arg Asp Leu Ala Glu Leu Arg Glu Arg Val
            340                 345                 350

Leu Gly Glu Arg Leu Leu Val Ala Val Cys Gly Ser Ala Pro Leu Ala
        355                 360                 365

Pro Glu Thr Arg Ala Phe Met Glu Glu Leu Leu Gly Phe Pro Leu Leu
    370                 375                 380

Asp Gly Tyr Gly Ser Thr Glu Ala Leu Ser Leu Met Arg Asp Gly Val
385                 390                 395                 400

Ile Gln Arg Pro Pro Val Ile Asp Tyr Lys Leu Val Asp Val Pro Glu
                405                 410                 415

Leu Gly Tyr Phe Thr Thr Asp Lys Pro His Pro Arg Gly Glu Leu Leu
            420                 425                 430

Ile Arg Ser Glu Ser Leu Val Ser Gly Tyr Tyr Lys Arg Pro Glu Leu
        435                 440                 445

Thr Ala Glu Met Phe Asp Glu Gln Gly Tyr Tyr Lys Thr Gly Asp Val
    450                 455                 460

Met Ala Glu Ile Ala Pro Asp Arg Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Phe Gly Ala Ser Pro Tyr Val Lys Gln Ile Phe Val Tyr
            500                 505                 510

Gly Asn Ser Glu Arg Ser Phe Leu Leu Ala Val Val Pro Asn Ala
        515                 520                 525

Glu Leu Val Gly Arg Leu Asp Thr Val Gln Ala Leu Ala Glu Val Lys
    530                 535                 540

Pro Leu Ile Ala Asp Ser Leu Ala Ala Ile Ala Lys Glu Ser Gly Leu
545                 550                 555                 560

Gln Ser Tyr Glu Val Pro Arg Asp Phe Ile Val Glu Thr Glu Pro Phe
                565                 570                 575

Thr Thr Gly Asn Gly Leu Leu Ser Glu Val Gly Lys Leu Leu Arg Pro
            580                 585                 590
```

```
Lys Leu Lys Glu Arg Tyr Gly Glu Arg Leu Glu Ala Leu Tyr Asp Gln
            595                 600                 605

Ile Ala Gln Gly Gln Ala Asp Glu Leu Arg Ala Leu Arg Glu Gln Ala
            610                 615                 620

Gly Glu Arg Pro Val Ile Asp Thr Val Arg Lys Ala Ala Ala Val
625                 630                 635                 640

Val Gly Ser Ser Gly Ala Asp Phe Arg Pro Asp Ala Asn Phe Ala Asp
                    645                 650                 655

Leu Gly Gly Asp Ser Leu Ser Ala Leu Gly Phe Ala Asn Leu Leu Gln
                660                 665                 670

Asp Val Phe Gly Val Glu Thr Pro Val Arg Ile Ile Gly Pro Thr
            675                 680                 685

Ala Ser Leu Ala Gly Ile Ala Glu His Ile Glu Arg Ala Leu Gly Gly
    690                 695                 700

Arg Pro Gly Glu Ala Ala Pro Asn Ser Ala Ser Val His Gly Ala Gly
705                 710                 715                 720

Ala Glu Val Ile Arg Ala Ser Asp Leu Thr Leu Asp Lys Phe Leu Asp
                    725                 730                 735

Ala Gln Ala Leu Glu Ala Ala Gln Ser Leu Pro Arg Pro Thr Gly Ser
                740                 745                 750

His Arg Thr Val Leu Leu Thr Gly Ala Asn Gly Trp Leu Gly Arg Phe
            755                 760                 765

Leu Ala Leu Glu Gln Leu Gln Arg Leu Glu Ala Thr Gly Gly Lys Leu
    770                 775                 780

Ile Cys Leu Val Arg Gly Lys Asp Ala Ala Ser Ala Arg Ala Arg Val
785                 790                 795                 800

Glu Glu Ala Leu Gly Thr Asp Pro Ala Leu Ala Ala Arg Phe Ala Glu
                    805                 810                 815

Leu Ala Ala Asp Arg Leu Glu Val Val Pro Gly Asp Val Gly Glu Pro
                820                 825                 830

Lys Phe Gly Leu Asp Asp Arg Thr Trp Asp Arg Leu Ala Gly Glu Val
            835                 840                 845

Asp Ala Val Val His Ser Gly Ala Leu Val Asn His Val Leu Pro Tyr
    850                 855                 860

His Gln Leu Phe Gly Ser Asn Val Val Gly Val Ala Glu Ile Ile Arg
865                 870                 875                 880

Phe Ala Val Ala Ser Lys Leu Lys Pro Val Ala Tyr Leu Ser Thr Val
                    885                 890                 895

Ala Val Ala Ala Gly Ala Asp Pro Ala Ala Phe Asp Glu Asp Gly Asp
                900                 905                 910

Ile Arg Glu Val Val Pro Gln Arg Pro Val Asp Asp Ser Tyr Ala Asn
            915                 920                 925

Gly Tyr Gly Asn Ser Lys Trp Ala Gly Glu Val Leu Leu Arg Glu Ala
    930                 935                 940

His Glu Arg Thr Gly Leu Pro Val Arg Val Phe Arg Ser Asp Met Ile
945                 950                 955                 960

Leu Ala His Arg Gln His Thr Gly Gln Leu Asn Ala Thr Asp Gln Phe
                    965                 970                 975

Thr Arg Leu Ile Leu Ser Leu Leu Ala Thr Gly Leu Ala Pro Lys Ser
                980                 985                 990

Phe Tyr Gln Leu Asp Pro Gln Gly Arg Arg Gln Arg Ala His Tyr Asp
            995                 1000                1005
```

Gly Ile Pro Val Asp Phe Thr Ala Glu Ala Ile Val Ala Leu Ala
1010                1015                1020

Ala Glu Gly Asn Asn Gly His Arg Ser Tyr Asn Val Phe Asn Pro
    1025                1030                1035

His His Asp Gly Val Gly Leu Asp Glu Phe Val Asp Trp Leu Ile
    1040                1045                1050

Glu Ala Gly His Pro Ile Thr Arg Ile Glu Asp His Ala Thr Trp
    1055                1060                1065

Phe Ala Arg Phe Thr Thr Ala Leu Arg Ala Leu Pro Glu Lys Gln
    1070                1075                1080

Arg Gln Leu Ser Leu Leu Pro Leu Ala Gln Val Tyr Ser Phe Pro
    1085                1090                1095

His Pro Ala Val Asp Gly Ser Pro Phe Arg Asn Ala Val Phe Arg
    1100                1105                1110

Ala Asp Val Gln Arg Ala Arg Ile Gly Lys Asp His Asp Ile Pro
    1115                1120                1125

His Leu Thr Arg Glu Leu Ile Leu Lys Tyr Ala Ala Asp Leu Ala
    1130                1135                1140

Ala Leu Gly Ser Leu
    1145

<210> SEQ ID NO 3
<211> LENGTH: 3447
<212> TYPE: DNA
<213> ORGANISM: Segniliparus rugosus

<400> SEQUENCE: 3
atgggcgacg gcgaagagcg ggcgaagcgt tcttccaga ggatcgggga gctgagcgcg      60
acggacccgc agttcgcggc cgccgcgccg gaccccgccg tggtcgaggc cgtgtcggac    120
ccctcgctct cgttcacccg ctacttggac acgctgatgc gcgggtacgc cgagcgcccg    180
gcgctcgccc accgggtcgg cgcgggatac gagacgatca gctacgggga gctgtgggcg    240
cgggtcgggg cgattgcggc ggcgtggcag gcggacggcc tcgcgccggg cgacttcgtc    300
gccacggtcg gtttcaccag cccggactac gtcgccgtcg accttgcggc cgcgaggtcg    360
gggctggtgt ccgtgccgtt gcaggcgggt gcttcgctcg cccagctcgt cgggatcctc    420
gaggagaccg agccgaaggt gctcgcggcg agcgcgagca gtctcgaagg ggccgttgcc    480
tgcgcgctgg cggccccgag cgtgcagcgg ctcgtcgtgt cgacctgcg cggcccggac    540 gcttcggaga gcgcggcgga cgagcgccga ggcgccctcg ccgatgccga ggagcagctg    600
gcgcgggccg gcgggccgt ggtcgtcgag accctcgccg acctggcggc ccgaggcgag    660
gcgctgccgg aagcccccgct gttcgagccc gccgagggcg aagacccgct ggccctcttg    720
atctacacgt ccggctcgac cggggccccg aaggggcga tgtactcgca gcgcctggtg    780
tcccagctct gggggcgcac gccggtggtg ccggggatgc gaacatctc gctgcattac    840 atgccgctga gccactccta cgggcgggcg gtcctcgccg ggcgctctc ggcggcggg    900 accgcccact tcaccgcgaa cagcgacctt ccaccctct cgaggacat cgcgctcgcc    960 cgccccacct tcctcgccct ggtccccagg gtctgcgaga tgctgttcca ggagagccag   1020
cgcggccagg acgtcgcgga gctgcgcgaa cgggtgctcg gcggtcggct gctggtcgcg   1080
gtgtgcggct ccgccccgct gtcgccggag atgcgcgcgt tcatggagga ggtgctcggc   1140
ttcccgctgc tcgacggcta cggctcgacc gaggcgctcg gcgtcatgcg caacgggatc   1200
atccagcgcc cgccggtcat cgactacaag ctggtcgacg tgcccgagct gggctatcgc   1260

```
accactgaca agccctaccc gaggggcgag ctgtgcatcc gctcgacgag cctgatctcc    1320
ggctactaca agcgcccga gatcacacgcg gaggtgttcg acgcgcaggg ctactacaag    1380
accggcgacg tgatggccga gatcgcgccg gaccacctgg tgtacgtgga ccggagcaag    1440
aacgtcctca aactctccca aggcgagttc gtcgccgtcg cgaagctcga agccgcgtac    1500
ggcacgagcc cgtacgtgaa gcagatcttc gtctacggca acagcgagcg ctccttcctg    1560
ctcgcggtcg tcgtgccgaa cgccgaagtc ctcggcgcgc gggaccagga ggaggccaag    1620
ccgctcatcg ccgcctcgct gcagaagatc gcgaaagagg ctggcctgca gtcttacgag    1680
gtcccgcgcg acttcttgat cgagaccgag ccgttcacca cgcagaacgg cctgctctcc    1740
gaggtcggca agctgctgcg cccgaagctc aaggcccggt acggcgaggc gctggaggcg    1800
cgctacgacg agatcgcgca cggccaggcg gacgagctgc gcgcgctgcg ggacggcgcg    1860
ggacagcgcc cggtggtcga gaccgtcgtg cgggccgccg tcgcgatctc cggctccgag    1920
ggcgcggagg tcggccctga ggcgaacttc gccgacctcg gcggggactc gctctccgcg    1980
ttgagccttg cgaacttgct gcacgacgtc ttcgaagtcg aggtgccggt gcggatcatc    2040
atcggcccga ccgcctcgct cgccgggatc gccaagcaca tcgaggccga gcgcgccggg    2100
gcgagcgccc cgacggcggc ctccgtgcac ggcgcggggg cgacgaggat ccgagcgagc    2160
gagctgacgc tggagaaatt cctccctgaa gacctgcttg ccgccgcgaa gggccttccg    2220
gccgccgacc aggtccgcac ggtgctcttg acgggcgcga acggctggct cgggcgtttc    2280
ctcgcgttgg aacagctcga acggctcgcc gatcggggc aggacggcgg gaagctgatc    2340
tgcctggtcc gggggaaaga cgcggctgcg gcgcgcaggc ggatcgaaga aacgctcggc    2400
acggacccgg ccctggccgc caggttcgcc gaacttgccg aggggcggtt ggaagtggtc    2460 ccggggggacg tgggcgagcc gaagttcggc ttggacgacg cggcatggga ccggctggcc    2520
gaggaggtgg acgtcatcgt ccacccggcg gcccttgtga accacgttct gccgtaccac    2580
cagctgttcg ggccgaacgt ggtcggcacg gcggagatca tccggctcgc gatcaccgcc    2640
aagcgcaagc cggtcaccta cctctccacg gtggcggtcg cggcgggcgt ggagccctcc    2700
tccttcgagg aggacggcga catccgggcc gtggtccccg aacggccctt gggcgatggg    2760
tacgcgaacg gctacggcaa cagcaaatgg gcggggagg tgctgctgcg cgaagcgcac    2820
gagcttgtgg gcctgccggt ggcggtgttc cgctccggaca tgatcctcgc gcacacccgg    2880
tacaccggac agctcaacgt cccccgaccag ttcaccaggc tcgtcctgag ccttttggcc    2940
accgggatcg cgcccaagtc cttctaccag cagggcgcgg cgggcgaacg ccagcgggcg    3000
cattacgacg gcatccccgt ggacttcacc gccgaggcca tcaccacgct cggcgcggag    3060
ccgagctggt cgacggcgg cgcggggttc cgcagcttcg acgtgttcaa cccgcaccac    3120
gacggggtgg gcttggacga gttcgtggac tggctcatcg aggccgggca tccgatctcc    3180
aggatcgacg accacaagga atggttcgcc cggttcgaga ccgccgtgcg cggcctgccc    3240
gaagcgcagc gccagcattc cctgctgccg ctgttgcgcg cctactcgtt cccgcatccg    3300
cccgtggacg gcagtgtcta tccgaccggg aagttccagg gcgcggtcaa agccgcgcag    3360
gtgggctccg accacgacgt gccgcatctc ggcaaggcgc tgatcgtgaa atacgcggac    3420
gacctgaagg ctctcggact cctctga                                         3447

<210> SEQ ID NO 4
<211> LENGTH: 3447
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 4

| | | | | |
|---|---|---|---|---|
| atgggcgacg | gcgaagaacg | tgcgaaacgc | tttttccaac | gtatcggtga actgtctgcg | 60 |
| accgatccgc | agtttgcagc | agcagctccg | gacccggctg | tggttgaagc cgtgagtgat | 120 |
| ccgtcactgt | cgttcacccg | ctatctggat | acgctgatgc | gcggctacgc agaacgtccg | 180 |
| gctctggcac | atcgtgtggg | tgcaggttat | gaaaccatca | gctacggtga actgtgggcc | 240 |
| cgtgttggtg | caattgcagc | agcatggcag | gctgatggtc | tggcaccggg tgacttcgtc | 300 |
| gcaaccgtgg | gttttacgtc | cccggattat | gttgcagtcg | acctggctgc agcacgttca | 360 |
| ggtctggtgt | cggttccgct | gcaagccggt | gcatcactgg | cccagctggt tggcattctg | 420 |
| gaagaaaccg | aaccgaaagt | cctggcagct | tcggcaagct | ctctggaagg cgctgttgcg | 480 |
| tgcgcactgg | cagcaccgag | cgtccagcgc | ctggtcgtgt | ttgatctgcg tggtccggac | 540 |
| gcgagcgaat | ctgcagctga | tgaacgtcgc | ggcgcactgg | ctgacgcaga agaacagctg | 600 |
| gcccgcgcag | gtcgtgcagt | tgtcgtggaa | accctggctg | atctggcagc gcgtggcgaa | 660 |
| gccctgccgg | aagcaccgct | gtttgaaccg | gcggaaggtg | aagatccgct ggccctgctg | 720 |
| atctatacca | gtggctccac | gggtgctccg | aaaggtgcga | tgtacagtca acgcctggtg | 780 |
| tcccagctgt | ggggtcgtac | cccggttgtc | ccgggtatgc | cgaacatttc cctgcattat | 840 |
| atgccgctgt | cacactcgta | cggtcgtgcg | gttctggctg | gtgcactgtc agccggcggt | 900 |
| accgcacatt | tcacggctaa | tagcgatctg | tctaccctgt | ttgaagacat cgcactggca | 960 |
| cgtccgacgt | tcctggcact | ggttccgcgt | gtctgcgaaa | tgctgtttca ggaatcgcaa | 1020 |
| cgcggccagg | atgtggccga | actgcgcgaa | cgtgttctgg | gcggtcgtct gctggtcgca | 1080 |
| gtgtgtggta | gcgctccgct | gtctccggaa | atgcgcgcgt | tcatggaaga agtgctgggc | 1140 |
| tttccgctgc | tggatggcta | tggttcaacc | gaagccctgg | gtgtgatgcg caacggcatt | 1200 |
| atccagcgtc | cgccggttat | tgattacaaa | ctggttgacg | tcccggaact gggttatcgt | 1260 |
| accacggata | agccgtaccc | gcgcggcgaa | ctgtgtatcc | gtagcacgtc tctgattagc | 1320 |
| ggttattaca | acgtccgga | aatcaccgcg | gaagtgtttg | acgcccaggg ttattacaag | 1380 |
| acgggcgatg | ttatggcgga | aattgccccg | gatcatctgg | tgtatgttga ccgtagcaaa | 1440 |
| aatgtgctga | agctgtctca | aggcgaattc | gtcgctgtgg | cgaaactgga agcagcttat | 1500 |
| ggtacctctc | cgtacgtgaa | gcagatcttc | gtttatggca | acagtgaacg ctcctttctg | 1560 |
| ctggcagtgg | ttgtcccgaa | tgcagaagtg | ctgggtgctc | gtgatcagga agaagcgaaa | 1620 |
| ccgctgatcg | cggcctccct | gcaaaaaatt | gcaaaggaag | ctggcctgca gagctatgaa | 1680 |
| gtgccgcgcg | atttcctgat | tgaaaccgaa | ccgtttacca | cgcagaacgg tctgctgtct | 1740 |
| gaagttggca | gctgctgcg | cccgaaactg | aaggcgcgtt | atggcgaagc gctggaagcc | 1800 |
| cgttacgatg | aaatcgcgca | tggtcaagcc | gatgaactgc | gtgcgctgcg tgacggtgcc | 1860 |
| ggtcagcgtc | cggtggttga | aaccgtcgtg | cgtgcagctg | tggcaattag tggctccgaa | 1920 |
| ggtgctgaag | ttggtccgga | agcaaacttt | gctgatctgg | gcggtgactc actgtcggca | 1980 |
| ctgtcgctgg | ctaatctgct | gcacgatgtg | ttcgaagttg | aagtcccggt gcgcattatc | 2040 |
| attggtccga | ccgcgagcct | ggcaggtatc | gcaaaacata | ttgaagcgga acgtgcaggt | 2100 |
| gcatcagctc | cgacggcagc | ctcggttcac | ggcgcaggtg | caacccgtat tcgtgcatcc | 2160 |

| | |
|---|---|
| gaactgacgc tggaaaaatt tctgccggaa gacctgctgg cagctgcaaa gggtctgccg | 2220 |
| gcagcagatc aagtgcgtac cgttctgctg acgggtgcaa atggttggct gggccgtttc | 2280 |
| ctggccctgg aacaactgga acgcctggca cgtagtggtc aggacggcgg taaactgatc | 2340 |
| tgcctggtgc gtggcaagga tgctgcagca gcacgtcgcc gtattgaaga acccctgggt | 2400 |
| acggatccgg cactggctgc acgttttgct gaactggcgg aaggtcgtct ggaagttgtc | 2460 |
| ccgggtgatg tgggcgaacc gaaattcggc ctggatgacg ccgcatggga tcgtctggcg | 2520 |
| gaagaagttg acgtcattgt gcatccggct gcgctggtca accatgtgct gccgtatcac | 2580 |
| cagctgtttg gtccgaatgt ggttggcacc gcggaaatca ttcgcctggc catcacggca | 2640 |
| aaacgtaaac cggtgaccta cctgagcacg gttgccgtcg ccgcaggtgt tgaaccgagt | 2700 |
| tccttcgaag aagatggcga cattcgtgca gtcgtgccgg aacgtccgct gggtgatggt | 2760 |
| tatgcaaacg gctacggtaa ttctaaatgg gcaggtgaag tgctgctgcg tgaagcacat | 2820 |
| gaactggttg gcctgccggt ggcagttttt cgcagtgaca tgatcctggc gcacacccgt | 2880 |
| tatacgggtc aactgaacgt cccggatcag tttacccgtc tggtgctgtc gctgctggca | 2940 |
| acgggtattg caccgaaatc ttttttatcag caaggtgctg caggtgaacg tcagcgtgca | 3000 |
| cactacgatg gcatcccggt ggactttacc gcagaagcta ttaccacgct gggtgccgaa | 3060 |
| ccgtcttggt tcgatggcgg tgcaggcttt cgcagtttcg atgttttttaa tccgcatcac | 3120 |
| gacggcgttg gtctggatga atttgtcgac tggctgatcg aagcgggtca tccgatcagt | 3180 |
| cgtattgatg accacaaaga atggttcgca cgctttgaaa ccgctgtgcg tggcctgccg | 3240 |
| gaagcacagc gccaacatag tctgctgccg ctgctgcgtg cctattcctt tccgcacccg | 3300 |
| ccggttgatg gttcagtcta cccgacgggt aaattccaag gtgcagtcaa ggcagcacaa | 3360 |
| gtgggtagcg atcatgacgt cccgcacctg ggcaaagccc tgattgtgaa gtatgcggat | 3420 |
| gacctgaaag ccctgggcct gctgtaa | 3447 |

<210> SEQ ID NO 5
<211> LENGTH: 3447
<212> TYPE: DNA
<213> ORGANISM: Segniliparus rotundus

<400> SEQUENCE: 5

| | |
|---|---|
| atgggcagcg gcgcggatcg ggcgaagctt ttttttccaaa agatcgagga gctgaccgcg | 60 |
| gcggaccccc agttcgcggc ggcagtgccg gaccaggagg tcgtggcggc ggtttctgat | 120 |
| cccacgctct cgttcacccg ctacctggac acgctcatgc ggggctatgc ggaccgcccc | 180 |
| gccctcgccc accgggtcgg cgatggttac gcgacgatca gctacgggga gctgtggtcg | 240 |
| cgcgtcgggg cgatcgcggc ggcttggagc gcggatggcc tcgaacccgg agatttcgtc | 300 |
| gccaccatcg gcttcacgag ccccgattac accgctctcg acttggcggc gaccaggtcc | 360 |
| ggcctggtgt ccgtgccgtt gcaggcagga gcttctgtcg cgcagctgtc cgcgatcctc | 420 |
| gaagaaaccg cgccgaaggt cttcgcggcg agcgccgaaa gcctcgaagg gcggtggac | 480 |
| tgcgtgctgc ggaccccgag cgtccagcgg ctcgtcatct tcgatctgcg ggacgactcg | 540 |
| cccgagcacc gggcggccct cgcggcggcg aaagccaagc tcgcgcagcc ccagaatccc | 600 |
| gaacaggcgc gaggacccgt ggccgtggag acgctcgacg agctggtcgc gcgcggcgcg | 660 |
| gcgctgcccg agccgcctgt gttcgaaccc gccgagggcg aggacccgtt ggccctgttg | 720 |
| atttacacgt caggctcgac cggcaccccc aaggggggcca tgtactcgca gcgcctcgtg | 780 |
| tcccggttct ggcccaggac cccggtcgtc gcccaactcc cgagtatttc gctgcactac | 840 |

```
atgccoctca gccactccta tggccgggcg gtcctgtgcg ggacgctcgc cgctggcggg    900
accgcgcatt tcaccgccca cagcgacctt tcgaccctct tcgaggacat cgcgctcgcc    960
cgccccacgt tcctcgcgct ggttcccagg gtgtgcgaga tgctgttgca cgagagccgt   1020
cgggcgcggg acctcgctga actgcgcgaa cgggtgctcg gcgagcggct gttggtggcg   1080
gtgtgcggct ccgcgccgtt ggcgcccgag acgcgggcct tcatggagga gctgctcggc   1140
ttccccttgc tcgacggtta cggttcgacc gaggcgctgt cgctcatgcg ggacggggtg   1200
atccaacgcc cgccggtcat cgattacaaa ctggtcgacg tgcccgagct cggctatttc   1260
accaccgaca agccgcaccc ccgggggggag ctgctcatcc gctccgaaag cctcgtctcc   1320
ggctactaca agcgcccga gctgacagcg gagatgttcg acgagcaggg ctactacaaa   1380
accgcgacg tgatgccga gatcgcgccg gaccgcctcg tctacgtgga ccggagcaaa   1440
aacgtcctca agctctccca gggcgagttc gtcgcggtcg cgaagctgga ggccgccttc   1500
ggcgcgagcc cgtatgtcaa gcagatcttc gtctacggca acagcgagcg ctcgttcctg   1560
ctcgcggtgg tcgtgccgaa cgccgaactc gtcggccggc tcgacaccgt ccaggcgctg   1620
gccgaagtga agccgctcat cgcggactcg ctcgccgcga tcgccaaaga gtctggcctg   1680
cagtcctatg aggtcccgcg cgacttcatc gtcgagaccg agccgttcac caccggcaac   1740
ggactgctct ccgaagtcgg caagcttttg cgcccgaagc tcaaggagcg gtacggcgaa   1800
cggctcgaag cgctctacga ccagatcgcg cagggccagg cggatgaact gcgcgcgttg   1860
cgcgagcagg cgggggagcg cccggtgatc gacacagtcc gcaaagccgc cgcagcagtg   1920
gtgggctcca gcggcgcgga ctttcggcct gacgcgaatt cgccgacct cggcggagac   1980
tcgctctccg cgttgggttt cgcgaacctt ttgcaggacg tgttcggggt cgagacgccc   2040
gttcggatca tcatcggccc gaccgcgtcg ctcgccggga tcgccgagca catcgagcgc   2100
gcgttgggcg gtcgcccggg cgaggcggcg ccgaactcgg cctcggtgca cggcgccggg   2160
gccgaggtga tccgcgcgag cgatctgacg ttggacaaat tcctggacgc gcaggcgctc   2220
gaagctgcgc agagcctgcc caggcccacc ggctcccatc gcaccgtgct gctcaccggc   2280
gcgaacggct ggctcggacg gtttctcgcg ctcgagcagc ttcagcggct cgaagccacc   2340
ggcgggaagc tgatctgctt ggtcaggggc aaagacgcgg cctcggcgcg cgcgcgggtc   2400
gaagaagcgc tcggcaccga cccggcgctc gcggcccggt tcgccgaact cgccgcagac   2460
cggctcgaag tggttcccgg cgacgtcggc gagccgaagt tcggcctgga cgatcgcacc   2520
tgggaccggc ttgcgggcga ggtggacgct gtggtgcact ccggcgcctt ggtgaaccac   2580
gttctgccgt accaccagct cttcgggtcg aacgtggtcg gcgtcgccga gatcatccgc   2640
ttcgccgtcg cctcgaagct caaacctgtc gcctacctct ccaccgtcgc cgtcgcggca   2700
ggcgccgacc ccgccgcatt cgacgaggac ggcgacatcc gcgaagtcgt gccccaacga   2760
cctgtcgacac acagctacgc caacggctac ggcaacagca aatgggccgg cgaggtcctg   2820
ctccgcgaag cgcacgagcg caccggcctg cctgtgcgcg tcttccgctc cgacatgatc   2880
ctcgcccacc ggcaacacac cggcagctc aacgccaccg accaattcac acggctcatc   2940
ctcagcctcc tcgccaccgg cctcgccccg aagtccttct accaactcga ccccaaggc    3000
agacggcaac gggcccacta cgacggcatt cccgtggact tcaccgccga ggccatcgtc   3060
gccctcgccg ccgaaggcaa caacggccac cgcagctaca acgtcttcaa ccccaccac   3120
gacggcgtcg gcttggacga gttcgtcgac tggctcatcg aagccggaca tcccatcacc   3180
```

```
cgcatcgaag accacgcgac atggttcgcc cgtttcacga ccgcgctccg cgccctcccg    3240
gaaaaacaac gccagctgtc gctgttgccg cttgcgcagg tgtactcgtt cccgcatccg    3300
gctgttgacg gctcgccgtt ccggaacgcc gtgttccggg ccgatgtgca gagggcgagg    3360
atcggcaagg accacgatat tccgcatctg acgcgggagc tgatcctgaa atacgccgcc    3420
gacctggcag cgctcggctt gttgtag                                       3447
```

<210> SEQ ID NO 6
<211> LENGTH: 3447
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atgggctctg gagcggatcg cgcgaagctg ttctttcaga aaattgaaga actgactgca      60
gcggacccac aatttgcagc agccgtgccc gatcaggaag tggtggccgc cgtaagcgac     120
ccaactctgt cgtttacccg ttatctcgat accctgatgc gtggctatgc ggatcgtccg     180
gcactggcgc atcgcgttgg tgacggttat gcgaccatct cttacgggga actgtggtca     240
cgcgttggag cgattgctgc agcctggagc gcggatggac tggagccggg tgattttgtg     300
gctacgattg ggttcactag tccggactat accgccctgg atctggcagc gacccgttcc     360
gggctcgtta gcgttccgct gcaggcgggc gctagtgtgg cgcagctgtc ggcgatcctg     420
gaggaaacag cccctaaagt tttcgcagcg agcgccgaaa gcctgaagg tgctgtggat      480 tgcgttttgc gcaccccgag tgtgcagcgc ctggtcattt tcgacttacg ggatgatagc     540
cctgagcatc gcgctgcctt agcggctgca aaagcgaaac ttgctcagcc gcagaatccc     600
gaacaggccc gcgggccggt agcggtagag acactggatg aactggttgc tcgtggtgcg     660
gcacttccgg aacctcctgt ctttgaacca gcggaaggtg aagatccgct ggccctcctg     720
atctacacca gcggttccac cggcacgccg aaagggcaa tgtactcgca gcgccttgta      780
tctcgcttct ggcccccgca gccggtcgtt gcgcagctgc catccatctc acttcactac     840
atgccgctta gccacagcta tggccgtgcc gtgctgtgtg gcaccctggc ggctggtggt     900
acagcgcact ttacggctca tagcgatctg tccacgctgt ttgaagatat tgccctcgca     960
cgcccgacgt ttctggcact ggtcccgcgt gtctgcgaaa tgctgctcca cgagtcgcgc    1020
cgcgcgcgtg acttagcaga actgcgcgaa cgggttttgg gtgaacgcct gctcgtggcg    1080
gtttgtggta gtgcgcctct tgcgccagaa acccgcgcgt ttatggaaga gctgctgggc    1140
tttccactgc tggatggcta tggctcaacc gaagcgttga gcctgatgcg cgatggcgtg    1200
attcagcgtc ctccggtaat tgactacaaa ttggtggacg tccggaact gggttacttt     1260 accaccgata aaccgcatcc ccgtggcgaa ctgttgattc gctctgaatc tcttgtaagc    1320
ggttactata aacgtccaga attgacagcg gagatgttcg atgagcaagg ttactacaag    1380
accggcgatg taatggccga aattgccccg gaccgcctgg tctacgttga ccgctccaag    1440
aacgtcctga actgtcgca agggaattt gttgccgtgg caaaattgga ggccgcattc     1500
ggcgcaagcc cgtatgtcaa gcagattttc gtctatggta acagtgaacg ctcttttctg    1560
cttgcagtag tcgtaccaaa cgccgaatta gtgggccgtc ttgacacagt tcaagccctg    1620
gccgaagtca aacccttaat cgcagatagt ttagcggcta ttgcgaaaga aagcggcttg    1680
caatcctatg aagtcccgcg cgactttatc gttgaaaccg agccgtttac gacgggcaat    1740
```

```
ggcctgctttt ctgaagttgg caaactcctg cggcccaaac tcaaggaacg ttacggtgag      1800
cgcctggagg cgctgtacga tcagattgca cagggccaag ctgacgagtt gcgtgcattg      1860
cgtgaacagg cgggcgaacg cccagtgatc gatacggtgc gcaaagccgc tgccgcggtg      1920
gtggggtcat caggggccga ttttcgccca gatgctaatt tcgcagatct gggaggtgat      1980
agcctgtcag cgctggggtt cgccaattta ctgcaagatg tgttcggcgt tgaaactccg      2040
gtccggatca ttattggacc tactgcagt ctggcgggca ttgccgaaca tatcgaacgc       2100
gctttaggcg gtcgccctgg cgaagcggca ccaaattcgg caagtgtgca tggcgcgggt      2160
gcagaagtaa tccgcgcatc tgacctgacg ttagacaaat tcttggacgc tcaagcctta      2220
gaagccgcgc agtcgttacc acgtccgaca ggcagccatc ggacggtcct gttgactgga      2280
gcgaatggat ggttagggcg cttcctggcg ctcgagcagt tgcagcgctt agaagccacg      2340
ggcggaaaac tgatctgctt agtgcgcggt aaagacgcag cgtcagcgcg tgcacgcgtg      2400
gaggaagcgc tgggcaccga tcccgcatta gcagcgcgct ttgccgagct ggccgcagat      2460
cgtctggaag ttgttccggg tgacgtgggc gaaccgaagt tcggtctgga cgatcgcacg      2520
tgggatcggc tggctggtga ggtagatgcg gtagtccatt ctggcgcgct ggttaaccac      2580
gttttgccct atcaccagct gttcggcagt aacgtggtgg gcgtggcaga aatcatccgt      2640
ttcgctgtgg cctctaaact taaaccggtg gcctatctct ccactgttgc tgtggctgcg      2700
ggcgccgatc ctgccgcgtt tgatgaagat ggtgacattc gggaggtagt gccgcaacgc      2760
ccggtcgatg actcgtatgc caacggctat ggcaacagca gtgggcggg tgaggtgctg       2820 ttacgcgaag cacacgaacg taccgggctg ccggtgcgtg tctttcgcag tgacatgatt      2880
ctggcccatc gccaacacac cggccagctc aatgcgaccg accagtttac ccgtctgatt      2940
ctgtccttac tggctactgg tttggctcca aaatcgttct atcagttaga tccgcaaggt      3000
cgtcgccagc gtgcacatta cgacggtatt ccggtcgatt ttacggctga ggcgatcgtt      3060
gcccttgccg ccgagggaaa taatgggcac cgttcctata acgtctttaa cccgcaccat      3120
gatggggttg ggctggacga gtttgtggat tggctgatcg aagccggtca tccgattacc      3180
cgcattgagg atcacgccac atggttcgcc cgttttacca ctgcgctgcg ggcgcttcct      3240
gagaaacaac gccagttgtc gttgctccct ctggctcagg tgtatagctt tccccatccg      3300
gcggttgatg gatccccgtt ccgtaacgca gtatttcgtg cggacgtgca acgtgcgcgt      3360
attggtaaag atcatgatat tccgcatctc acccgtgaac tgatcctgaa atatgctgcc      3420
gatctggccg ctctcggctc actttaa                                          3447
```

<210> SEQ ID NO 7
<211> LENGTH: 1148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
        35                  40                  45

Leu Asp Thr Leu Met Arg Gly Tyr Ala Glu Arg Pro Ala Leu Ala His

```
              50                  55                  60
Arg Val Gly Ala Gly Tyr Glu Thr Ile Ser Tyr Gly Glu Leu Trp Ala
 65                  70                  75                  80

Arg Val Gly Ala Ile Ala Ala Trp Gln Ala Asp Gly Leu Ala Pro
                 85                  90                  95

Gly Asp Phe Val Ala Thr Val Gly Phe Thr Ser Pro Asp Tyr Val Ala
                    100                 105                 110

Val Asp Leu Ala Ala Ala Arg Ser Gly Leu Val Ser Val Pro Leu Gln
                115                 120                 125

Ala Gly Ala Ser Leu Ala Gln Leu Val Gly Ile Leu Glu Glu Thr Glu
                130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                    165                 170                 175

Arg Gly Pro Asp Ala Ser Glu Ser Ala Ala Asp Glu Arg Arg Gly Ala
                180                 185                 190

Leu Ala Asp Ala Glu Glu Gln Leu Ala Arg Ala Gly Arg Ala Val Val
                195                 200                 205

Val Glu Thr Leu Ala Asp Leu Ala Ala Arg Gly Glu Ala Leu Pro Glu
210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                    245                 250                 255

Gln Arg Leu Val Ser Gln Leu Trp Gly Arg Thr Pro Val Val Pro Gly
                260                 265                 270

Met Pro Asn Ile Ser Leu His Tyr Met Pro Leu Ser His Ser Tyr Gly
                275                 280                 285

Arg Ala Val Leu Ala Gly Ala Leu Ser Ala Gly Gly Thr Ala His Phe
                290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                    325                 330                 335

Gln Glu Ser Gln Arg Gly Gln Asp Val Ala Glu Leu Arg Glu Arg Val
                340                 345                 350

Leu Gly Gly Arg Leu Leu Val Ala Val Cys Gly Ser Ala Pro Leu Ser
                355                 360                 365

Pro Glu Met Arg Ala Phe Met Glu Glu Val Leu Gly Phe Pro Leu Leu
                370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                    405                 410                 415

Leu Gly Tyr Arg Thr Thr Asp Lys Pro Tyr Pro Arg Gly Glu Leu Cys
                420                 425                 430

Ile Arg Ser Thr Ser Leu Ile Ser Gly Tyr Tyr Lys Arg Pro Glu Ile
                435                 440                 445

Thr Ala Glu Val Phe Asp Ala Gln Gly Tyr Tyr Lys Thr Gly Asp Val
                450                 455                 460

Met Ala Glu Ile Ala Pro Asp His Leu Val Tyr Val Asp Arg Ser Lys
465                 470                 475                 480
```

```
Asn Val Leu Lys Leu Ser Gln Gly Glu Phe Val Ala Val Ala Lys Leu
            485                 490                 495
Glu Ala Ala Tyr Gly Thr Ser Pro Tyr Val Lys Gln Ile Phe Val Tyr
        500                 505                 510
Gly Asn Ser Glu Arg Ser Phe Leu Leu Ala Val Val Pro Asn Ala
        515                 520                 525
Glu Val Leu Gly Ala Arg Asp Gln Glu Ala Lys Pro Leu Ile Ala
    530                 535                 540
Ala Ser Leu Gln Lys Ile Ala Lys Glu Ala Gly Leu Gln Ser Tyr Glu
545                 550                 555                 560
Val Pro Arg Asp Phe Leu Ile Glu Thr Glu Pro Phe Thr Thr Gln Asn
                565                 570                 575
Gly Leu Leu Ser Glu Val Gly Lys Leu Leu Arg Pro Lys Leu Lys Ala
                580                 585                 590
Arg Tyr Gly Glu Ala Leu Glu Ala Arg Tyr Asp Glu Ile Ala His Gly
                595                 600                 605
Gln Ala Asp Glu Leu Arg Ala Leu Arg Asp Gly Ala Gly Gln Arg Pro
    610                 615                 620
Val Val Glu Thr Val Val Arg Ala Ala Val Ala Ile Ser Gly Ser Glu
625                 630                 635                 640
Gly Ala Glu Val Gly Pro Glu Ala Asn Phe Ala Asp Leu Gly Gly Asp
                645                 650                 655
Ser Leu Ser Ala Leu Ser Leu Ala Asn Leu Leu His Asp Val Phe Glu
                660                 665                 670
Val Glu Val Pro Val Arg Ile Ile Ile Gly Pro Thr Ala Ser Leu Ala
                675                 680                 685
Gly Ile Ala Lys His Ile Glu Ala Glu Arg Ala Gly Ala Ser Ala Pro
        690                 695                 700
Thr Ala Ala Ser Val His Gly Ala Gly Ala Thr Arg Ile Arg Ala Ser
705                 710                 715                 720
Glu Leu Thr Leu Glu Lys Phe Leu Pro Glu Asp Leu Leu Ala Ala Ala
                725                 730                 735
Lys Gly Leu Pro Ala Ala Asp Gln Val Arg Thr Val Leu Leu Thr Gly
                740                 745                 750
Ala Asn Gly Trp Leu Gly Arg Phe Leu Ala Leu Glu Gln Leu Glu Arg
        755                 760                 765
Leu Ala Arg Ser Gly Gln Asp Gly Gly Lys Leu Ile Cys Leu Val Arg
    770                 775                 780
Gly Lys Asp Ala Ala Ala Arg Arg Ile Glu Glu Thr Leu Gly
785                 790                 795                 800
Thr Asp Pro Ala Leu Ala Arg Phe Ala Glu Leu Ala Glu Gly Arg
                805                 810                 815
Leu Glu Val Val Pro Gly Asp Val Gly Glu Pro Lys Phe Gly Leu Asp
                820                 825                 830
Asp Ala Ala Trp Asp Arg Leu Ala Glu Glu Val Asp Val Ile Val His
            835                 840                 845
Pro Ala Ala Leu Val Asn His Val Leu Pro Tyr His Gln Leu Phe Gly
        850                 855                 860
Pro Asn Val Val Gly Thr Ala Glu Ile Ile Arg Leu Ala Ile Thr Ala
865                 870                 875                 880
Lys Arg Lys Pro Val Thr Tyr Leu Ser Thr Val Ala Val Ala Ala Gly
                885                 890                 895
```

-continued

Val Glu Pro Ser Ser Phe Glu Glu Asp Gly Asp Ile Arg Ala Val Val
            900                 905                 910

Pro Glu Arg Pro Leu Gly Asp Gly Tyr Ala Asn Gly Tyr Gly Asn Ser
            915                 920                 925

Lys Trp Ala Gly Glu Val Leu Leu Arg Glu Ala His Glu Leu Val Gly
            930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
            965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
            995                 1000                1005

Phe Thr Ala Glu Ala Ile Thr Thr Leu Gly Ala Glu Pro Ser Trp
            1010                1015                1020

Phe Asp Gly Gly Ala Gly Phe Arg Ser Phe Asp Val Phe Asn Pro
            1025                1030                1035

His His Asp Gly Val Gly Leu Asp Glu Phe Val Asp Trp Leu Ile
            1040                1045                1050

Glu Ala Gly His Pro Ile Ser Arg Ile Asp Asp His Lys Glu Trp
            1055                1060                1065

Phe Ala Arg Phe Glu Thr Ala Val Arg Gly Leu Pro Glu Ala Gln
            1070                1075                1080

Arg Gln His Ser Leu Leu Pro Leu Leu Arg Ala Tyr Ser Phe Pro
            1085                1090                1095

His Pro Pro Val Asp Gly Ser Val Tyr Pro Thr Gly Lys Phe Gln
            1100                1105                1110

Gly Ala Val Lys Ala Ala Gln Val Gly Ser Asp His Asp Val Pro
            1115                1120                1125

His Leu Gly Lys Ala Leu Ile Val Lys Tyr Ala Asp Asp Leu Lys
            1130                1135                1140

Ala Leu Gly Leu Leu
            1145

<210> SEQ ID NO 8
<211> LENGTH: 1148
<212> TYPE: PRT
<213> ORGANISM: Segniliparus rotundus

<400> SEQUENCE: 8

Met Gly Ser Gly Ala Asp Arg Ala Lys Leu Phe Phe Gln Lys Ile Glu
1               5                   10                  15

Glu Leu Thr Ala Ala Asp Pro Gln Phe Ala Ala Val Pro Asp Gln
            20                  25                  30

Glu Val Val Ala Ala Val Ser Asp Pro Thr Leu Ser Phe Thr Arg Tyr
            35                  40                  45

Leu Asp Thr Leu Met Arg Gly Tyr Ala Asp Arg Pro Ala Leu Ala His
50                  55                  60

Arg Val Gly Asp Gly Tyr Ala Thr Ile Ser Tyr Gly Glu Leu Trp Ser
65                  70                  75                  80

Arg Val Gly Ala Ile Ala Ala Ala Trp Ser Ala Asp Gly Leu Glu Pro
                85                  90                  95

Gly Asp Phe Val Ala Thr Ile Gly Phe Thr Ser Pro Asp Tyr Thr Ala
                100                 105                 110

```
Leu Asp Leu Ala Ala Thr Arg Ser Gly Leu Val Ser Val Pro Leu Gln
        115                 120                 125

Ala Gly Ala Ser Val Ala Gln Leu Ser Ala Ile Leu Glu Glu Thr Ala
130                 135                 140

Pro Lys Val Phe Ala Ala Ser Ala Glu Ser Leu Glu Gly Ala Val Asp
145                 150                 155                 160

Cys Val Leu Arg Thr Pro Ser Val Gln Arg Leu Val Ile Phe Asp Leu
                165                 170                 175

Arg Asp Asp Ser Pro Glu His Arg Ala Ala Leu Ala Ala Ala Lys Ala
                180                 185                 190

Lys Leu Ala Gln Pro Gln Asn Pro Glu Gln Ala Arg Gly Pro Val Ala
        195                 200                 205

Val Glu Thr Leu Asp Glu Leu Val Ala Arg Gly Ala Ala Leu Pro Glu
        210                 215                 220

Pro Pro Val Phe Glu Pro Ala Gly Glu Asp Pro Leu Ala Leu Leu
225                 230                 235                 240

Ile Tyr Thr Ser Gly Ser Thr Gly Thr Pro Lys Gly Ala Met Tyr Ser
                245                 250                 255

Gln Arg Leu Val Ser Arg Phe Trp Pro Arg Thr Pro Val Val Ala Gln
        260                 265                 270

Leu Pro Ser Ile Ser Leu His Tyr Met Pro Leu Ser His Ser Tyr Gly
        275                 280                 285

Arg Ala Val Leu Cys Gly Thr Leu Ala Ala Gly Gly Thr Ala His Phe
290                 295                 300

Thr Ala His Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Leu
                325                 330                 335

His Glu Ser Arg Arg Ala Arg Asp Leu Ala Glu Leu Arg Glu Arg Val
                340                 345                 350

Leu Gly Glu Arg Leu Leu Val Ala Val Cys Gly Ser Ala Pro Leu Ala
        355                 360                 365

Pro Glu Thr Arg Ala Phe Met Glu Glu Leu Leu Gly Phe Pro Leu Leu
        370                 375                 380

Asp Gly Tyr Gly Ser Thr Glu Ala Leu Ser Leu Met Arg Asp Gly Val
385                 390                 395                 400

Ile Gln Arg Pro Pro Val Ile Asp Tyr Lys Leu Val Asp Val Pro Glu
                405                 410                 415

Leu Gly Tyr Phe Thr Thr Asp Lys Pro His Pro Arg Gly Glu Leu Leu
                420                 425                 430

Ile Arg Ser Glu Ser Leu Val Ser Gly Tyr Tyr Lys Arg Pro Glu Leu
        435                 440                 445

Thr Ala Glu Met Phe Asp Glu Gln Gly Tyr Tyr Lys Thr Gly Asp Val
450                 455                 460

Met Ala Glu Ile Ala Pro Asp Arg Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Phe Gly Ala Ser Pro Tyr Val Lys Gln Ile Phe Val Tyr
                500                 505                 510

Gly Asn Ser Glu Arg Ser Phe Leu Leu Ala Val Val Val Pro Asn Ala
        515                 520                 525
```

```
Glu Leu Val Gly Arg Leu Asp Thr Val Gln Ala Leu Ala Glu Val Lys
    530                 535                 540
Pro Leu Ile Ala Asp Ser Leu Ala Ala Ile Ala Lys Glu Ser Gly Leu
545                 550                 555                 560
Gln Ser Tyr Glu Val Pro Arg Asp Phe Ile Val Glu Thr Glu Pro Phe
                565                 570                 575
Thr Thr Gly Asn Gly Leu Leu Ser Glu Val Gly Lys Leu Leu Arg Pro
            580                 585                 590
Lys Leu Lys Glu Arg Tyr Gly Glu Arg Leu Glu Ala Leu Tyr Asp Gln
        595                 600                 605
Ile Ala Gln Gly Gln Ala Asp Glu Leu Arg Ala Leu Arg Glu Gln Ala
    610                 615                 620
Gly Glu Arg Pro Val Ile Asp Thr Val Arg Lys Ala Ala Ala Ala Val
625                 630                 635                 640
Val Gly Ser Ser Gly Ala Asp Phe Arg Pro Asp Ala Asn Phe Ala Asp
                645                 650                 655
Leu Gly Gly Asp Ser Leu Ser Ala Leu Gly Phe Ala Asn Leu Leu Gln
            660                 665                 670
Asp Val Phe Gly Val Glu Thr Pro Val Arg Ile Ile Gly Pro Thr
    675                 680                 685
Ala Ser Leu Ala Gly Ile Ala Glu His Ile Glu Arg Ala Leu Gly Gly
690                 695                 700
Arg Pro Gly Glu Ala Ala Pro Asn Ser Ala Ser Val His Gly Ala Gly
705                 710                 715                 720
Ala Glu Val Ile Arg Ala Ser Asp Leu Thr Leu Asp Lys Phe Leu Asp
                725                 730                 735
Ala Gln Ala Leu Glu Ala Ala Gln Ser Leu Pro Arg Pro Thr Gly Ser
            740                 745                 750
His Arg Thr Val Leu Leu Thr Gly Ala Asn Gly Trp Leu Gly Arg Phe
        755                 760                 765
Leu Ala Leu Glu Gln Leu Gln Arg Leu Glu Ala Thr Gly Gly Lys Leu
    770                 775                 780
Ile Cys Leu Val Arg Gly Lys Asp Ala Ala Ser Ala Arg Ala Arg Val
785                 790                 795                 800
Glu Glu Ala Leu Gly Thr Asp Pro Ala Leu Ala Ala Arg Phe Ala Glu
                805                 810                 815
Leu Ala Ala Asp Arg Leu Glu Val Val Pro Gly Asp Val Gly Glu Pro
            820                 825                 830
Lys Phe Gly Leu Asp Asp Arg Thr Trp Asp Arg Leu Ala Gly Glu Val
        835                 840                 845
Asp Ala Val Val His Ser Gly Ala Leu Val Asn His Val Leu Pro Tyr
    850                 855                 860
His Gln Leu Phe Gly Ser Asn Val Val Gly Val Ala Glu Ile Ile Arg
865                 870                 875                 880
Phe Ala Val Ala Ser Lys Leu Lys Pro Val Ala Tyr Leu Ser Thr Val
                885                 890                 895
Ala Val Ala Ala Gly Ala Asp Pro Ala Ala Phe Asp Glu Asp Gly Asp
            900                 905                 910
Ile Arg Glu Val Val Pro Gln Arg Pro Val Asp Asp Ser Tyr Ala Asn
        915                 920                 925
Gly Tyr Gly Asn Ser Lys Trp Ala Gly Glu Val Leu Leu Arg Glu Ala
    930                 935                 940
His Glu Arg Thr Gly Leu Pro Val Arg Val Phe Arg Ser Asp Met Ile
```

-continued

```
                     945                 950                 955                 960
Leu Ala His Arg Gln His Thr Gly Gln Leu Asn Ala Thr Asp Gln Phe
                    965                 970                 975
Thr Arg Leu Ile Leu Ser Leu Leu Ala Thr Gly Leu Ala Pro Lys Ser
                    980                 985                 990
Phe Tyr Gln Leu Asp Pro Gln Gly Arg Arg Gln Arg Ala His Tyr Asp
                995                 1000                1005
Gly Ile Pro Val Asp Phe Thr Ala Glu Ala Ile Val Ala Leu Ala
            1010                1015                1020
Ala Glu Gly Asn Asn Gly His Arg Ser Tyr Asn Val Phe Asn Pro
            1025                1030                1035
His His Asp Gly Val Gly Leu Asp Glu Phe Val Asp Trp Leu Ile
            1040                1045                1050
Glu Ala Gly His Pro Ile Thr Arg Ile Glu Asp His Ala Thr Trp
            1055                1060                1065
Phe Ala Arg Phe Thr Thr Ala Leu Arg Ala Leu Pro Glu Lys Gln
            1070                1075                1080
Arg Gln Leu Ser Leu Leu Pro Leu Ala Gln Val Tyr Ser Phe Pro
            1085                1090                1095
His Pro Ala Val Asp Gly Ser Pro Phe Arg Asn Ala Val Phe Arg
            1100                1105                1110
Ala Asp Val Gln Arg Ala Arg Ile Gly Lys Asp His Asp Ile Pro
            1115                1120                1125
His Leu Thr Arg Glu Leu Ile Leu Lys Tyr Ala Ala Asp Leu Ala
            1130                1135                1140
Ala Leu Gly Leu Leu
            1145

<210> SEQ ID NO 9
<211> LENGTH: 3447
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgggcgacg gcgaagaacg tgcgaaacgc ttttttccaac gtatcggtga actgtctgcg      60
accgatccgc agtttgcagc agcagctccg gacccggctg tggttgaagc cgtgagtgat     120
ccgtcactgt cgttcacccg ctatctggat acgctgatgc gcggctacgc agaacgtccg     180
gctctggcac atcgtgtggg tgcaggttat gaaaccatca gctacggtga actgtgggcc     240
cgtgttggtg caattgcagc agcatggcag gctgatggtc tggcaccggg tgacttcgtc     300
gcaaccgtgg gttttacgtc cccggattat gttgcagtcg acctggctgc agcacgttca     360
ggtctggtgt cggttccgct gcaagccggt gcatcactgg cccagctggt tggcattctg     420
gaagaaaccg aaccgaaagt cctggcagct tcggcaagct ctctggaagg cgctgttgcg     480
tgcgcactgg cagcaccgag cgtccagcgc ctggtcgtgt ttgatctgcg tggtccggac     540
gcgagcgaat ctgcagctga tgaacgtcgc ggcgcactgg ctgacgcaga agaacagctg     600
gcccgcgcag tcgtgcagt tgtcgtggaa accctggctg atctggcagc gcgtggcgaa     660
gccctgccgg aagcaccgct gtttgaaccg gcggaaggtg aagatccgct ggccctgctg     720
atctatacca gtggctccac gggtgctccg aaaggtgcga tgtacagtca acgcctggtg     780
tcccagctgt ggggtcgtac cccggttgtc ccgggtatgc cgaacatttc cctgcattat     840
```

```
atgccgctgt cacactcgta cggtcgtgcg gttctggctg gtgcactgtc agccggcggt    900
accgcacatt tcacggctaa tagcgatctg tctaccctgt ttgaagacat cgcactggca    960
cgtccgacgt tcctggcact ggttccgcgt gtctgcgaaa tgctgtttca ggaatcgcaa   1020
cgcggccagg atgtggccga actgcgcgaa cgtgttctgg gcggtcgtct gctggtcgca   1080
gtgtgtggta gcgctccgct gtcttctgaa atgcgcgcgt tcatggaaga agtgctggaa   1140
tttccgctgc tggatggcta tggttcaacc gaagccctgg gtgtgatgcg caacggcatt   1200
atccagcgtc cgccggttat tgattacaaa ctggttgacg tcccggaact gggttatcgt   1260
accacggata agccgtaccc gcgcggcgaa ctgtgtatcc gtagcacgtc tctgattagc   1320
ggttattaca aacgtccgga aatcaccgcg gaagtgtttg acgcccaggg ttattacaag   1380
acgggcgatg ttatggcgga aattgccccg gatcatctgg tgtatgttga ccgtagcaaa   1440
aatgtgctga agctgtctca aggcgaattc gtcgctgtgg cgaaactgga agcagcttat   1500
ggtacctctc cgtacgtgaa gcagatcttc gtttatggca acagtgaacg ctccttctg    1560
ctggcagtgg ttgtcccgaa tgcagaagtg ctgggtgctc gtgatcagga agaagcgaaa   1620
ccgctgatcg cggcctccct gcaaaaaatt gcaaaggaag ctggcctgca gagctatgaa   1680
gtgccgcgcg atttcctgat tgaaaccgaa ccgtttacca cgcagaacgg tctgctgtct   1740
gaagttggca gctgctgcg cccgaaactg aaggcgcgtt atggcgaagc gctggaagcc   1800
cgttacgatg aaatcgcgca tggtcaagcc gatgaactgc gtgcgctgcg tgacctggcc   1860
ggtcagcgtc cggtggttga accgtcgtg cgtgcagctg tggcaattag tggctccgaa   1920
ggtgctgaag ttggtccgga agcaaacttt gctgatctgg gcggtgactc actgtcggca   1980
ctgtcgctgg ctaatctgct gcacgatgtg ttcgaagttg aagtcccggt gcgcattatc   2040
attggtccga ccgcgagcct ggcaggtatc gcacgtcata ttgaagcgga acgtgcaggt   2100
gcatcagctc cgacggcagc ctcggttcac ggcgcaggtg caacccgtat tcgtgcatcc   2160
gaactgacgc tggaaaaatt tctgccggaa gacctgctgg cagctgcaaa gggtctgccg   2220
gcagcagatc aagtgcgtac cgttctgctg acgggtgcaa atggttggct gggccgtttc   2280
ctggccctgg aacaactgga acgcctggca cgtagtggtc aggacggcgg taaactgatc   2340
tgcctggtgc gtggcaagga tgctgcagca gcacgtcgcc gtattgaaga acccctgggt   2400
acggatccgg cactggctgc acgttttgct gaactggcgg aaggtcgtct ggaagttgtc   2460
ccgggtgatg tgggcgaacc gaaattcggc ctggatgacg ccgcatggga tcgtctggcg   2520
gaagaagttg acgtcattgt gcatccggct gcgctggtca accatgtgct gccgtatcac   2580
cagctgtttg gtccgaatgt ggttggcacc gcggaaatca ttcgcctggc catcacggca   2640
aaacgtaaac cggtgaccta cctgagcacg gttgccgtcg ccgcaggtgt tgaaccgagt   2700
tccttcgaag aagatggcga cattcgtgca gtcgtgccgg aacgtccgct gggtgatggt   2760
tatgcaaacg gctacggtaa ttctaaatgg gcaggtgaag tgctgctgcg tgaagcacat   2820
gaactggttg gcctgccggt ggcagttttt cgcagtgaca tgatcctggc gcacacccgt   2880
tatacgggtc aactgaacgt cccggatcag tttacccgtc tggtgctgtc gctgctggca   2940
acgggtattg caccgaaatc tttttatcag caaggtgctg caggtgaacg tcagcgtgca   3000
cactacgatg gcatcccggt ggactttacc gcagaagcta ttaccacgct gggtgccgaa   3060
ccgtcttggt tcgatggcgg tgcaggcttt cgcagtttcg atgtttttaa tccgcatcac   3120
gacggcgttg gtctggatga atttgtcgac tggctgatcg aagcgggtca tccgatcagt   3180
```

```
cgtattgatg accacaaaga atggttcgca cgctttgaaa ccgctgtgcg tggcctgccg    3240
gaagcacagc gccaacatag tctgctgccg ctgctgcgtg cctattcctt tccgcacccg    3300
ccggttgatg gttcagtcta cccgacgggt aaattccaag gtgcagtcaa ggcagcacaa    3360
gtgggtagcg atcatgacgt cccgcacctg ggcaaagccc tgattgtgaa gtatgcggat    3420
gacctgaaag ccctgggcct gctgtaa                                         3447
```

<210> SEQ ID NO 10
<211> LENGTH: 1148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
        35                  40                  45

Leu Asp Thr Leu Met Arg Gly Tyr Ala Glu Arg Pro Ala Leu Ala His
    50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Ala Trp Gln Ala Asp Gly Leu Ala Pro
                85                  90                  95

Gly Asp Phe Val Ala Thr Val Gly Phe Thr Ser Pro Asp Tyr Val Ala
            100                 105                 110

Val Asp Leu Ala Ala Ala Arg Ser Gly Leu Val Ser Val Pro Leu Gln
        115                 120                 125

Ala Gly Ala Ser Leu Ala Gln Leu Val Gly Ile Leu Glu Glu Thr Glu
    130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
            180                 185                 190

Leu Ala Asp Ala Glu Gln Leu Ala Arg Ala Gly Arg Ala Val Val
        195                 200                 205

Val Glu Thr Leu Ala Asp Leu Ala Ala Arg Gly Glu Ala Leu Pro Glu
    210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
            260                 265                 270

Met Pro Asn Ile Ser Leu His Tyr Met Pro Leu Ser His Ser Tyr Gly
        275                 280                 285

Arg Ala Val Leu Ala Gly Ala Leu Ser Ala Gly Gly Thr Ala His Phe
    290                 295                 300

Thr Ala Asn Ser Asp Leu Ser Thr Leu Phe Glu Asp Ile Ala Leu Ala
```

-continued

```
            305                 310                 315                 320
Arg Pro Thr Phe Leu Ala Leu Val Pro Arg Val Cys Glu Met Leu Phe
                    325                 330                 335
Gln Glu Ser Gln Arg Gly Gln Asp Val Ala Glu Leu Arg Glu Arg Val
                    340                 345                 350
Leu Gly Gly Arg Leu Leu Val Ala Val Cys Gly Ser Ala Pro Leu Ser
                    355                 360                 365
Ser Glu Met Arg Ala Phe Met Glu Val Leu Glu Phe Pro Leu Leu
                    370                 375                 380
Asp Gly Tyr Gly Ser Thr Glu Ala Leu Gly Val Met Arg Asn Gly Ile
385                 390                 395                 400
Ile Gln Arg Pro Pro Val Ile Asp Tyr Lys Leu Val Asp Val Pro Glu
                    405                 410                 415
Leu Gly Tyr Arg Thr Thr Asp Lys Pro Tyr Pro Arg Gly Glu Leu Cys
                    420                 425                 430
Ile Arg Ser Thr Ser Leu Ile Ser Gly Tyr Tyr Lys Arg Pro Glu Ile
                    435                 440                 445
Thr Ala Glu Val Phe Asp Ala Gln Gly Tyr Tyr Lys Thr Gly Asp Val
                    450                 455                 460
Met Ala Glu Ile Ala Pro Asp His Leu Val Tyr Val Asp Arg Ser Lys
465                 470                 475                 480
Asn Val Leu Lys Leu Ser Gln Gly Glu Phe Val Ala Val Ala Lys Leu
                    485                 490                 495
Glu Ala Ala Tyr Gly Thr Ser Pro Tyr Val Lys Gln Ile Phe Val Tyr
                    500                 505                 510
Gly Asn Ser Glu Arg Ser Phe Leu Leu Ala Val Val Pro Asn Ala
                    515                 520                 525
Glu Val Leu Gly Ala Arg Asp Gln Glu Glu Ala Lys Pro Leu Ile Ala
                    530                 535                 540
Ala Ser Leu Gln Lys Ile Ala Lys Glu Ala Gly Leu Gln Ser Tyr Glu
545                 550                 555                 560
Val Pro Arg Asp Phe Leu Ile Glu Thr Glu Pro Phe Thr Thr Gln Asn
                    565                 570                 575
Gly Leu Leu Ser Glu Val Gly Lys Leu Leu Arg Pro Lys Leu Lys Ala
                    580                 585                 590
Arg Tyr Gly Glu Ala Leu Glu Ala Arg Tyr Asp Glu Ile Ala His Gly
                    595                 600                 605
Gln Ala Asp Glu Leu Arg Ala Leu Arg Asp Leu Ala Gly Gln Arg Pro
                    610                 615                 620
Val Val Glu Thr Val Val Arg Ala Ala Val Ala Ile Ser Gly Ser Glu
625                 630                 635                 640
Gly Ala Glu Val Gly Pro Glu Ala Asn Phe Ala Asp Leu Gly Gly Asp
                    645                 650                 655
Ser Leu Ser Ala Leu Ser Leu Ala Asn Leu Leu His Asp Val Phe Glu
                    660                 665                 670
Val Glu Val Pro Val Arg Ile Ile Gly Pro Thr Ala Ser Leu Ala
                    675                 680                 685
Gly Ile Ala Arg His Ile Glu Ala Glu Arg Ala Gly Ser Ala Pro
                    690                 695                 700
Thr Ala Ala Ser Val His Gly Ala Gly Ala Thr Arg Ile Arg Ala Ser
705                 710                 715                 720
Glu Leu Thr Leu Glu Lys Phe Leu Pro Glu Asp Leu Leu Ala Ala Ala
                    725                 730                 735
```

Lys Gly Leu Pro Ala Ala Asp Gln Val Arg Thr Val Leu Leu Thr Gly
                740                 745                 750

Ala Asn Gly Trp Leu Gly Arg Phe Leu Ala Leu Glu Gln Leu Glu Arg
            755                 760                 765

Leu Ala Arg Ser Gly Gln Asp Gly Gly Lys Leu Ile Cys Leu Val Arg
770                 775                 780

Gly Lys Asp Ala Ala Ala Arg Arg Arg Ile Glu Glu Thr Leu Gly
785                 790                 795                 800

Thr Asp Pro Ala Leu Ala Ala Arg Phe Ala Glu Leu Ala Glu Gly Arg
                805                 810                 815

Leu Glu Val Val Pro Gly Asp Val Gly Glu Pro Lys Phe Gly Leu Asp
            820                 825                 830

Asp Ala Ala Trp Asp Arg Leu Ala Glu Glu Val Asp Val Ile Val His
            835                 840                 845

Pro Ala Ala Leu Val Asn His Val Leu Pro Tyr His Gln Leu Phe Gly
850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
                885                 890                 895

Val Glu Pro Ser Ser Phe Glu Glu Asp Gly Asp Ile Arg Ala Val Val
            900                 905                 910

Pro Glu Arg Pro Leu Gly Asp Gly Tyr Ala Asn Gly Tyr Gly Asn Ser
            915                 920                 925

Lys Trp Ala Gly Glu Val Leu Leu Arg Glu Ala Glu Leu Val Gly
            930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
                965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
            995                 1000                1005

Phe Thr Ala Glu Ala Ile Thr Thr Leu Gly Ala Glu Pro Ser Trp
    1010                1015                1020

Phe Asp Gly Gly Ala Gly Phe Arg Ser Phe Asp Val Phe Asn Pro
    1025                1030                1035

His His Asp Gly Val Gly Leu Asp Glu Phe Val Asp Trp Leu Ile
    1040                1045                1050

Glu Ala Gly His Pro Ile Ser Arg Ile Asp Asp His Lys Glu Trp
    1055                1060                1065

Phe Ala Arg Phe Glu Thr Ala Val Arg Gly Leu Pro Glu Ala Gln
    1070                1075                1080

Arg Gln His Ser Leu Leu Pro Leu Leu Arg Ala Tyr Ser Phe Pro
    1085                1090                1095

His Pro Pro Val Asp Gly Ser Val Tyr Pro Thr Gly Lys Phe Gln
    1100                1105                1110

Gly Ala Val Lys Ala Ala Gln Val Gly Ser Asp His Asp Val Pro
    1115                1120                1125

His Leu Gly Lys Ala Leu Ile Val Lys Tyr Ala Asp Asp Leu Lys
    1130                1135                1140

Ala Leu  Gly Leu Leu
    1145

<210> SEQ ID NO 11
<211> LENGTH: 3447
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | |
|---|---|
| atgggctctg gagcggatcg cgcgaagctg ttctttcaga aaattgaaga actgactgca | 60 |
| gcggacccac aatttgcagc agccgtgccc gatcaggaag tggtggccgc cgtaagcgac | 120 |
| ccaactctgt cgtttacccg ttatctcgat accctgatgc gtggctatgc ggatcgtccg | 180 |
| gcactggcgc atcgcgttgg tgacggttat gcgaccatct cttacgggga actgtggtca | 240 |
| cgcgttggag cgattgctgc agcctggagc gcggatggac tggagccggg tgattttgtg | 300 |
| gctacgattg ggttcactag tccggactat accgccctgg atctggcagc gacccgttcc | 360 |
| gggctcgtta gcgttccgct gcaggcgggc gctagtgtgg cgcagctgtc ggcgatcctg | 420 |
| gaggaaacag cccctaaagt tttcgcagcg agcgccgaaa gcctgaaggg tgctgtggat | 480 |
| tgcgttttgc gcaccccgag tgtgcagcgc ctggtcattt cgacttacg ggatgatagc | 540 |
| cctgagcatc gcgctgcctt agcggctgca aaagcgaaac ttgctcagcc gcagaatccc | 600 |
| gaacaggccc gcgggccggt agcggtagag acactggatg aactggttgc tcgtggtgcg | 660 |
| gcacttccgg aacctcctgt ctttgaacca gcggaaggtg aagatccgct ggccctcctg | 720 |
| atctacacca gcggttccac cggcacgccg aaaggggcaa tgtactcgca gcgccttgta | 780 |
| tctcgcttct ggccccgcac gccggtcgtt gcgcagctgc catccatctc acttcactac | 840 |
| atgccgctta gccacagcta tggccgtgcc gtgctgtgtg gcaccctggc ggctggtggt | 900 |
| acagcgcact ttacggctca tagcgatctg tccacgctgt ttgaagatat tgccctcgca | 960 |
| cgcccgacgt ttctggcact ggtcccgcgt atgtgcgaaa tgctgctcca cgagtcgcgc | 1020 |
| cgcgcgcgtg acttagcaga actgcgcgaa cgggttttgg gtgaacgcct gctcgtggcg | 1080 |
| gtttgtggta gtgcgcctct tgcgccagaa cccgcgcgt ttatggaaga gctgctgggc | 1140 |
| tttccactgc tggatggcta tggctcaacc gaagcgttga gcctgatgcg cgatggcgtg | 1200 |
| attcagcgtc ctccggtaat tgactacaaa ttggtggacg tcccggaact gggttacttt | 1260 |
| accaccgata aaccgcatcc ccgtggcgaa ctgttgattc gctctgaatc tcttgtaagc | 1320 |
| ggttactata acgtccaga agaaacagcg gagatgttcg atgagcaagg ttactacaag | 1380 |
| accggcgatg taatgccga aattgccccg gaccgcctgg tctacgttga ccgctccaag | 1440 |
| aacgtcctga actgtcgca aggggaattt gttgccgtgg caaaattgga ggccgcattc | 1500 |
| ggcgcaagcc cgtatgtcaa gcagattttc gtctatggta acagtgaacg ctcttttctg | 1560 |
| cttgcagtag tcgtaccaaa cgccgaatta gtgggccgtc ttgacacagt tcaagccctg | 1620 |
| gccgaagtca aacccttaat cgcagatagt ttagcggcta ttgcgaaaga aagcggcttg | 1680 |
| caatcctatg aagtcccgcg cgactttatc gttgaaaccg agccgtttac gacgggcaat | 1740 |
| ggcctgcttt ctgaagttgg caaactcctg cggcccaaac tcaaggaacg ttacggtgag | 1800 |
| cgcctggagg cgctgtacga tcagattgca cagggccaag ctgacgagtt gcgtgcattg | 1860 |
| cgtgaacagg cgggcgaacg cccagtgatc gatacggtgc gcaaagccgc tgccgcggtg | 1920 |
| gtggggtcat caggggccga ttttcgccca gatgctaatt tcgcagatct gggaggtgat | 1980 |

```
agcctgtcag cgctggggtt cgccaattta ctgcaagatg tgttcggcgt tgaaactccg    2040
gtccggatca ttattggacc tactgcgagt ctggcgggca ttgccgaaca tatcgaacgc    2100
gctttaggcg gtcgccctgg cgaagcggca ccaaattcgg caagtgtgca tggcgcgggt    2160
gcagaagtaa tccgcgcatc tgacctgacg ttagacaaat tcttggacgc tcaagcctta    2220
gaagccgcgc agtcgttacc acgtccgaca ggcagccatc ggacggtcct gttgactgga    2280
gcgaatggat ggttagggcg cttcctggcg ctcgagcagt gcagcgcctt agaagccacg    2340
ggcggaaaac tgatctgctt agtgcgcggt aaagacgcag cgtcagcgcg tgcacgcgtg    2400
gaggaagcgc tgggcaccga tcccgcatta gcagcgcgct tgccgagct ggccgcagat    2460
cgtctggaag ttgttccggg tgacgtgggc gaaccgaagt tcggtctgga cgatcgcacg    2520
tgggatcggc tggctggtga ggtagatgcg gtagtccatt ctggcgcgct ggttaaccac    2580
gttttgccct atcaccagct gttcggcagt aacgtggtgg gcgtggcaga aatcatccgt    2640
ttcgctgtgg cctctaaact aaaccggtg gcctatctct ccactgttgc tgtggctgcg    2700
ggcgccgatc ctgccgcgtt tgatgaagat ggtgacattc gggaggtagt gccgcaacgc    2760
ccggtcgatg actcgtatgc caacggctat ggcaacagca gtgggcggg tgaggtgctg    2820
ttacgcgaag cacacgaacg taccgggctg ccggtgcgtg tctttcgcag tgacatgatt    2880
ctggcccatc gccaacacac cggccagctc aatgcgaccg accagtttac ccgtctgatt    2940
ctgtccttac tggctactgg tttggctcca aaatcgttct atcagttaga tccgcaaggt    3000
cgtcgccagc gtgcacatta cgacggtatt ccggtcgatt ttacggctga ggcgatcgtt    3060
gcccttgccg ccgagggaaa taatgggcac cgttcctata acgtctttaa cccgcaccat    3120
gatggggttg ggctggacga gtttgtggat tggctgatcg aagccggtca tccgattacc    3180
cgcattgagg atcacgccac atggttcgcc cgttttacca ctgcgctgcg ggcgcttcct    3240
gagaaacaac gccagttgtc gttgctccct ctggctcagg tgtatagctt tccccatccg    3300
gcggttgatg gatccccgtt ccgtaacgca gtatttcgtg cggacgtgca acgtgcgcgt    3360
attggtaaag atcatgatat tccgcatctc acccgtgaac tgatcctgaa atatgctgcc    3420
gatctggccg ctctcggctc actttaa                                        3447
```

<210> SEQ ID NO 12
<211> LENGTH: 1148
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Met Gly Ser Gly Ala Asp Arg Ala Lys Leu Phe Phe Gln Lys Ile Glu
1               5                   10                  15

Glu Leu Thr Ala Ala Asp Pro Gln Phe Ala Ala Val Pro Asp Gln
            20                  25                  30

Glu Val Val Ala Ala Val Ser Asp Pro Thr Leu Ser Phe Thr Arg Tyr
        35                  40                  45

Leu Asp Thr Leu Met Arg Gly Tyr Ala Asp Arg Pro Ala Leu Ala His
    50                  55                  60

Arg Val Gly Asp Gly Tyr Ala Thr Ile Ser Tyr Gly Glu Leu Trp Ser
65                  70                  75                  80

Arg Val Gly Ala Ile Ala Ala Ala Trp Ser Ala Asp Gly Leu Glu Pro
                85                  90                  95

```
Gly Asp Phe Val Ala Thr Ile Gly Phe Thr Ser Pro Asp Tyr Thr Ala
                100                 105                 110

Leu Asp Leu Ala Ala Thr Arg Ser Gly Leu Val Ser Val Pro Leu Gln
            115                 120                 125

Ala Gly Ala Ser Val Ala Gln Leu Ser Ala Ile Leu Glu Glu Thr Ala
        130                 135                 140

Pro Lys Val Phe Ala Ala Ser Ala Glu Ser Leu Glu Gly Ala Val Asp
145                 150                 155                 160

Cys Val Leu Arg Thr Pro Ser Val Gln Arg Leu Val Ile Phe Asp Leu
                165                 170                 175

Arg Asp Asp Ser Pro Glu His Arg Ala Ala Leu Ala Ala Ala Lys Ala
            180                 185                 190

Lys Leu Ala Gln Pro Gln Asn Pro Glu Gln Ala Arg Gly Pro Val Ala
        195                 200                 205

Val Glu Thr Leu Asp Glu Leu Val Ala Arg Gly Ala Ala Leu Pro Glu
    210                 215                 220

Pro Pro Val Phe Glu Pro Ala Glu Gly Glu Asp Pro Leu Ala Leu Leu
225                 230                 235                 240

Ile Tyr Thr Ser Gly Ser Thr Gly Thr Pro Lys Gly Ala Met Tyr Ser
                245                 250                 255

Gln Arg Leu Val Ser Arg Phe Trp Pro Arg Thr Pro Val Val Ala Gln
            260                 265                 270

Leu Pro Ser Ile Ser Leu His Tyr Met Pro Leu Ser His Ser Tyr Gly
        275                 280                 285

Arg Ala Val Leu Cys Gly Thr Leu Ala Ala Gly Gly Thr Ala His Phe
    290                 295                 300

Thr Ala His Ser Asp Leu Ser Thr Leu Phe Glu Asp Ile Ala Leu Ala
305                 310                 315                 320

Arg Pro Thr Phe Leu Ala Leu Val Pro Arg Met Cys Glu Met Leu Leu
                325                 330                 335

His Glu Ser Arg Arg Ala Arg Asp Leu Ala Glu Leu Arg Glu Arg Val
            340                 345                 350

Leu Gly Glu Arg Leu Leu Val Ala Val Cys Gly Ser Ala Pro Leu Ala
        355                 360                 365

Pro Glu Thr Arg Ala Phe Met Glu Glu Leu Leu Gly Phe Pro Leu Leu
    370                 375                 380

Asp Gly Tyr Gly Ser Thr Glu Ala Leu Ser Leu Met Arg Asp Gly Val
385                 390                 395                 400

Ile Gln Arg Pro Pro Val Ile Asp Tyr Lys Leu Val Asp Val Pro Glu
                405                 410                 415

Leu Gly Tyr Phe Thr Thr Asp Lys Pro His Pro Arg Gly Glu Leu Leu
            420                 425                 430

Ile Arg Ser Glu Ser Leu Val Ser Gly Tyr Tyr Lys Arg Pro Glu Glu
        435                 440                 445

Thr Ala Glu Met Phe Asp Glu Gln Gly Tyr Tyr Lys Thr Gly Asp Val
    450                 455                 460

Met Ala Glu Ile Ala Pro Asp Arg Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Phe Gly Ala Ser Pro Tyr Val Lys Gln Ile Phe Val Tyr
            500                 505                 510
```

```
Gly Asn Ser Glu Arg Ser Phe Leu Ala Val Val Pro Asn Ala
            515                 520                 525

Glu Leu Val Gly Arg Leu Asp Thr Val Gln Ala Leu Ala Glu Val Lys
530                 535                 540

Pro Leu Ile Ala Asp Ser Leu Ala Ala Ile Ala Lys Glu Ser Gly Leu
545                 550                 555                 560

Gln Ser Tyr Glu Val Pro Arg Asp Phe Ile Val Glu Thr Glu Pro Phe
                565                 570                 575

Thr Thr Gly Asn Gly Leu Leu Ser Glu Val Gly Lys Leu Leu Arg Pro
                580                 585                 590

Lys Leu Lys Glu Arg Tyr Gly Glu Arg Leu Glu Ala Leu Tyr Asp Gln
            595                 600                 605

Ile Ala Gln Gly Gln Ala Asp Glu Leu Arg Ala Leu Arg Glu Gln Ala
            610                 615                 620

Gly Glu Arg Pro Val Ile Asp Thr Val Arg Lys Ala Ala Ala Ala Val
625                 630                 635                 640

Val Gly Ser Ser Gly Ala Asp Phe Arg Pro Asp Ala Asn Phe Ala Asp
                645                 650                 655

Leu Gly Gly Asp Ser Leu Ser Ala Leu Gly Phe Ala Asn Leu Leu Gln
                660                 665                 670

Asp Val Phe Gly Val Glu Thr Pro Val Arg Ile Ile Gly Pro Thr
            675                 680                 685

Ala Ser Leu Ala Gly Ile Ala Glu His Ile Glu Arg Ala Leu Gly Gly
            690                 695                 700

Arg Pro Gly Glu Ala Ala Pro Asn Ser Ala Ser Val His Gly Ala Gly
705                 710                 715                 720

Ala Glu Val Ile Arg Ala Ser Asp Leu Thr Leu Asp Lys Phe Leu Asp
                725                 730                 735

Ala Gln Ala Leu Glu Ala Ala Gln Ser Leu Pro Arg Pro Thr Gly Ser
            740                 745                 750

His Arg Thr Val Leu Leu Thr Gly Ala Asn Gly Trp Leu Gly Arg Phe
            755                 760                 765

Leu Ala Leu Glu Gln Leu Gln Arg Leu Glu Ala Thr Gly Gly Lys Leu
770                 775                 780

Ile Cys Leu Val Arg Gly Lys Asp Ala Ala Ser Ala Arg Ala Arg Val
785                 790                 795                 800

Glu Glu Ala Leu Gly Thr Asp Pro Ala Leu Ala Ala Arg Phe Ala Glu
                805                 810                 815

Leu Ala Ala Asp Arg Leu Glu Val Val Pro Gly Asp Val Gly Glu Pro
                820                 825                 830

Lys Phe Gly Leu Asp Asp Arg Thr Trp Asp Arg Leu Ala Gly Glu Val
            835                 840                 845

Asp Ala Val His Ser Gly Ala Leu Val Asn His Val Leu Pro Tyr
850                 855                 860

His Gln Leu Phe Gly Ser Asn Val Val Gly Val Ala Glu Ile Ile Arg
865                 870                 875                 880

Phe Ala Val Ala Ser Lys Leu Lys Pro Val Ala Tyr Leu Ser Thr Val
                885                 890                 895

Ala Val Ala Ala Gly Ala Asp Pro Ala Ala Phe Asp Glu Asp Gly Asp
                900                 905                 910

Ile Arg Glu Val Val Pro Gln Arg Pro Val Asp Asp Ser Tyr Ala Asn
            915                 920                 925

Gly Tyr Gly Asn Ser Lys Trp Ala Gly Glu Val Leu Leu Arg Glu Ala
```

```
                930              935              940
His Glu Arg Thr Gly Leu Pro Val Arg Val Phe Arg Ser Asp Met Ile
945                  950                  955                  960

Leu Ala His Arg Gln His Thr Gly Gln Leu Asn Ala Thr Asp Gln Phe
                 965                  970                  975

Thr Arg Leu Ile Leu Ser Leu Leu Ala Thr Gly Leu Ala Pro Lys Ser
             980                  985                  990

Phe Tyr Gln Leu Asp Pro Gln Gly Arg Arg Gln Arg Ala His Tyr Asp
         995                 1000                 1005

Gly Ile Pro Val Asp Phe Thr Ala Glu Ala Ile Val  Ala Leu Ala
        1010                1015                1020

Ala Glu Gly Asn Asn Gly His Arg Ser Tyr Asn Val Phe Asn Pro
    1025                1030                1035

His His Asp Gly Val Gly Leu Asp Glu Phe Val Asp  Trp Leu Ile
     1040                1045                1050

Glu Ala Gly His Pro Ile Thr Arg Ile Glu Asp His Ala Thr Trp
     1055                1060                1065

Phe Ala Arg Phe Thr Thr Ala Leu Arg Ala Leu Pro Glu Lys Gln
    1070                1075                1080

Arg Gln Leu Ser Leu Leu Pro Leu Ala Gln Val Tyr Ser Phe Pro
    1085                1090                1095

His Pro Ala Val Asp Gly Ser Pro Phe Arg Asn Ala Val Phe Arg
    1100                1105                1110

Ala Asp Val Gln Arg Ala Arg Ile Gly Lys Asp His Asp Ile Pro
    1115                1120                1125

His Leu Thr Arg Glu Leu Ile Leu Lys Tyr Ala Ala Asp Leu Ala
    1130                1135                1140

Ala Leu Gly Ser Leu
    1145
```

POLYPEPTIDES AND VARIANTS HAVING IMPROVED ACTIVITY, MATERIALS AND PROCESSES RELATING THERETO

CROSS-REFERENCE

This application claims the benefit of U.S. Provisional Application No. 62/309,689, filed Mar. 17, 2016, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Mar. 13, 2017, is named 12444_0652-00000_SL.txt and is 87,964 bytes in size.

TECHNICAL FIELD

The disclosure relates to polypeptides having carboxylic acid reductase (CAR) activity, including enzymes that catalyse the irreversible reduction of carboxylic acids, such as pimelic acid and adipic acid, to their respective semialdehydes. The enzymes have been engineered to have higher activity over a corresponding wild type enzyme.

BACKGROUND

Carboxylic acid reductase (CAR) enzymes belong to the family of oxidoreductases and are specifically categorized under EC 1.2.99.6. They functionally catalyse the reduction of a carboxylic acid (e.g., adipic acid, pimelic acid) to its respective aldehyde, and later alcohols.

Based on sequence homology, each of the known CAR enzymes (EC 1.2.99.6) are composed of two large functional domains, namely an N-terminal Adenylate/AMP/ATP-binding domain and a C-terminal NAD(P)-binding domain, also known as the reductase domain (FIG. 2). The AMP- and the NAD-binding domains enclose a phosphopantetheine attachment site (PP-site) that harbours the phosphopantetheine cofactor which is added post-translationally by a phosphopantetheine transferase (pptase). Catalysis of a carboxylic acid to an aldehyde is postulated to occur by a sequential catalytic mechanism wherein the N-terminal domain catalyzes substrate activation by formation of an initial acyl-AMP intermediate. The intermediate then reacts with the thiol moiety of the phosphopantetheine cofactor to generate a covalently bound thioester. The phosphopantetheine cofactor serves as an arm that swings to the C-terminal reductase domain, which then catalyzes the reduction of the intermediate thioester formed from Acyl-AMP to finish a catalytic cycle. Further analysis of the conserved domain structure by BLAST confirmed the classification of the N-terminal large domain to the Adenylate forming domain (AFD) Class I superfamily, which includes the phosphopantetheine binding site, and the C-terminal large domain belonging to the NAD(P)H/NAD(P)(+) binding superfamily.

In the context of biosynthetic manufacture of nylon intermediates, the requirement for CAR enzyme activity was identified as a rate-limiting step towards the end of the biosynthetic pathway. Therefore, CAR enzymes were selected as candidates for enzyme engineering studies to improve their activity levels.

SUMMARY

Certain embodiments of the present disclosure are summarized in the following paragraphs. This list is only exemplary and not exhaustive of all of the embodiments provided by this disclosure.

Embodiment 1

A polypeptide comprising, consisting; or consisting essentially of a mutant of SEQ ID NO:1, wherein the polypeptide comprises at least one of the following individual mutations:

P369S/G/V, S284A/G/T, G380D/E, G619Y/F/L, K692R, A894G/V, A892G/V/S, P849G, A880V, 0781V/A/S, or combinations thereof.

Embodiment 2

The polypeptide of embodiment 1, wherein the polypeptide comprises, consists, or consists essentially of a variant of SEQ ID NO:1 chosen from the following variants:
P369S G380E G619L K692R (SEQ ID NO:10);
S284G P369V G619Y;
E220K S284A P369S G380E K692R;
P369S G380E G619L;
K692R P849G A892G A894V;
C781V A892G A894V;
K692R P849G A894G;
S284G P369V G619Y K692R P849G A892G A894V;
S284G P369V G619Y C781V A892G A894V;
S284G P369V G619Y K692R P849G A894G;
S284G P369V G619Y K692R;
S284A P369S G380E K692R P849G A892G A894V;
S284A P369S G380E C781V A892G A894V;
S284A P369S G380E K692R P849G A894G;
P369S G380E G619L K692R P849G A892G A894V; and
P369S G380E G619L C781V A892G A894V.

Embodiment 3

The polypeptide according to any one of embodiments 1 and 2, comprising, consisting, or consisting essentially of a sequence that is at least 70%, at least 80%, at least 90%, at least 95%, or at least 99% homologous to SEQ ID NO:1.

Embodiment 4

The polypeptide according to any one of embodiments 1 and 2, comprising, consisting, or consisting essentially of a sequence that is at least 70%, at least 80%, at least 90%, at least 95%, or at least 99% identical to SEQ ID NO:1.

Embodiment 5

The polypeptide according to embodiment 1, comprising, consisting, or consisting essentially of a variant of SEQ ID NO:1 selected from:
S284A P369S G380E C781V A892G A894V;
P369S G380E G619L K692R P849G A892G A894V;
P369S G380E G619L C781V A892G A894V; and
P369S G380E G619L K692R.

Embodiment 6

The polypeptide according to embodiment 1, comprising, consisting, or consisting essentially of the P369S G380E G619L K692R variant of SEQ ID NO:1.

Embodiment 7

A polypeptide comprising, consisting, or consisting essentially of a mutant of SEQ ID NO:2, wherein the polypeptide comprises at least one of the following individual mutations:
V331M/L, S284I, M334G/V, L336F, H337D/I/V, E338N, T371F, L379V, L383T/V, G386A, L448E/V, M452I/L, F453A, V474R, V476L, N481D, V491L, A494V, K495V, L520T, E516F/V, G579E/V, L590V, R591G, P592A/G, E596G, D607S, E622W/S, D647G/S, I683Q, I684V, A709H, P711D, T780N/S, P826V, E831I, P832Y, Q866V, G869T, L893V, A902I, L1086A);
and combinations thereof comprising 2, 3, 4, 5, 6, or 7 of the same.

Embodiment 8

A polypeptide comprising, consisting, or consisting essentially of a variant of SEQ ID NO:2 selected from:
V331M L448E (SEQ ID NO: 12);
V331M L448E E516V;
L448E M452I;
L448E V331M;
L448E E516F;
L448E E622W;
P369S G380E Q623L E696R;
V331M L448E E516V E831D;
E516F L448E M452I; and
E516F L520T.

Embodiment 9

The polypeptide according to any one of embodiments 7 and 8, comprising, consisting, or consisting essentially of a sequence that is at least 70%, at least 80%, at least 90%, at least 95%, or at least 99% homologous to SEQ ID NO:2.

Embodiment 10

The polypeptide according to any one of embodiments 7 and 8, comprising, consisting, or consisting essentially of a sequence that is at least 70%, at least 80%, at least 90%, at least 95%, or at least 99% identical to SEQ ID NO:2.

Embodiment 11

The polypeptide according to embodiment 7, comprising, consisting, or consisting essentially of a variant of SEQ ID NO:2 chosen from:
V331M L448E (SEQ ID NO: 12);
V331M L448E E516V; and
E516F L520T.

Embodiment 12

The polypeptide according to embodiment 7, comprising, consisting, or consisting essentially of one or more of the L590V, R591G, P592G, P592A, or E596G mutations, relative to SEQ ID NO:2.

Embodiment 13

The polypeptide according to embodiment 7, comprising, consisting, or consisting essentially of one or more of the I683Q and I684V mutations relative to SEQ ID NO:2.

Embodiment 14

The polypeptide according to embodiment 7, comprising, consisting, or consisting essentially of one or more of the P826V, E831I, or P832Y mutations relative to SEQ ID NO:2.

Embodiment 15

The polypeptide according to embodiment 7, comprising, consisting, or consisting essentially of the Q866V mutation of SEQ ID NO:2, the V331M L448E variant; or the V331M L448E E516V variant.

Embodiment 16

A molecularly engineered polypeptide having the activity of a carboxylic acid reductase classified under EC 1.2.99.6, comprising a first Adenylate/ATP-binding domain, a second PP-binding domain, and a third NADP domain, wherein the polypeptide is a variant of a wild type carboxylic acid reductase classified under EC 1.2.99.6.

Embodiment 17

The polypeptide of embodiment 16, wherein the variant comprises one or more amino acid mutations at (i) one or more amino acid residues in the Adenylate/ATP-binding domain of the carboxylic acid reductase; (ii) one or more amino acid residues in the NADP-binding domain of the carboxylic acid reductase; and/or one or more amino acid residues in the PP-binding domain of the carboxylic acid reductase; preferably in the Adenylate/ATP-binding domain of the carboxylic acid reductase.

Embodiment 18

The polypeptide according to embodiment 17, wherein the wild type carboxylic acid reductase is the polypeptide of SEQ ID NO:1 or 2, and wherein:
(i) the amino acid mutations comprise mutations in one or more of the following regions of SEQ ID NO:1:
the Adenylate/AMP/ATP binding (residues 49 to 620);
the PP binding domain (residues 627 to 694);
and the NAD(P) binding domain (residues 750 to 1014); or
(ii) the amino acid mutations comprise mutations in one or more of the following regions of SEQ ID NO:2:
the Adenylate/AMP/ATP binding domain (residues 49 to 620);
the PP binding domain (residues 631 to 698); the NAD(P) binding domain (residues 758 to 1019).

Embodiment 19

The polypeptide according to embodiment 18, wherein the polypeptide comprises one or more mutations at one or more of the following regions of SEQ ID NO:2:
331-338 (ATP/AMP active site region 1a);
370-386 (ATP/AMP active site region 1b);
448-452 (ATP/AMP active site region 1c);

516-520 (ATP/AMP active site region 1d); and
590-596 (ATP/AMP active site region 1e).

Embodiment 20

The polypeptide according to embodiment 18, wherein the polypeptide comprises one or more mutations at one or more of the following regions of SEQ ID NO:2:
826-832 (NADP active site region 1a); and
866-869 (NADP active site region 1 b).

Embodiment 21

The polypeptide according to embodiment 18, wherein the mutations are selected from a region of the Adenylate/AMP/ATP binding domain encompassing the L590V, R591G, P592G, P592A, and E596G mutations.

Embodiment 22

The polypeptide according to embodiment 18, wherein the mutations are selected from a region of the PP binding domain encompassing the I683Q and I684V mutations.

Embodiment 23

The polypeptide according to embodiment 18, wherein the mutations are selected from a region of the NAD(P) domain encompassing the P826V, E831I, and P832Y mutations.

Embodiment 24

The polypeptide according to embodiment 18, wherein the mutations are selected from a region of the NAD(P) binding domain encompassing the Q866V mutation.

Embodiment 25

The polypeptide according to any one of embodiments 18 to 24, wherein the amino acid sequence of the polypeptide is at least 70%, at least 80%, at least 90%, at least 95%, or at least 99% identical to the amino acid sequence of SEQ ID NO:1.

Embodiment 26

The polypeptide according to any one of embodiments 18 to 24, wherein the amino acid sequence of the polypeptide is at least 70%, at least 80%, at least 90%, at least 95%, or at least 99% sequence identity to the amino acid sequence of SEQ ID NO:2.

Embodiment 27

A method for improving the carboxylic acid reductase activity of a polypeptide, comprising:
obtaining a wild type polypeptide having a carboxylic acid reductase activity;
altering one or more amino acid residues in the wild type polypeptide, and thereby producing an improved polypeptide having improved carboxylic acid reductase activity.

Embodiment 28

The method according to embodiment 27, wherein the wild type polypeptide has an ATP-binding domain, a PP-binding domain, and a NADP domain, and wherein the altering comprises a change in one or more amino acid residues in one or more of these domains, preferably in the ATP-binding domain of the wild type polypeptide.

Embodiment 29

The method according to embodiment 28, wherein the wild type polypeptide is an enzyme classified under EC 1.2.99.6, preferably the enzyme of SEQ ID NO:1 or SEQ ID NO:2.

Embodiment 30

The method according to embodiment 29, further comprising altering one or more amino acid residues in a region of the ATP-binding domain surrounding the ATP-binding site.

Embodiment 31

The method according to any one of embodiments 27-30, wherein said altering is or comprises one or more of the V331M, L448E, and E516V mutations of SEQ ID NO:2.

Embodiment 32

The method according to any one of embodiments 27-30, wherein said altering is or comprises one or more of the V331M and L448E mutations of SEQ ID NO:2.

Embodiment 33

The method of any one of embodiments 27-30, wherein the wild type carboxylic acid reductase is the polypeptide of SEQ ID NO:1 or 2, and wherein the improved polypeptide comprises:
(i) mutations in one or more of the following regions of SEQ ID NO:1:
the Adenylate/AMP/ATP binding (residues 49 to 620);
the PP binding domain (residues 627 to 694);
and the NAD(P) binding domain (residues 750 to 1014); or
(ii) mutations in one or more of the following regions of SEQ ID NO:2:
the Adenylate/AMP/ATP binding domain (residues 49 to 620);
the PP binding domain (residues 631 to 698);
the NAD(P) binding domain (residues 758 to 1019).

Embodiment 34

The method according to embodiment 33, wherein the polypeptide has one or more mutations at one or more of the following regions of SEQ ID NO:2:
331-338 (ATP/AMP active site region 1a);
370-386 (ATP/AMP active site region 1b);
448-452 (ATP/AMP active site region 1c);
516-520 (ATP/AMP active site region 1d); and
590-596 (ATP/AMP active site region 1e).

Embodiment 35

The method of any one of embodiments 27-30, wherein the wild type carboxylic acid reductase is the polypeptide of SEQ ID NO:2, and wherein the improved polypeptide comprises one or more mutations at one or more of the following regions of SEQ ID NO:2:
826-832 (NADP active site region 1a); and
866-869 (NADP active site region 1b).

Embodiment 36

The method according to any one of embodiments 27-30, wherein the improved polypeptide comprises, consists, or consists essentially of the triple mutant V331M L448E E516V or the quadruple mutant V331M L448E E516V E831D of SEQ ID NO:2.

Embodiment 37

The method according to any one of embodiments 27-30, wherein the improved polypeptide comprises, consists, or consists essentially of at least one of the following individual mutations of SEQ ID NO:2:
V331M/L, S284I, M334G/V, L336F, H337D/I/V, E338N, T371F, L379V, L383T/V, G386A, L448E/V, M452I/L, F453A, V474R/G, V476L, N481D, V491L, A494V, K495V, L520T, E516F/V, E574D, G579E/V, L590V, R591G, P592A/G, E596G, L602G, D607S, E622W/S, K635W, D647G/S, I683Q, I684V, A709H, P711D, A737N, T780N/S/L, G781D, P826V, E831I, P832Y, Q866V, G869T, L893V, A902I, L1086A, and combinations thereof.

Embodiment 38

The method according to any one of embodiments 27-30, wherein the improved polypeptide comprises, consists, or consists essentially of a variant of SEQ ID NO:2 selected from:
L448E M452I;
L448E V331M;
L448E E516F;
L448E E622W;
P369S G380E Q623L E696R;
V331M L448E E516V;
V331M L448E E516V E831D;
E516F L448E M452I;
E516F L520T; and
V331M L448E.

Embodiment 39

The method according to any one of embodiments 27-30, wherein the improved polypeptide comprises, consists, or consists essentially of a variant of SEQ ID NO:2 selected from:
V331M L448E (SEQ ID NO: 12);
V331M L448E E516V; and
E516F L520T.

Embodiment 40

The method according to any one of embodiments 27-30, wherein the improved polypeptide comprises, consists, or consists essentially of the variant having one or more of the L590V, R591G, P592G, P592A, or E596G mutations of SEQ ID NO:2.

Embodiment 41

The method according to any one of embodiments 27-30, wherein the improved polypeptide comprises, consists, or consists essentially of the variant having one or both of the I683Q and I684V mutations of SEQ ID NO:2.

Embodiment 42

The method according to any one of embodiments 27-30, wherein the improved polypeptide comprises, consists, or consists essentially of the variant having one or more of the P826V, E831I, or P832Y mutations of SEQ ID NO:2.

Embodiment 43

The method according to any one of embodiments 27-30, wherein the improved polypeptide comprises, consists, or consists essentially of the variant having the Q866V mutation of SEQ ID NO:2.

Embodiment 44

An improved polypeptide or functional derivative thereof of any one of the polypeptides according to any one of embodiments 1-43.

Embodiment 45

An improved polypeptide or functional derivative thereof of any one of the polypeptides according to any one of embodiments 1-43, wherein the improved polypeptide has an increase in carboxylic acid reductase activity of at least 5%, at least 10%, at least 20%, at least 50%, at least 100%, at least 200%, at least 300%, at least 400% or at least 500% relative to the wild type polypeptide.

Embodiment 46

An improved polypeptide or functional derivative thereof of any one of the polypeptides according to any one of embodiments 1-43, wherein the improved polypeptide has an increase in carboxylic acid reductase activity between 10% and 250%, preferably between 100% and 200%, relative to the wild-type polypeptide.

Embodiment 47

The improved polypeptide according to any one of embodiments 45 and 46, wherein the carboxylic acid reductase activity is measured using pimelic acid and/or adipic acid as a substrate.

Embodiment 48

The improved polypeptide according to any one of embodiments 45 and 46, wherein the polypeptide is capable of converting at least one substrate into at least one product at a km less than that of a naturally occurring carboxylic acid reductase classified under EC 1.2.99.6.

Embodiment 49

The improved polypeptide according to according to any one of embodiments 45 and 46, wherein the polypeptide is capable of converting at least one substrate into at least one product at a kcat (s−1) greater than that of a naturally occurring carboxylic acid reductase classified under EC 1.2.99.6.

Embodiment 50

The improved polypeptide according to any one of embodiments 45 and 46, wherein the polypeptide is capable of converting at least one substrate into at least one product at a kcat (s−1) greater than 0.005.

Embodiment 51

The improved polypeptide according to any one of embodiments 45 and 46, wherein said improved polypeptide is capable of converting pimelic acid and adipic acid into pimelate semialdehyde and adipate semialdehyde, respectively, and wherein said polypeptide has a kcat (s−1) greater than that of a naturally occurring carboxylic acid reductase classified under EC 1.2.99.6, optionally wherein the kcat (s−1) is determined by cofactor conversion (NADPH, NADH and ATP) method or measurement of acid elimination or aldehyde accumulation.

Embodiment 52

The improved polypeptide according to any one of embodiments 45-51, wherein the polypeptide comprises at least one substrate engaged in the active site of the ATP-binding domain.

Embodiment 53

The improved polypeptide according embodiment 52, wherein the substrate is pimelic acid or adipic acid, or a derivative thereof.

Embodiment 54

A nucleic acid construct or vector comprising a polynucleotide encoding a polypeptide having carboxylic acid reductase activity, wherein the polynucleotide is operably linked to one or more heterologous control sequences that direct production of the polypeptide and wherein the polypeptide having carboxylic acid reductase activity is chosen from:
  (a) a polypeptide having at least 70% sequence identity to the polypeptide of SEQ ID NO: 1;
  (b) a polypeptide having at least 70% sequence identity to the polypeptide of SEQ ID NO: 2; and
  (c) a polypeptide according to any one of embodiments 1-24 and 44-53.

Embodiment 55

A nucleic acid molecule encoding a polypeptide according to any one of embodiments 1-26 and 44-53.

Embodiment 56

A vector comprising the nucleic acid molecule according to embodiment 55, optionally an expression vector.

Embodiment 57

A metabolically engineered microorganism or a host cell transformed or transduced with the vector according to any one of embodiments 54 and 56.

Embodiment 58

The host cell of embodiment 57, wherein the host cell is a prokaryote.

Embodiment 59

The host cell embodiment 58, wherein the prokaryote is a *Escherichia*; *Clostridia*; *Corynebacteria*; *Cupriavidus*; *Pseudomonas*; *Delftia*; *Bacillus*; *Lactobacillus*; *Lactococcus*; and *Rhodococcus*, or a eukaryote selected from the group consisting of *Aspergillus, Saccharomyces, Pichia, Yarrowia, Issatchenkia, Debaryomyces, Arxula,* and *Kluyveromyces*.

Embodiment 60

The metabolically engineered microorganism of embodiment 57, wherein the microorganism is chosen from a yeast, a fungi, a filamentous fungi, an algae, and a bacteria.

Embodiment 61

The metabolically engineered microorganism of embodiment 60, wherein the bacteria is chosen from the bacterial genus *Escherichia* such as *Escherichia coli*; from the bacterial genus *Clostridia* such as *Clostridium ljungdahlii, Clostridium autoethanogenum* or *Clostridium kluyveri*; from the bacterial genus *Corynebacteria* such as *Corynebacterium glutamicum*; from the bacterial genus *Cupriavidus* such as *Cupriavidus necator* or *Cupriavidus metallidurans*; from the bacterial genus *Pseudomonas* such as *Pseudomonas fluorescens, Pseudomonas putida* or *Pseudomonas oleavorans*; from the bacterial genus *Delftia* such as *Delftia acidovorans*; from the bacterial genus *Bacillus* such as *Bacillus subtillis*; from the bacterial genus *Lactobacillus* such as *Lactobacillus delbrueckii*; or from the bacterial genus *Lactococcus* such as *Lactococcus lactis*.

Embodiment 62

A composition comprising a polypeptide according to any one embodiments 1-26 and 44-53.

Embodiment 63

The composition of embodiment 62, further comprising pimelic acid, adipic acid, or both.

Embodiment 64

A method of producing pimelate semialdehyde by the conversion of pimelic acid to pimelate semialdehyde in the presence of a polypeptide according to any one of embodiments 1-26 and 44-53.

Embodiment 65

A method of producing adipate semialdehyde by the conversion of adipic acid to adipate semialdehyde in the presence of a polypeptide according to any one of embodiments 1-26 and 44-53.

Embodiment 66

A method of producing pimelate semialdehyde from pimelic acid comprising the steps of (i) culturing the host cell according to any one of embodiments 57-59 in a suitable medium; and (ii) recovering the pimelate semialdehyde.

Embodiment 67

A method of producing adipate semialdehyde from adipic acid comprising the steps of (i) culturing the host cell according to any one of embodiments 57-59 in a suitable medium; and (ii) recovering the adipate semialdehyde.

Embodiment 68

A fusion protein comprising the polypeptide according to any one of embodiments 1-26 and 44-53.

Embodiment 69

A method of modifying pimelate semialdehyde and/or adipate semialdehyde biosynthesis in a microorganism, the method comprising introducing into said microorganism an effective amount of the vector according to any one of embodiments 54 and 56, thereby modifying pimelate semialdehyde and/or adipate semialdehyde in the microorganism.

Embodiment 70

A composition comprising pimelic acid and a means for converting the pimelic acid to pimelate semialdehyde.

Embodiment 71

A composition comprising adipic acid and a means for converting the adipic acid to adipate semialdehyde.

Embodiment 72

A method of producing pimelate semialdehyde comprising:
a step for enzymatically converting pimelic acid to pimelate semialdehyde; and
measuring and/or harvesting the pimelate semialdehyde thereby produced.

Embodiment 73

A method of producing adipate semialdehyde comprising:
a step for enzymatically converting adipic acid to adipate semialdehyde; and
measuring and/or harvesting the adipate semialdehyde thereby produced.

Embodiment 74

An apparatus comprising pimelic acid and a means for converting the pimelic acid to pimelate semialdehyde.

Embodiment 75

An apparatus comprising adipic acid and a means for converting the adipic acid to adipate semialdehyde.

Embodiment 76

A composition comprising pimelate semialdehyde and/or adipate semialdehyde and trace amounts of the metabolically engineered microorganism or host cell according to embodiment 57.

Embodiment 77

A bioderived pimelate semialdehyde or adipate semialdehyde that is produced according to the method of any one of embodiments 66 and 67, wherein said bioderived pimelate semialdehyde or adipate semialdehyde optionally has a carbon-12, carbon-13 and carbon-14 isotope ratio that reflects an atmospheric carbon dioxide uptake source.

Embodiment 78

A product comprising a chemical produced from the bioderived pimelate semialdehyde or adipate semialdehyde of embodiment 77, wherein the product comprises a nylon intermediate, a polyester, a pharmaceutical, a biofuel, a fragrance, or a food additive.

Embodiment 79

A bio-derived, bio-based or fermentation-derived product, wherein said product comprises:
i. a composition comprising at least one bio-derived, bio-based or fermentation-derived compound produced in the presence of a polypeptide according to any one of embodiments 1-26 and 44-53, or produced from the product of a reaction catalyzed by a polypeptide according to any one of embodiments 1-26 and 44-53, or any combination thereof,
ii. a bio-derived, bio-based or fermentation-derived polymer comprising the bio-derived, bio-based or fermentation-derived composition or compound of i., or any combination thereof,
iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof,
iv. a molded substance obtained by molding the bio-derived, bio-based or fermentation-derived polymer of ii. or the bio-derived, bio-based or fermentation-derived resin of iii., or any combination thereof,
v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived molded substance of iv, or any combination thereof, or
vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

Embodiment 80

A non-naturally occurring biochemical network comprising at least one substrate of FIG. 1, at least one exogenous nucleic acid encoding a polypeptide having the activity of at least one enzyme of FIG. 1 and at least one product of FIG. 1.

These and other aspects and embodiments of the present disclosure will be apparent from the present description and the drawings.

BRIEF DESCRIPTION OF THE DRAWINGS

The patent or application file contains at least one drawing executed in color. Copies of this patent or patent application publication with color drawings will be provided by the United States Patent and Trademark Office upon request and payment of the necessary fee.

Those of skill in the art will understand that the drawings, described below, are for illustrative purposes only. The drawings are not intended to limit the scope of the present teachings in any way.

FIGS. 3A and 3B: Alignment of native SrugCAR (SEQ ID NO:1) and SrotCAR (SEQ ID NO:8) amino acid sequences. S.rugCAR69 disclosed as SEQ ID NO:10.

FIG. 4: SrotCAR point mutation screening, demonstrating the mutation, Z-factor, and the average slope based upon four replicates.

DETAILED DESCRIPTION

Figure 1:
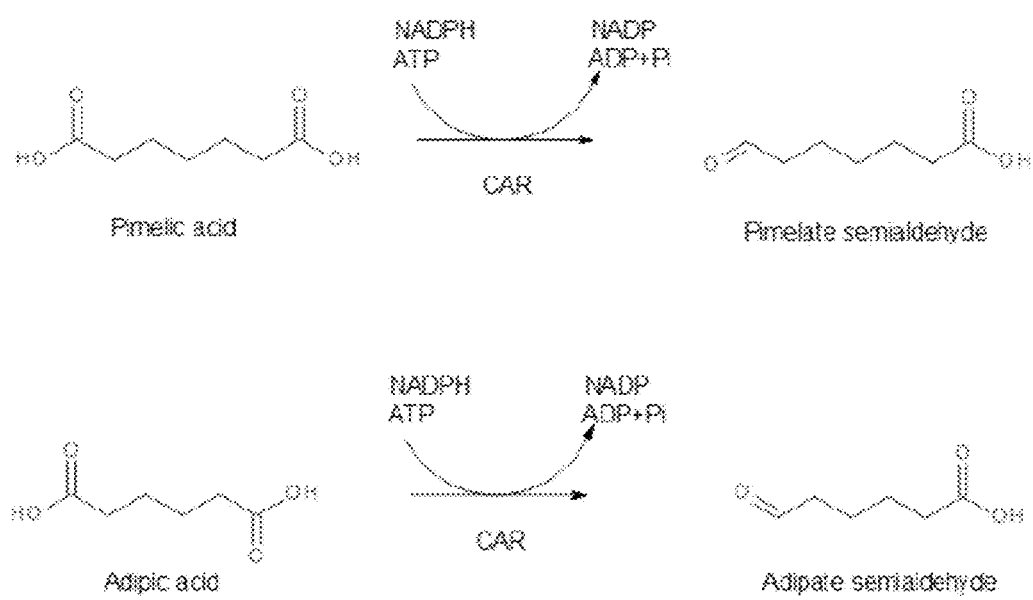
FIG. 1: The proposed catalytic reduction of dicarboxylic acids (Pimelic and Adipic acid) to their respective aldehydes by CAR.
Figure 2:
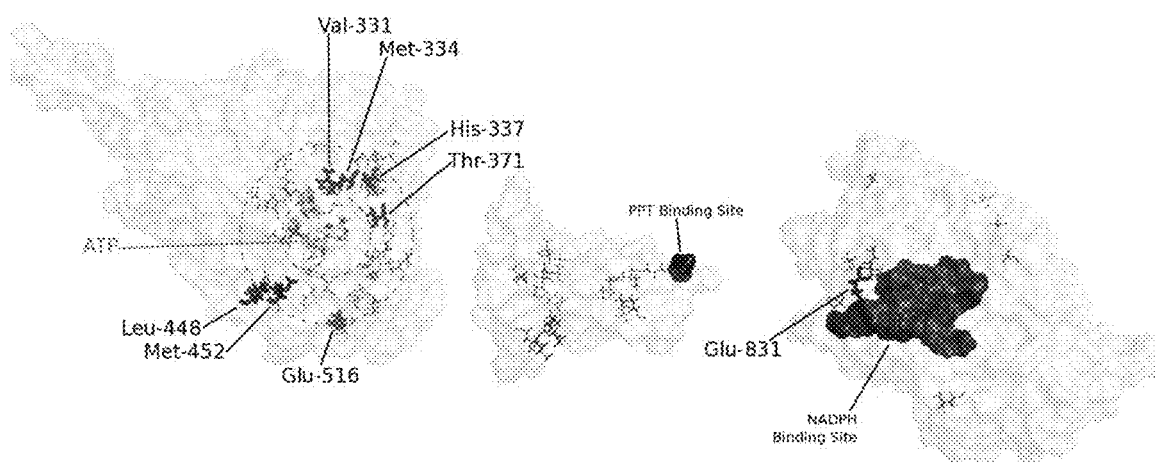
FIG. 2: A composite homology model illustrating relative distribution of positive mutations in SrotCAR. Each of the three major domains was generated independently based upon characterised structures within the public domain.

All references referred to are incorporated herein by reference in their entireties.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In the present description and claims, the conventional one-letter and three-letter codes for amino acid residues are used. For ease of reference, the polypeptides described herein are described by use of the following nomenclature: Original amino acid(s):position(s):substituted amino acid(s) (e.g., V331M, where V is replaced with M at amino acid position 331).

Definitions

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of microbiology, tissue culture, molecular biology, chemistry, biochemistry and recombinant DNA technology, which are within the skill of the art. The materials, methods and examples are illustrative only and not limiting. The following is presented by way of illustration and is not intended to limit the scope of the disclosure.

In some embodiments, numbers expressing quantities of ingredients, properties such as molecular weight, reaction conditions and results, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the specification (into which the claims are incorporated in their entirety) are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

The term "conservatively modified variants" or "conservative mutations" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) J. Gen. Microbiol. 139:425-32) can be modified to yield a functionally identical molecule. Accordingly, each silent variation of a nucleic acid, which encodes a polypeptide of the present disclosure, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds, or deletes a single amino acid or a small percentage of amino acids in the encoded sequence is a "conservatively modified variant" when the alteration results in the substitution of an amino acid with a chemically similar amino acid. Thus, any number of amino acid residues can be so altered. Conservatively modified variants typically provide equivalent biological activity as the unmodified polypeptide sequence from which they are derived. Conservative substitution tables providing possibly functionally similar amino acids, also referred herein as "equivalent amino acids" are well known in the art.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition that "comprises," "has" or "includes" one or more features is not limited to possessing only those one or more features and can cover other unlisted features. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element as essential to the practice of the present disclosure.

As used herein, the term "bioderived" means derived from or synthesized by a biological organism and can be considered a renewable resource since it can be generated by a biological organism. Such a biological organism, in particular the microbial organisms disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

The term "consisting of" refers to compositions, methods, and respective components thereof as described herein, which are exclusive of any element not recited in that description of the embodiment.

As used herein, "consisting essentially of" means the inclusion of additional sequences to an object polynucleotide or polypeptide where the additional sequences do not materially affect the basic function of the claimed polynucleotide or polypeptide sequences. With regard to compositions in general, the term "consisting essentially of" refers to those elements required for a given embodiment and additionally permits the presence of elements that do not materially affect the basic and novel or functional characteristic(s) of that embodiment of the disclosure.

"Codon optimization" is the process of modifying a nucleotide sequence in a manner that improves its expression, G/C content, RNA secondary structure, and translation in eukaryotic cells, without altering the amino acid sequence it encodes. Altered codon usage is often employed to alter translational efficiency and/or to optimize the coding sequence for expression in a desired host or to optimize the codon usage in a heterologous sequence for expression in a particular host. Codon usage in the coding regions of the polynucleotides of the present disclosure can be analyzed statistically using commercially available software packages such as "Codon Preference" available from the University of Wisconsin Genetics Computer Group. See, Devereaux, et al., (1984) Nucleic Acids Res. 12:387-395) or MacVector 4.1 (Eastman Kodak Co., New Haven, Conn.). Thus, the present disclosure provides a codon usage frequency characteristic of the coding region of at least one of the polynucleotides of the present disclosure. The number of polynucleotides (3 nucleotides per amino acid) that can be used to determine a codon usage frequency can be any integer from 3 to the number of polynucleotides of the present disclosure as provided herein. Optionally, the polynucleotides will be full-length sequences. An exemplary number of sequences for statistical analysis can be at least 1, 5, 10, 20, 50 or 100.

The term "derived" encompasses the terms "originated from", "obtained" or "obtainable from", and "isolated from".

"Equivalent amino acids" can be determined either on the basis of their structural homology with the amino acids for which they are substituted or on the results of comparative tests of biological activity between the various variants likely to be generated. As a non-limiting example, the list below summarizes possible substitutions often likely to be carried out without resulting in a significant modification of the biological activity of the corresponding variant:

1) Alanine (A), Serine (S), Threonine (T), Valine (V), Glycine (G), and Proline (P);
2) Aspartic acid (D), Glutamic acid (E);
3) Asparagine (N), Glutamine (Q);
4) Arginine (R), Lysine (K), Histidine (H);
5) Isoleucine (I), Leucine (L), Methionine (M), Valine (V) and
6) Phenylalanine (F), Tyrosine (Y), Tryptophan (W).

See also, Creighton, Proteins, W.H. Freeman and Co. (1984).

In making such changes/substitutions, the hydropathic index of amino acids may also be considered. The importance of the hydropathic amino acid index in conferring interactive biologic function on a protein is generally understood in the art (Kyte and Doolittle, (1982) J Mol Biol. 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In specific embodiments, the substitution is an alanine for the native amino acid at the recited position(s). Also encompassed are the nucleic acid sequence(s) encoding the variant protein or polypeptide.

Enzyme Classification (EC) Numbers: EC numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction catalyzed.

"Endogenous" with reference to a polynucleotide or protein refers to a polynucleotide or protein that occurs naturally in the host cell.

As used herein, "expression" refers to the process by which a polypeptide is produced based on the nucleic acid sequence of a gene. The process includes both transcription and translation.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

Examples of routinely used "expression systems" include recombinant baculovirus, lentivirus, protozoa (e.g., eukaryotic parasite *Leishmania tarentolae*), microbial expression systems, including yeast-based (e.g. *Pichia Pastoris, Saccharomyces cerevisiae, Yaerobia lipolytica, Hansenula polymorpha, Aspergillus* and *Trichoderma Fungi*) and bacterial-based (e.g. *E. Coli, Pseudomonas fluorescens, Lactobacillus, Lactococcus, Bacillus megaterium, Bacillus Subtilis, Brevibacillus, Corynebacterium glutamicum*), Chinese hamster ovary (CHO) cells, CHOK1SVNSO (Lonza), BHK (baby hamster kidney), PerC.6 or Per.C6 (e.g., Percivia, Crucell), different lines of HEK 293, Expi293F™ cells (Life Technologies), GenScript's YeastHIGH™ Technology (GenScript), human neuronal precursor cell line AGE1.HN (Probiogen) and other mammalian cells, plants (e.g., corn, alfalfa, and tobacco), insect cells, avian eggs, algae, and transgenic animals (e.g., mice, rats, goats, sheep, pigs, cows). The advantages and disadvantages of these various systems have been reviewed in the literature and are known to one of ordinary skill in the art.

As used herein, the term "fragment" of a polypeptide refers to a shorter portion of a full-length polypeptide or protein ranging in size from four amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

A "gene" refers to a DNA segment that is involved in producing a polypeptide and includes regions preceding and following the coding regions as well as intervening sequences (introns) between individual coding segments (exons).

"Host strain" or "host cell" means a suitable host for an expression vector or DNA construct comprising a polynucleotide encoding a polypeptide according to the disclosure. Specifically, host strains may be bacterial cells, mammalian cells, insect cells, and other cloning or "expression systems." In an embodiment of the disclosure, "host cell" means both the cells and protoplasts created from the cells of a microbial strain. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Heterologous" with reference to a polynucleotide or protein refers to a polynucleotide or protein/polypeptide that does not naturally occur in the host cell. In some embodiments, the protein is a commercially important industrial protein. It is intended that the term encompass proteins that are encoded by naturally occurring genes, mutated genes, and/or synthetic genes. An "exogenous" polynucleotide or protein can be either heterologous or homologous to the host cell.

A polynucleotide or a polypeptide having a certain percent (e.g., at least 90%, 91%, 92%, 93%, 94%, 95%, 96%, 97%, 98%, or 99%) of "sequence identity" with another sequence means that, when aligned, that percentage of bases or amino acid residues are the same in comparing the two sequences. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution and this process results in "sequence homology" of, e.g, at least 90%, 91%, 92%, 93%, 94%, 95%, 96%, 97%, 98%, or 99%. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA). This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Such programs may include the GCG Pileup program, FASTA (Pearson et al. (1988) Proc. Natl, Acad. Sci USA 85:2444-2448), and BLAST (BLAST Manual, Altschul et al., Nat'l Cent. Biotechnol. Inf., Natl Lib. Med. (NCIB NLM NIH), Bethesda, Md., and Altschul et al., (1997) NAR 25:3389-3402). Another alignment program is ALIGN Plus (Scientific and Educational Software, Pa.), using default parameters. Another sequence software program that finds use is the TFASTA Data Searching Program available in the Sequence Software Package Version 6.0 (Genetics Computer Group, University of Wisconsin, Madison, Wis.).

"Introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, a metabolically engineered microorganism is an organism produced via the introduction of genetic material into a host or parental microorganism of choice thereby modifying or altering the cellular physiology and biochemistry of the microorganism.

As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

The term "nucleic acid" encompasses DNA, cDNA, RNA, heteroduplexes, and synthetic molecules capable of encoding a polypeptide. RNA includes mRNA, RNA, RNAi, siRNA, cRNA and autocatalytic RNA. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. A nucleic acid comprises a nucleotide sequence which typically includes nucleotides that comprise an A, G, C, T or U base. However, nucleotide sequences may include other bases such as, without limitation inosine, methylycytosine, methylinosine, methyladenosine and/or thiouridine, although without limitation thereto.

One skilled in the art will recognize that nucleic acid sequences encompassed by the disclosure are also defined by the ability to hybridize under stringent hybridization conditions with nucleic acid sequences encoding the exemplified polypeptides. A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (Sambrook, et al. (Molecular cloning: a laboratory manual, Cold Spring Harbor Laboratory; 4th edition, 2012). Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10×Denhardt's, 5% dextran sulfate and 1% salmon sperm DNA; (2) primary hybridization for 20 hours at a temperature depending on the length of the probe (i.e.: 42° C. for a probe>100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe >100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001). Stringent conditions may also be achieved with the addition of destabilizing agents such as formamide.

The term "operably linked" and its variants refer to chemical fusion or bonding or association of sufficient stability to withstand conditions encountered in the nucleotide incorporation methods utilized, between a combination of different compounds, molecules or other entities such as, but not limited to: between a mutant polymerase and a reporter moiety (e.g., fluorescent dye or nanoparticle); between a nucleotide and a reporter moiety (e.g., fluorescent dye); or between a promoter and a coding sequence, if it controls the transcription of the sequence.

A "promoter" is a regulatory sequence that is involved in binding RNA polymerase to initiate transcription of a gene. The promoter may be an inducible promoter or a constitutive promoter. An exemplary promoter used herein is a T7 promoter, which is an inducible promoter.

"Recombinant" when used in reference to a cell, nucleic acid, protein or vector, indicates that the cell, nucleic acid, protein or vector, has been modified by the introduction of a "heterologous nucleic acid" or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

As used herein, "transformed cell" includes cells that have been transformed or transduced by use of recombinant DNA techniques. Transformation typically occurs by insertion of one or more nucleotide sequences into a cell. The inserted nucleotide sequence may be a "heterologous nucleotide sequence," i.e., is a sequence that is not natural to the cell that is to be transformed, such as a fusion protein.

As used herein, "transformed", "stably transformed", "transduced," and "transgenic" used in reference to a cell means the cell has a non-native (e.g., heterologous) nucleic acid sequence integrated into its genome or as an episomal plasmid that is maintained through multiple generations.

"Variants" refer to both polypeptides and nucleic acids. The term "variant" may be used interchangeably with the term "mutant." Variants include insertions, substitutions, transversions, truncations, and/or inversions at one or more locations in the amino acid or nucleotide sequence, respectively, of a parent sequence. Variant nucleic acids can include sequences that are complementary to sequences that are capable of hybridizing to the nucleotide sequences presented herein. For example, a variant sequence is complementary to sequences capable of hybridizing under stringent conditions (e.g., 50° C. and 0.2.×SSC (1×SSC=0.15 M NaCl, 0.015 M sodium citrate, pH 7.0)) to the nucleotide sequences presented herein. More particularly, the term variant encompasses sequences that are complementary to sequences that are capable of hybridizing under highly stringent conditions (e.g., 65° C. and 0.1×SSC) to the nucleotide sequences presented herein.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the claimed embodiments are intended to include such other forms of expression vectors, such as viral vectors (e.g., replication defective retroviruses, adenoviruses and adeno-associated viruses), which serve equivalent functions. Vectors also include cloning vectors, shuttle vectors, plasmids, phage particles, cassettes and the like.

Reference will now be made in detail to various disclosed embodiments.

The Car Enzymes

The present disclosure provides mutant or variant CAR enzymes that exhibit improved catalytic activity in reducing carboxylic acids (e.g., pimelic acid and adipic acid) to their respective aldehydes. FIG. 1. It also provides libraries of engineered CAR enzymes comprising one or more mutations in one or more domains, and materials and processes related thereto.

Each of the known CAR enzymes (EC 1.2.99.6) comprises two large functional domains, which are an N-terminal AMP binding domain (also known as ATP/adenylate-binding domain) and a C-terminal NADP(H) binding domain. These two domains enclose a phosphopantetheine attachment site (PP-site) that harbours the phosphopantetheine cofactor, which is added post-translationally by a phosphopantetheine transferase (pptase). A more detailed description of the amino acids encompassed by each domain is provided in the EXAMPLES section.

In this disclosure, each of these CAR domains, alone and in combination, was mutated and the catalytic activity of the resultant mutants assayed for improvement relative to that of their wild-type counterpart. First, two different active CAR proteins were identified by biodiversity screening. Subsequently, each was engineered by targeted sequence mutagenesis. They are the CAR enzyme from *Segniliparus rugosus* (SrugCAR, SrCAR, or SrugCAR-wt; EFV11917) and the CAR enzyme from *Segniliparus rotundus* (SrotCAR, ADG99338). At least the latter protein had not been previously assigned any function, but is herein classified as a CAR enzyme with activity on pimelic and adipic acid.

The Car Variants

Two CAR proteins were engineered to improve on their catalytic activity, relative to that of a wild-type counterpart. These were SrugCAR (SrCAR, or SrugCAR-wt; EFV11917, SEQ ID NO:1 for native protein; SEQ ID NO:3 for native nucleic acid; SEQ ID NO:4 for optimized nucleic acid; SEQ ID NO:7 for optimized protein sequence) and newly characterised SrotCAR (ADG99338 SEQ ID NO:8 for native protein; SEQ ID NO:5 for native nucleic acid; SEQ ID NO:6 for optimized nucleic acid; SEQ ID NO:2 for optimized protein sequence).

For the SrugCAR enzymes disclosed herein, the Adenylate/AMP/ATP-binding domain is hypothesised to be encompassed by residues 49 to 620. The PP-site or domain is hypothesised to be encompassed by residues 627 to 694. And the NAD(P)-binding domain is hypothesised to be encompassed by residues 750 to 1014.

For the SrotCAR enzymes disclosed herein, the Adenylate/AMP/ATP-binding domain is hypothesised to be encompassed by residues 49 to 620. The PP-site or domain is hypothesised to be encompassed by residues 631 to 698. And the NAD(P)-binding domain is hypothesised to be encompassed by residues 758 to 1019.

The catalytic activity was measured with regard to the mutant's ability to reduce carboxylic acids like pimelic acid and adipic acid to their respective semialdehydes. Any other method available to one of ordinary skill in the art can be used to assess this catalytic activity. However, for purpose to this disclosure, the preferred method is that described in the EXAMPLES section of this specification.

The disclosure provides various methods of creating the mutants and libraries disclosed herein. See the EXAMPLES section. However, now that the disclosure provides numerous examples of mutants of interest, any other methods for generating the disclosed mutants, many of which methods are well-known in the art, can be used to generate these mutations.

In total, nearly 10,000 SrotCAR-variants and more than 4100 SrugCAR-variants were generated and screened. It is impractical to list all of the improved variants and call specific attention to each and every one of them when there are numerous identified in this disclosure. That said, one of ordinary skill in the art would understand that the inventors were in possession of each positive variant, because each was tested and each was identified.

SrugCAR Variants

In the first instance, 220 positions within the Adenylate-binding Domain (sublibrary SrugCAR 1.1.), 57 positions within the PP-site (sublibrary SrugCAR 1.2.), and 127 positions within the NAD(P)-binding domain (sublibrary SrugCAR 1.3.), were identified as targets for engineering based on sequence homology to other enzymes. Of the 3,654 theoretical single point mutants, 3,060 were screened.

In some embodiments, the variant SrugCAR enzymes have between about 120-240% of the wild-type catalytic activity, and are chosen from any of the following 10 variants with single point mutations:
Adenylate/ATP/AMP-binding domain variants: P369V, S284D, G380D, G619Y
PP-Site variants: K692R
NAD(P)-binding domain variants: A894G, A892G, P849G, A880V, C781V.

In some embodiments (Srug CAR 2.1. library), the variants comprise mutations in both certain residues of the Adenylate/AMP binding domain (P369V, S284A, G380D, G619Y) crossed with mutations in certain residues of the PP site (K692R). In some embodiments, the mutations in the Adenylate domain are chosen from replacement of any of the P369, S284, G380, and G619 residues with anyone of V,P,G,S; A,S,G,T; D,G,E; or Y,G,F,L, respectively. In some embodiments, each of these single mutants is combined with a mutation of K692 into K692R. In some embodiments, the variant is selected possesses any combination of the above single mutations in any of the permutation described in Table 1.

TABLE 1

SrugCAR2.1 recombination library of permitted mutations

| Domain | Single Mutation from Library 1 | Allowed mutations for recombination in library 2 | Recombination Library |
|---|---|---|---|
| Adenylate forming domain | P369V S284A G380D G619Y | VPGS ASGT DGE YGFL | SrugCAR-2-1 384 mutants |
| PP-Site | K692R | KR | |

In some embodiments (Srug CAR 2.2 library), the variants comprise mutations in both the PP site (K692R) and certain residues of the NAD(P) binding domain (A894G, A892G, P849G, A880V or C781V). See Table 2.

In some embodiments, the mutations in the NAD(P) binding domain are chosen from replacement of any of the A894, A892, P849, A880, C781 residues with anyone of GAV; GAVS; PG; VA; or VCAS, respectively.

In some embodiments, each of these single mutants is combined with a mutation of K692 into K692R. In some embodiments, the variant possesses any combination of the above single mutations in any permutation.

TABLE 2

SrugCAR2.2 recombination library of permitted mutations

| Domain | Single Mutation from Library 1 | Allowed mutations for recombination in library 2 | Recombination Libraries |
|---|---|---|---|
| PP-Site | K692R | KR | SrugCAR-2-2 |
| NAD(P) binding domain | A894G A892G P849G A880V C781V | GAV GAVS PG VA VCAS | 384 mutants |

In some embodiments, the variant is selected from the following SrugCAR mutants:
SrugCAR-31: S284G P369V G619Y
SrugCAR-51: E220K S284A P369S G380E K692R
SrugCAR-52: P369S G380E G619L
SrugCAR-48: K692R P849G A892G A894V
SrugCAR-41: C781V A892G A894V
SrugCAR-54: K692R P849G A894G
SrugCAR-55: K692R In some embodiments, the variant includes multiple combinations of mutations across both recombination libraries:
SrugCAR-50: S284G P369V G619Y K692R P849G A892G A894V
SrugCAR-56: S284G P369V G619Y C781V A892G A894V
SrugCAR-58: S284G P369V G619Y K692R P849G A894G
SrugCAR-59: S284G P369V G619Y K692R
SrugCAR-60: S284A P369S G380E K692R P849G A892G A894V
SrugCAR-61: S284A P369S G380E C781V A892G A894V
SrugCAR-63: S284A P369S G380E K692R P849G A894G
SrugCAR-65: P369S G380E G619L K692R P849G A892G A894V
SrugCAR-66: P369S G380E G619L C781V A892G A894V
SrugCAR-69: P369S G380E G619L K692R In some embodiments, the variant is selected from Srug-CAR-61, SrugCAR-65, SrugCAR-66, and SrugCAR-69.

In some embodiments, the variant is selected from Srug-CAR-65, SrugCAR-66, and SrugCAR-69.

In some embodiments, the variant is selected from Srug-CAR-69 (SEQ ID NO:10 for protein sequence; SEQ ID NO:9 for nucleic acid sequence), the quadruple mutant P369S-G380E-G619L-K692R.

Srot CAR Variants

The newly identified CAR enzyme from *Segniliparus rotundus* (SrotCAR; SEQ ID NO:2) was engineered to improve catalytic activity and expression. All mutations in this section pertain to variations of SEQ ID NO:2. Nevertheless, this disclosure anticipates that, should the same mutations be introduced into native SrotCAR of SEQ ID NO:8 (which differs from SEQ ID NO:2 in only one position, namely S1148 instead of L1148), those mutations will also result in an improved CAR protein. Accordingly, all variants of SEQ ID NO:8 that could be obtained by introducing into SEQ ID NO:8 any of the same mutations that this disclosure suggests for SEQ ID NO:2 also fall within the scope of this disclosure and claims. Accordingly, this disclosure clearly shows that the inventors were in possession of each of those additional embodiments, even if, for practical reasons, they are not explicitly and individually enumerated.

In one embodiment, the corresponding mutations of the quadruple SrugCAR-69 mutant P369S G380E G619L K692R were transferred to codon optimised SrotCAR (nucleic acid sequence is SEQ ID NO:6 and amino acid sequence is SEQ ID NO:2). After sequence alignment of both enzymes (FIGS. 3A and 3B), the corresponding mutations in SrotCAR were identified as P369S-G380E-Q623L-E696R.

In addition, 220 positions within the Adenylating Domain, 57 positions within the PP-domain, and 127 positions within the reductase/NAD(P) binding domain, were identified as targets for engineering. This corresponds to 3,489 possible mutations at 404 positions.

In one embodiment, 4416 different clones were screened using pimelic and adipic acid as substrate. In one embodiment, the variant can be selected from any of the most active primary variants, (single-point, relative to SEQ ID NO:2), as follows V331M/L, S284I, M334G/V, L336F, H337D/I/V, E338N, T371F, L379V, L383T/V, G386A, L448E/V, M452I/L, F453A, V474R, V476L, N481D, V491L, A494V, K495V, L520T, E516F/V, G579E/V, L590V, R591G, P592A/G, E596G, D607S, E622W/S, D647G/S, I683Q, I684V, A709H, P711D, T780N/S, P826V, E831I, P832Y, Q866V, G869T, L893V, A902I, L1086A.

In one embodiment, the variant is selected from the following variants:

E516F/V, L448E/V, M452I, I684V, V331M, and E831I.

In one embodiment, the variant is selected from E516F, L448E, and M452I.

In one embodiment, the variant is E622S or E622W. In one embodiment, the variant is S284I. In one embodiment, the variant is T371F.

In one embodiment, the variant is selected from T371F, L379V, L383V, L383T, and G386A, In another embodiment, the variant is selected from F453A, V474R, V474G, V476L, N481D, V491L, A494V, K495V. In another embodiment, the variant is G579E. In another embodiment, the variant is selected from E622W/S, D647S, and D647G. In another embodiment, the variant is T780S.

In one embodiment, the variant is E516F. In one embodiment, the variant is E516V.

In one embodiment, the variant is selected from S284I, V331M, M334V, H337I, E622W/S, I684V, and G869T In one embodiment, the variant is selected from a hot-spot encompassing V331M, V331L, M334V, M334G, L336F, H337I, H337V, H337D, and E338N.

In one embodiment, the variant is selected from a hot-spot encompassing L448E, L448V, M452I, and M452L.

In another embodiment, the variant is selected from a hot-spot comprising E516F, E516V and L520T.

In another embodiment, the variant is selected from a hot-spot encompassing L590V, R591G, P592G, P592A, and E596G.

In another embodiment, the variant is selected from a hot-spot encompassing I683Q and I684V.

In another embodiment, the variant is selected from a hot-spot encompassing P826V, E831I, and P832Y.

In another embodiment, the variant is selected from a hot-spot encompassing Q866V.

In one embodiment, the variant is selected from the following:

L448E-M452I (mutants having more than one mutation can also be referred to as the "L448 M452I" variant, i.e., without the dash separating the multiple mutations)
E516F-L520T
L448E-V331M
L448E-E516F
L448E-E622W In another embodiment, the variant is L448E. In another embodiment, the variant is V331M-L448E-E516V. In another embodiment, the variant is V331M-L448E-E516V-E831D.

In one embodiment, the variant is selected from E516F-L448E-M452 and E516F-L520T.

In one embodiment, the variant is V331M-L448E (SEQ ID NO:12 for protein sequence; SEQ ID NO:11 for nucleic acid sequence).

Further Mutations in the AMP Binding Domain of SrotCAR:

Several hot-spot positions (i.e., regions enriched in mutations leading to improved enzymatic activity) and individual variants showing increased activity towards adipic and pimelic acid were identified. Most of these positions are within the AMP/Adenylate-binding domain. They appear to be clustered around the binding site for the ATP. Without being bound by any theory, it would appear that the activation and transfer of the carboxylic acid substrate to the phosphopanthetein residue was the rate limiting step. But it is also possible that either the binding of the ATP or substrate or the transfer reaction is rate limiting.

In one embodiment, the CAR mutant comprises a mutation in one or more residues in a region of the ATP-binding domain surrounding the ATP binding site. These residues comprise the following amino acids of SEQ ID NO:2:

331-338 (ATP/AMP active site region 1a)
370-386 (ATP/AMP active site region 1b)
448-452 (ATP/AMP active site region 1c)
516-520 (ATP/AMP active site region 1d)
590-596 (ATP/AMP active site region 1e)

Further Mutations in the PP-Site

Some embodiments provide CAR enzymes having mutations in the PP-site. Some embodiments comprise mutations in the PP-binding region encompassing amino acids 683-684 of SEQ ID NO:2.

Further Mutations in the NAD(P) Binding Domain

Some embodiments provide CAR enzymes having mutations in the following regions of the NAD(P) binding domain, relative to SEQ ID NO:2:

826-832 (NADP active site region 1a)
866-869 (NADP active site region 1b).

In one embodiment, the improved polypeptide has an increase in carboxylic acid reductase activity of at least 5%, at least 10%, at least 20%, at least 50%, at least 100%, at least 200%, at least 300%, at least 400% or at least 500% relative to the activity of the wild type polypeptide. In one embodiment, this activity is specific activity. In this context, "specific activity" is enzymatic activity adjusted for expression levels.

According to another aspect of the present invention, isolated polypeptides (including muteins, allelic variants, fragments, derivatives, and analogs) encoded by the nucleic acid molecules of this disclosure are provided. In one embodiment, the isolated polypeptide comprises the polypeptide sequence corresponding to a polypeptide sequence as disclosed herein. In an alternative embodiment of the present invention, the isolated polypeptide comprises a polypeptide sequence at least 85% identical to a polypeptide sequence disclosed herein. Preferably the isolated polypeptide of the present disclosure has at least 50%, 60, 70%, 80%, 85%, 90%, 95%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or even higher identity to a polypeptide sequence disclosed herein.

According to other embodiments of the present disclosure, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides of the present disclosure also include fusions between the above-described polypeptide sequences and heterologous polypeptides. The heterologous sequences can, for example, include sequences designed to facilitate purification, e.g. histidine tags, and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

The present disclosure also provides antibodies capable of binding to CAR from one or more selected species and mutants. Polyclonal or monoclonal antibodies directed toward part or all of a selected CAR may be prepared according to standard methods. Monoclonal antibodies may be prepared according to general methods of Kohler and Milstein, following standard protocols. In an embodiment, antibodies are prepared, which react immunospecifically with selected epitopes of CAR distinguishing it from other enzymes. The polyclonal or monoclonal antibodies of the disclosure may serve as sensitive detection reagents for the presence and accumulation of the proteins in cultured cells or tissues and in intact organisms Derivatives of the polypeptides disclosed herein are also provided. In one embodiment, derivative polypeptides are polypeptides that have been altered, for example by conjugation or complexing with other chemical moieties, by post-translational modification (e.g. phosphorylation, acetylation and the like), modification of glycosylation (e.g. adding, removing or altering glycosylation), and/or inclusion/substitution of additional amino acid sequences as would be understood in the art.

Additional amino acid sequences may include fusion partner amino acid sequences which create a fusion protein. By way of example, fusion partner amino acid sequences may assist in detection and/or purification of the isolated fusion protein. Non-limiting examples include metal-binding (e.g. poly-histidine) fusion partners, maltose binding protein (MBP), Protein A, glutathione S-transferase (GST), fluorescent protein sequences (e.g. GFP), epitope tags such as myc, FLAG, and haemagglutinin tags.

Other derivatives contemplated by the embodiments include, but are not limited to, modification to side chains, incorporation of unnatural amino acids and/or their derivatives during peptide, or protein synthesis and the use of crosslinkers and other methods which impose conformational constraints on the disclosed polypeptides and fragments thereof.

Expression of the Polypeptides Disclosed Herein

In one embodiment, the polypeptides are expressed according to the methods described in the Examples section of this disclosure. According to some other embodiments, a DNA sequence encoding the polypeptide produced by methods described above, or produced by any alternative methods known in the art, can be expressed, in enzyme form, using an expression vector, which typically includes control sequences encoding a promoter, operator, ribosome binding site, translation initiation signal, and, optionally, a repressor gene or various activator genes. For each combination of a promoter and a host cell, culture conditions are available which are conducive to the expression the DNA sequence encoding the desired polypeptide. After reaching the desired cell density or titre of the polypeptide the culture is stopped and the polypeptide is recovered using known procedures. Alternatively, the host cell is used directly (e.g., pellet, suspension), i.e., without isolation of the recombinant protein.

The recombinant expression vector carrying the DNA sequence encoding a polypeptide as described herein may be any vector, which may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage or an extrachromosomal element, minichromosome, or an artificial chromosome. Alternatively, the vector may be one which, when introduced into a host cell, is integrated into the host cell genome and replicated together with the chromosome(s) into which it has been integrated.

In the vector, the DNA sequence typically is operably connected to a suitable promoter sequence. The promoter may be any DNA sequence that shows transcriptional activity in the host cell of choice and may be derived from genes encoding proteins either homologous or heterologous to the host cell. Examples of suitable promoters for directing the transcription of the DNA sequence encoding a polypeptide as described herein, especially in a bacterial host, are the promoter of the lac operon of *E. coli*, the *Streptomyces coelicolor* agarase gene dagA promoters, the promoters of the *Castellaniella defragrans*, and others. For transcription in a fungal host, examples of useful promoters are those derived from the gene encoding *A. oryzae* TAKA amylase, *Rhizomucor miehei* aspartic proteinase, *A. niger* neutral LDH, *A. niger* acid stable LDH, *A. niger* glucoamylase, *Rhizomucor miehei* lipase, *A. oryzae* alkaline protease, *A. oryzae* triose phosphate isomerase or *A. nidulans* acetamidase. The promoters can be selected based on the desired outcome. The nucleic acids can be combined with constitutive, tissue-preferred, inducible, or other promoters for expression in the host cell or organism. The above list of promoters is not meant to be limiting. Any appropriate promoter can be used in the embodiments.

In some embodiments, the expression vector described may also comprise a suitable transcription terminator and, in eukaryotes, polyadenylation sequences operably connected to the DNA sequence encoding the polypeptide as described herein. Termination and polyadenylation sequences may suitably be derived from the same sources as the promoter or not.

In some embodiments, the vector may further comprise a DNA sequence enabling the vector to replicate in the host cell in question. Examples of such sequences are the origins of replication of plasmids pUC19, pACYC177, pUB110, pE194, pAMB1 and pIJ702. The above list of origins of replication is not meant to be limiting. Any appropriate origins of replication can be used in the embodiments In some embodiments, the vector may also comprise a selectable marker. Selectable marker genes are utilized for the selection of transformed cells or tissues, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation. The above list of selectable marker genes is not meant to be limiting. Any selectable marker gene can be used in the embodiments.

Appropriate culture mediums and conditions for the above-described host cells are known in the art. While intracellular expression may be advantageous in some respects, e.g., when using certain bacteria as host cells, it might be preferred that the expression is extracellular or periplasmic.

Nucleic Acids

With the polypeptides disclosed herein and their amino acid sequence as disclosed herein, the skilled person may determine suitable polynucleotides that encode those polypeptides. Those having ordinary skill in the art will readily appreciate that due to the degeneracy of the genetic code, a multitude of nucleotide sequences encoding the polypeptides described herein exist. The sequence of the polynucleotide gene can be deduced from a polypeptide sequence through use of the genetic code. Computer programs such as "BackTranslate" (GCG™ Package, Acclerys, Inc. San Diego, Calif.) can be used to convert a peptide sequence to the corresponding nucleotide sequence encoding the peptide. Furthermore, synthetic variant polynucleotide sequences encoding the polypeptides as described herein can be designed so that they will be expressed in any cell type, prokaryotic or eukaryotic.

Accordingly, some embodiments relate to polynucleotides either comprising or consisting essentially of a nucleic acid sequence encoding a polypeptide as described above and elsewhere herein. In some embodiments, the nucleic acid sequence is a DNA sequence (e.g., a cDNA sequence). In other embodiments, the nucleic acid sequence is a RNA sequence. In some embodiments, the nucleic acid is a cDNA encoding any of the polypeptides described herein. The nucleotide sequences encoding the polypeptide may be prepared by any suitable technologies well known to those skilled in the art, including, but not limited to, recombinant DNA technology and chemical synthesis. Synthetic polynucleotides may be prepared using commercially available automated polynucleotide synthesizers.

One aspect pertains to isolated or recombinant nucleic acid molecules comprising nucleic acid sequences encoding the polypeptides described herein or biologically active portions thereof, as well as nucleic acid molecules sufficient for use as hybridization probes to identify nucleic acid molecules encoding proteins with regions of sequence homology to the polypeptides described herein. Nucleic acid molecules that are fragments of these nucleic acid sequences encoding polypeptides are also encompassed by the embodiments. By "fragment" is intended a portion of the nucleic acid sequence encoding a portion of a polypeptide. In some embodiments, a fragment of a nucleic acid sequence may encode a biologically active portion of a polypeptide or it may be a fragment that can be used as a hybridization probe or PCR primer using methods well known to one of ordinary skill in the art.

In some embodiments, the nucleic acid has been codon optimized for expression of any one of the polypeptides described herein.

In other embodiments, the nucleic acid is a probe, which may be a single or double-stranded oligonucleotide or polynucleotide, suitably labeled for the purpose of detecting complementary sequences of polynucleotides encoding the polypeptides described herein, such as in arrays, Northern, or Southern blotting. Methods for detecting labeled nucleic acids hybridized to an immobilized nucleic acid are well known to practitioners in the art. Such methods include autoradiography, chemiluminescent, fluorescent and colorimetric detection.

In some embodiments, the polynucleotide comprises a sequence encoding any one of the polypeptides described herein operably linked to a promoter sequence. Constitutive or inducible promoters as known in the art are contemplated herein. The promoters may be either naturally occurring promoters, or hybrid promoters that combine elements of more than one promoter. Non-limiting examples of promoters include SV40, cytomegalovirus (CMV), and HIV-1 LTR promoters.

In some embodiments, the polynucleotide comprises a sequence encoding any one of the polypeptides described herein operably linked to a sequence encoding another protein, which can be a fusion protein or another protein separated by a linker. In some embodiments, the linker has a protease cleavage site, such as for Factor Xa or Thrombin, which allow the relevant protease to partially digest the fusion polypeptide described herein and thereby liberate the recombinant polypeptide therefrom. The liberated polypeptide can then be isolated from the fusion partner by, for example, subsequent chromatographic separation. In some embodiments, the polynucleotide comprises a sequence encoding any one of the polypeptides described herein operably linked to both a promoter and a fusion protein.

Some other embodiments provide genetic constructs in the form of, or comprising genetic components of, a plasmid, bacteriophage, a cosmid, a yeast or bacterial artificial chromosome, as are well understood in the art. Genetic constructs may be suitable for maintenance and propagation of the isolated nucleic acid in bacteria or other host cells, for manipulation by recombinant DNA technology and/or expression (expression vectors) of the nucleic acid or an encoded polypeptide as described herein.

Some other embodiments relate to recombinant expression vectors comprising a DNA sequence encoding one or more of the polypeptides described herein. In some embodiments, the expression vector comprises one or more of said DNA sequences operably linked to a promoter. Suitably, the expression vector comprises the nucleic acid encoding one of the polypeptides described herein operably linked to one or more additional sequences. In some embodiments, the expression vector may be either a self-replicating extra-chromosomal vector such as a plasmid, or a vector that integrates into a host genome. Non-limiting examples of viral expression vectors include adenovirus vectors, adeno-associated virus vectors, herpes viral vectors, retroviral vectors, lentiviral vectors, and the like. For example, adenovirus vectors can be first, second, third, and/or fourth generation adenoviral vectors or gutless adenoviral vectors. Adenovirus vectors can be generated to very high titers of infectious particles, infect a great variety of cells, efficiently transfer genes to cells that are not dividing, and are seldom integrated in the host genome, which avoids the risk of cellular transformation by insertional mutagenesis. The vector may further include sequences flanking the polynucleotide giving rise to RNA which comprise sequences homologous to eukaryotic genomic sequences or viral genomic sequences. This will allow the introduction of the polynucleotides described herein into the genome of a host cell.

An integrative cloning vector may integrate at random or at a predetermined target locus in the chromosome(s) of the host cell into which it is to be integrated.

Specific embodiments of expression vectors are well known in the art and others can be found elsewhere in this disclosure (see below).

In some embodiments, a subject polynucleotide encodes one or more of the mutant polypeptides described herein. In other embodiments, the subject polynucleotide encodes a polypeptide whose amino acid sequence has at least about 85%, at least about 90%, at least about 95%, at least about 98%, or at least about 99%, or greater, amino acid sequence identity to the amino acid sequence of any one of the mutants described herein.

In some embodiments, the polynucleotide encodes a polypeptide with one of the mutations described herein. In other embodiments, the polynucleotide encodes a polypeptide with two or more of the mutations described herein.

The embodiments also encompass nucleic acid molecules encoding relatives of the disclosed polypeptides. "Relatives" of the disclosed polypeptide-encoding nucleic acid sequences include those sequences that encode the polypeptides disclosed herein but that differ conservatively because of the degeneracy of the genetic code. Allelic polypeptides that later develop through culture can be identified with the use of well-known molecular biology techniques, such as polymerase chain reaction (PCR) and hybridization techniques as outlined below. Relative nucleic acid sequences also include synthetically derived nucleic acid sequences that have been generated, for example, by using site-directed mutagenesis but which still encode the polypeptides disclosed.

The skilled artisan will further appreciate that changes can be introduced by mutation of the nucleic acid sequences thereby leading to changes in the amino acid sequence of the encoded polypeptides, without altering the biological activity of the proteins. Thus, relative nucleic acid molecules can be created by introducing one or more nucleotide substitutions, nucleotide additions and/or nucleotide deletions into the corresponding nucleic acid sequence disclosed herein, such that one or more amino acid substitutions, amino acid additions or amino acid deletions are introduced into the encoded protein. Mutations can be introduced by standard techniques, such as site-directed mutagenesis and PCR-mediated mutagenesis. Such relative nucleic acid sequences are also encompassed by the present embodiments.

Alternatively, variant nucleic acid sequences can be made by introducing mutations randomly along all or part of the coding sequence, such as by saturation mutagenesis and the resultant mutants can be screened for ability to confer improved activity or increased specific activity in the catalysis of the reduction of adipic acid and/or pimelic acid to respective aldehydes to identify mutants that retain the improved activity of the polypeptides described herein. Following mutagenesis, the encoded protein can be expressed recombinantly, and the activity of the protein can be determined using standard assay techniques, including those described herein.

Host Cells and Organisms

A subject nucleic acid can be introduced stably or transiently into a host/engineered cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like. Some embodiments relate to host cells comprising an exogenous DNA molecule (i.e., a molecule not otherwise present in the wild-type counterpart cell) encoding a polypeptide as described herein. In some embodiments, these host cells can be described as expression systems. Suitable host cells for expression may be prokaryotic or eukaryotic. Without limitation, suitable host cells may be mammalian cells (e.g. HeLa, HEK293T, Jurkat cells), yeast cells (e.g. *Saccharomyces cerevisiae*), insect cells (e.g. Sf9, *Trichoplusia ni*) utilized with or without a baculovirus expression system, or bacterial cells, such as *E. coli* (Origami2(DE3), BL21 (DE3)), or a Vaccinia virus host. Introduction of genetic constructs into host cells (whether prokaryotic or eukaryotic) is well known in the art, as for example described in Current Protocols in Molecular Biology Eds. Ausubel et al., (John Wiley & Sons, Inc. current update Jul. 2, 2014).

A further embodiment relates to a transformed or transduced organism or microorganism (i.e., an engineered organism), such as an organism selected from plant and insect cells, bacteria, yeast, baculovirus, protozoa, nematodes, algae, and transgenic mammals (e.g., mice, rats, pigs). The microorganisms include prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism. The transformed organism comprises a DNA molecule of the embodiments, an expression cassette comprising the DNA molecule or a vector comprising the expression cassette of the disclosed embodiments, which may be stably incorporated or not stably incorporated into the genome of the transformed organism. Other suitable organisms also include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

In certain embodiments, the host is a prokaryote selected from the group consisting of *Escherichia; Clostridia; Corynebacteria; Cupriavidus; Pseudomonas; Delftia; Bacillus; Lactobacillus; Lactococcus*; and *Rhodococcus*, or a eukaryote selected from the group consisting of *Aspergillus, Saccharomyces, Pichia, Yarrowia, Issatchenkia, Debaryomyces, Arxula*, and *Kluyveromyces*.

In some embodiments, the host microorganism is a prokaryote. For example, the prokaryote can be from the bacterial genus *Escherichia* such as *Escherichia coli*; from the bacterial genus *Clostridia* such as *Clostridium ljungdahlii, Clostridium autoethanogenum* or *Clostridium kluyveri*; from the bacterial genus *Corynebacteria* such as *Corynebacterium glutamicum*; from the bacterial genus *Cupriavidus* such as *Cupriavidus necator* or *Cupriavidus metallidurans*; from the bacterial genus *Pseudomonas* such as *Pseudomonas fluorescens, Pseudomonas putida* or *Pseudomonas oleavorans*; from the bacterial genus *Delftia* such as *Delftia acidovorans*; from the bacterial genus *Bacillus* such as *Bacillus subtillis*; from the bacterial genus *Lactobacillus* such as *Lactobacillus delbrueckii*; or from the bacterial genus *Lactococcus* such as *Lactococcus lactis*.

In some embodiments, the host microorganism is a eukaryote (e.g., a fungus such as a yeast). For example, the eukaryote can be from the fungus genus *Aspergillus* such as *Aspergillus niger*; from the yeast genus *Saccharomyces* such as *Saccharomyces cerevisiae*; from the yeast genus *Pichia* such as *Pichia pastoris*; from the yeast genus *Yarrowia* such as *Yarrowia lipolytica*; from the yeast genus *Issatchenkia* such as *Issathenkia orientalis*; from the yeast genus *Debaryomyces* such as *Debaryomyces hansenii*; from the yeast genus *Arxula* such as *Arxula adenoinivorans*; or from the yeast genus *Kluyveromyces* such as *Kluyveromyces lactis*.

Exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae*,

*Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Another embodiment of the disclosure comprises a method of making a polypeptide of a recombinant gene comprising: a) providing a population of these host cells/organisms; and b) growing the population of cells/organisms under conditions whereby the polypeptide encoded by the coding sequence of the disclosure is expressed; c) isolating the resulting polypeptide.

The host cells can be fermented to produce the mutants described herein or to catalyze the reactions that are catalyzed by the CAR enzymes described herein. Fermentation broadly refers to the conversion of organic materials into target substances by host cells, for example, the conversion of a carbon source by recombinant host cells into fatty acids or derivatives thereof by propagating a culture of the recombinant host cells in a media comprising the carbon source. As used herein, conditions permissive for the production means any conditions that allow a host cell to produce a desired product, such as a fatty acid or a fatty acid derivative. Similarly, conditions in which the polynucleotide sequence of a vector is expressed means any conditions that allow a host cell to synthesize a polypeptide. Suitable conditions include, for example, fermentation conditions. Fermentation conditions can comprise many parameters, including but not limited to temperature ranges, levels of aeration, feed rates and media composition. Each of these conditions, individually and in combination, allows the host cell to grow. Fermentation can be aerobic, anaerobic, or variations thereof (such as micro-aerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source. For small scale production, the engineered host cells can be grown in batches of, for example, about 100 mL, 500 mL, 1 L, 2 L, 5 L, or 10 L; fermented; and induced to express a desired polynucleotide sequence, such as a polynucleotide sequence encoding a CAR polypeptide of the disclosure. For large scale production, the engineered host cells can be grown in batches of about 10 L, 100 L, 1000 L, 10,000 L, 100,000 L, 1,000,000 L or larger; fermented; and induced to express a desired polynucleotide sequence. Alternatively, large scale fed-batch fermentation may be carried out.

Methods of Use

The polypeptides, nucleotides, and cells/organisms described herein are useful as biocatalysts in the production of a variety of products (e.g, synthetic, aromatic, aliphatic and alicyclic aldehydes and alcohols; nylon intermediates; as well as the production of polyesters, pharmaceuticals, biofuels, fragrances, and food additives). In addition, they are useful in the production of specialty chemicals that in their process require the reduction of either ω-difunctional (i. e.—ω-dicarboxylic acids, ω-ester-acids, ω-hydroxy-acids, ω-aminoacids), branched, or aromatic carboxylic acids to their respective aldehydes. Biocatalytic reductions of carboxylic acids are attractive to traditional chemical catalysis at least because the substrates are water soluble, blocking chemistry is not necessary, reductions are enantioselective, and the scope of the reaction is very broad.

The disclosure also provided methods of synthesis of chemical compounds such as those for biocatalytically reducing a carboxylic acid, or a derivative thereof, to its corresponding aldehyde product(s), to provide a method of biocatalytically reducing a carboxylic acid, or a derivative thereof, to its corresponding intermediary by-product(s), as exemplified by acyl-AMP analogs, or to provide a method of biocatalytically reducing adipic and pimilic acid, or a precursor or derivative thereof, all using recombinant CAR as described the disclosure provided herein.

In one embodiment, the disclosure provides for a method of producing pimelate semialdehyde by the conversion of pimelic acid to pimelate semialdehyde in the presence of one or more polypeptides of the disclosure. In one embodiment, the disclosure provides a method of producing adipate semialdehyde by the conversion of adipic acid to adipate semialdehyde in the presence of one or more polypeptides of the disclosure.

In addition, the polypeptides disclosed herein, and each of their respective distinct domains, can be used as building blocks in the rational design of proteins with improved carboxylic acid reductase catalytic activities.

Bioproducts

Bioproducts or bioderived products (e.g., the aldehydes and alcohols produced in accordance with the present disclosure) comprising biologically produced organic compounds, and in particular, the aldehydes and alcohols biologically produced using the biosynthetic pathway disclosed herein, have not been previously produced from renewable sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588, which is herein incorporated by reference). The ability to distinguish bioproducts from petroleum based organic compounds is beneficial in tracking these materials in commerce. For example, organic compounds or chemicals comprising both biologically based and petroleum based carbon isotope profiles may be distinguished from organic compounds and chemicals made only of petroleum based materials. Hence, the bioproducts herein can be followed or tracked in commerce on the basis of their unique carbon isotope profile. Bioproducts can be distinguished from petroleum based organic compounds by comparing the stable carbon isotope ratio ($^{13}C/^{12}C$) in each fuel. The ($^{13}C/^{12}C$) ratio in a given bioproduct is a consequence of the ($^{13}C/^{12}C$) ratio in atmospheric carbon dioxide at the time the carbon dioxide is fixed. It also reflects the precise metabolic pathway. Regional variations also occur. Petroleum, C3 plants (the broadleaf), C4 plants (the grasses), and marine carbonates all show significant differences in ($^{13}C/^{12}C$) and the corresponding delta$^{13}C$ values. Furthermore, lipid matter of C3 and C4 plants analyze differently than materials derived from the carbohydrate components of the same plants as a consequence of the metabolic pathway. Within the precision of measurement, $^{13}C$ shows large variations due to isotopic fractionation effects, the most significant of which for bioproducts is the photosynthetic mechanism. The major cause of differences in the carbon isotope ratio in plants is closely associated with differences in the pathway of photosynthetic carbon metabolism in the plants, particularly the reaction occurring during the primary carboxylation (i.e., the initial fixation of atmospheric $CO_2$). Two large classes of vegetation are those that incorporate the C3 (or Calvin-Benson) photosynthetic cycle and those that incorporate the C4 (or Hatch-Slack) photosynthetic cycle. In C3 plants, the primary $CO_2$ fixation or carboxylation reaction involves the enzyme ribulose-1,5-diphosphate carboxylase, and the first stable product is a 3-carbon compound. C3 plants, such as hardwoods and conifers, are dominant in the temperate climate zones. In C4 plants, an additional carboxylation reaction involving another enzyme, phosphoenol-pyruvate carboxylase, is the primary carboxylation reaction. The first stable carbon compound is a 4-carbon acid that is subsequently decarboxylated. The $CO_2$ thus released is refixed by the C3 cycle. Examples of C4 plants are tropical grasses, corn, and sugar cane. Both C4 and C3 plants exhibit a range of ($^{13}C/^{12}C$) isotopic ratios, but typical values are about −7 to about −13 per mil for C4 plants and about −19 to about −27 per mil for C3 plants (see, e.g., Stuiver et al., Radiocarbon 19:355 (1977)). Coal and petroleum fall generally in this latter range. The $^{13}C$ measurement scale was originally defined by a zero set by Pee Dee Belemnite (PDB) limestone, where values are given in parts per thousand deviations from this material. The "delta$^{13}C$" values are expressed in parts per thousand (per mil), abbreviated, ‰ o, and are calculated as follows:

$$\text{delta}^{13}C = [(^{13}C/^{12}C)_{sample} - (^{13}C/^{12}C)_{standard}]/(^{13}C/^{12}C)_{standard} \times 1000$$

Since the PDB reference material (RM) has been exhausted, a series of alternative RMs have been developed in cooperation with the IAEA, USGS, NIST, and other selected international isotope laboratories. Notations for the per mil deviations from PDB is delta13C. Measurements are made on $CO_2$ by high precision stable ratio mass spectrometry (IRMS) on molecular ions of masses 44, 45, and 46. The compositions described herein include bioproducts produced by any of the methods described herein, including, for example, aldehyde and alcohol products. Specifically, the bioproduct can have a delta$^{13}C$ of about −28 or greater, about −27 or greater, −20 or greater, −18 or greater, −15 or greater, −13 or greater, −10 or greater, or −8 or greater. For example, the bioproduct can have a delta$^{13}C$ of about −30 to about −15, about −27 to about −19, about −25 to about −21, about −15 to about −5, about −13 to about −7, or about −13 to about −10. In other instances, the bioproduct can have a delta$^{13}C$ of about −10, −11, −12, or −12.3. Bioproducts, including the bioproducts produced in accordance with the disclosure herein, can also be distinguished from petroleum based organic compounds by comparing the amount of 14C in each compound. Because 14C has a nuclear half-life of 5730 years, petroleum based fuels containing "older" carbon can be distinguished from bioproducts which contain "newer" carbon (see, e.g., Currie, "Source Apportionment of Atmospheric Particles", Characterization of Environmental Particles, J. Buffle and H. P. van Leeuwen, Eds., 1 of Vol. I of the IUPAC Environmental Analytical Chemistry Series (Lewis Publishers, Inc.) 3-74, (1992)).

The basic assumption in radiocarbon dating is that the constancy of 14C concentration in the atmosphere leads to the constancy of 14C in living organisms. However, because of atmospheric nuclear testing since 1950 and the burning of fossil fuel since 1850, 14C has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate 14C12C) of about $1.2 \times 10^{-12}$, with an approximate relaxation "half-life" of 7-10 years. (This latter half-life must not be taken literally; rather, one must use the detailed atmospheric nuclear input/decay function to trace the variation of atmospheric and biospheric 14C since the onset of the nuclear age.) It is this latter biospheric 14C time characteristic that holds out the promise of annual dating of recent biospheric carbon. 14C can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C. As used herein, fraction of modern carbon ($f_M$) has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the 14C/12C isotope ratio HOxI (referenced to AD 1950). This is roughly equivalent to decay-corrected pre-Industrial Revolution wood. For the current living biosphere (plant material), $f_M$ is approximately 1.1. This is roughly equivalent to decay-corrected pre-Industrial Revolution wood. For the current living biosphere (plant material), $f_M$ is approximately 1.1.

The compositions described herein include bioproducts that can have an $f_M$ 14 C of at least about 1. For example, the bioproduct of the disclosure can have an $f_M$ 14 C of at least about 1.01, an $f_M$ 14 C of about 1 to about 1.5, an $f_M$ 14 C of about 1.04 to about 1.18, or an $f_M$ 14 C of about 1.111 to about 1.124. Another measurement of 14C is known as the percent of modern carbon (pMC). For an archaeologist or geologist using 14C dates, AD 1950 equals "zero years old". This also represents 100 pMC. "Bomb carbon" in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a .sup.14C signature near 107.5 pMC. Petroleum based compounds will have a pMC value of zero. Combining fossil carbon with present day carbon will result in a dilution of the present day pMC content. By presuming 107.5 pMC represents the 14C content of present day biomass materials and 0 pMC represents the 14C content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning "100%" equal to 107.5 pMC and "0%" equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty aldehydes or alcohols as described herein can have a pMC of at least about 50, 60, 70, 75, 80, 85, 90, 95, 96, 97, 98, 99, or 100. In other instances, a bioproduct described herein can have a pMC of between about 50 and about 100; about 60 and about 100; about 70 and about 100; about 80 and about 100; about 85 and about 100; about 87 and about 98; or about 90 and about 95. In yet other instances, a bioproduct described herein can have a pMC of about 90, 91, 92, 93, 94, or 94.2.

Compositions

Some embodiments relate to compositions comprising one or more disclosed polypeptides or nucleotides, alone or in combination, including in combination with wild type CAR polypeptides. In some embodiments, the composition comprises one or more polypeptide with improved catalytic activity. In some embodiments, the composition comprises one or more polypeptide with improved increased specific activity in the catalysis the reduction of adipic acid and/or pimelic acid to aldehyde.

In some embodiments the composition may be composed of one or more disclosed polypeptides, from (1) commercial suppliers; (2) cloned genes expressing said polypeptides; (3) complex broth (such as that resulting from growth of a microbial strain or any other host cell in media, wherein the strains/host cells secrete the disclosed polypeptides into the media; (4) cell lysates of strains/host cells grown as in (3); and/or (5) any other host cell material expressing the disclosed polypeptide. Different disclosed polypeptides in a composition may be obtained from different sources.

In some embodiments, the composition comprises adipic acid and/or pimelic acid and one or more polypeptides described herein. In other embodiments, these compositions further comprise a wild-type CAR polypeptide.

All of the claims in the claim listing are herein incorporated by reference into the specification in their entireties as additional embodiments.

EXAMPLES

Example 1

Implementation of Targeted Mutagenesis of the CAR from *Segniliparus* rugosus

In earlier experimental work, the enzyme from *Segniliparus rugosus* (SrugCAR, SrCAR, or SrugCAR-wt) appeared to have the desired activity (reduction of a carboxylic acid to its respective aldehyde), although at an insufficient level for practical application. Therefore, SrugCAR was engineered towards improved catalytic reduction of pimelic acid and adipic acid to their respective aldehydes.

The expression of native, N-His and C-His tagged SrugCAR variants was optimized in *E. coli* BL21(DE3) and an assay for the detection of CAR activity adapted from M. Kalim Akhtara,b, Nicholas J. Turnerb, 1, and Patrik R. Jonesa, Carboxylic acid reductase is a versatile enzyme for the conversion of fatty acids into fuels and chemical commodities PNAS, Jan. 2, 2013, vol. 110, no. 1: 87. Briefly, cells were cultivated in ZYM-505 media supplemented with the relivant antibiotics, until an OD600 0.6-0.8 was reached. Protein expression was subsequently induced with 0.11 mM IPTG, and the cells were cultivated overnight at 30° C. Following a harvest, the cells were lysed in three cycles of freeze/thawing, and resuspendend in 50 mM Hepes pH 7.5, 2 mM MgCl2 with lysozyme and nuclease. To a 96 well plate 180 µl of 50 mM HEPES pH 7, 2 mM of the pimelic/adipic acid, MgCl2.6H2O (10 mM), ATP (1 mM) and NADPH (0.5 mM) was added to 20 µl of the cell free extract. Subsequently catalytic reaction was monitored spectrophotometrically at 25° C. by the cofactor conversion of NADPH to NADP+ at 340 nm.

Example 2

Design of a First Library Using Targeted Mutagenesis with Enzyme from *Segniliparus Rugosus*

A mutagenesis library was designed from structural and homology analysis. The model of SrugCAR was calculated by YASARA in order to be able to complement sequence based information. At the time this structural model was calculated, only eight X-ray similar structures were available for the model calculation showing low sequence identity for the respective domains (<55%). As there was no X-ray structure a CAR enzyme available the structural model could be used only for considering each domain individually.

The combined analysis of conserved sequence motifs and the domain structure models allowed the prediction of regions that comprise the putative active site(s) and surrounding areas/surfaces with substantial probability. These available sequence- and structural indications were used as preferred sites for degenerate primers for mutagenesis.

The identification of preferred sites for mutagenesis allowed the second step of the engineering work, namely design of a first library. Based on the conclusions of sequence and structure model evaluations as described above, engineering of SrugCAR was started by a broad screening of mutations spanning the whole enzyme. A total of 404 positions covering putative substrate binding site(s) and surrounding areas/surfaces within both large domains and the PP-site were chosen for mutagenesis. Positions with very high conservation throughout homologous sequences (>90% for the AMP/NAD(P) binding domain; >80% for the PP-site) were excluded to retain general enzyme function.

Amino acids of all chosen positions in SrugCAR library 1 represent the distribution at each position in homologous sequences. The basis for the determination of the distribution is a Position Specific Iterated BLAST, with four iterations and 1000 sequences. This generated >500 sequences that show a similar length and sequence identities around 50% at a minimum. Summary information for SrugCAR library 1 strategy is given in Table 3.

TABLE 3

Overview design of recombination libraries SrugCAR 1

| Sub-Library | Domain | Number of positions for Mutagenesis | Domain/site-coverage | Theor. Library size |
|---|---|---|---|---|
| 1-1 | Adenylating domain | 220 | 37% | 1,890 |
| 1-2 | PP-site | 57 | 81% | 619 |
| 1-3 | NAD(P) binding domain | 127 | 32% | 1,145 |

Example 3

Screening of a First Library for Higher Activity Towards Pimelic Acid/Adipic Acid with the CAR Enzyme from *Segniliparus Rugosus*

From 3,654 theoretical mutants of SrugCAR-1a total of 3,060 mutants were generated with degenerate primers representing the identified distribution at selection positions. In total (ATP/AMP domain: 1,140 mutants; PP-site: 540 mutants; NAD(P) binding domain: 1,080 mutants) were screened by applying the lysis and assay protocols optimized for SrugCAR-wt enzyme (Example 1). As a result, only mutants under standard assay conditions demonstrating >50% increase NADPH absorbance were identified in this primary screening. These were verified by applying a procedure that includes a normalization (using Coomassie stained polyacrylamide gels containing denatured protein, the density of which was obtained following separation) of SrugCAR on the protein level (i.e., band intensity upon a Coomassie stained SDS-gel) to eliminate any false positives that might occur due to a different expression level of the mutants compared to the wildtype. A set of 10 single mutants showed increased wildtype activities with pimelic and adipic acid and were further used for a recombination. These were: P369V, S284A, G380D, AND G619Y (ATP/AMP binding domain); K692R (PP-SITE); and A894G, A892G, P849G, A880V, and C781V (NAD(P) binding domain).

Example 4

Recombination Libraries with Enzyme from *Segniliparus Rugosus*

The beneficial single mutations identified in library SrugCAR-1 were now recombined aiming at a further increase in activity. In order to increase the probability of a successful recombination a set of amino acids should be allowed at each position which include the new, a few similar and the wildtype amino acid. However, a recombination of all positions and substitutions in one step would have resulted in a very large library of >73,000 mutants, which is difficult to manage in a reasonable screening set up. It was therefore decided to perform the recombination stepwise by combining the mutations of the different domains, each in combination with the PP-site resulting in two small libraries (SrugCAR-2-1 and SrugCAR-2-2) that can be screened completely (Table 4).

TABLE 4

Overview design of recombination libraries SrugCAR 2-1 and SrugCAR 2-2

| Domain | Single Mutation from Library 1 | Allowed mutations for recombination in library 2 | Recombination Libraries |
|---|---|---|---|
| Adenylate forming domain | P369V | VPGS | SrugCAR-2-1 |
|  | S284A | ASGT | 384 mutants |
|  | G380D | DGE |  |
|  | G619Y | YGFL |  |
| PP-Site | K692R | KR | SrugCAR-2-2 |
| NAD(P) binding domain | A894G | GAV | 384 mutants |
|  | A892G | GAVS |  |
|  | P849G | PG |  |
|  | A880V | VA |  |
|  | C781V | VCAS |  |

This time, the screening of the recombination libraries SrugCAR-2-1 and SrugCAR2-2 was done under optimized assay conditions. The improvements in the assay (increasing ATP concentration from 1 mM to 5 mM, increasing NADPH concentration from 0.5 mM to 2 mM and increasing the acid concentration from 2 to 20 mM) increased the sensitivity and accuracy of detection.

The following mutations from recombination libraries SrugCAR-2-1 and SrugCAR2 that generated improved activity are as follows:
SrugCAR-2-1
SrugCAR-31: S284G P369V G619Y
SrugCAR-51: E220K S284A P369S G380E K692R
SrugCAR-52: P369S G380E G619L
SrugCAR2-2:
SrugCAR-48: K692R P849G A892G A894V
SrugCAR-41: C781V A892G A894V
SrugCAR-54: K692R P849G A894G
SrugCAR-55: K492R The improvements of these seven mutants ranged from 130% up to 209% wt-activity for pimelic acid and 130% up to 176% wt-activity for adipic acid. $2^{nd}$ Round Combination Mutants:

The beneficial mutation sets identified for the AMP/PP-site (SrugCAR Library 2-1) and the NAD(P) binding domain/PP-site (SrugCAR Library 2-2) were now used for another recombination round in order to further increase the specific activity of SrugCAR. Each of the library SrugCAR-2-1 variant was recombined with each library SrugCAR2-2 mutant. This combination resulted in 9 multi-point improved mutants:
SrugCAR-50: S284G, P369V, G619Y, K692R, P849G, A892G, A894V
SrugCAR-56: S284G, P369V, G619Y C781V, A892G, A894V
SrugCAR-58: S284G, P369V, G619Y, K692R, P849G, A894G
SrugCAR-59: S284G, P369V, G619Y, K692R
SrugCAR-60: S284A, P369S, G380E, K692R, P849G, A892G, A894V
SrugCAR-61: S284A, P369S, G380E, C781V, A892G, A894V
SrugCAR-63: S284A, P369S, G380E, K692R, P849G, A894G
SrugCAR-65: P369S, G380E, G619L, K692R, P849G, A892G, A894V
SrugCAR-66: P369S, G380E, G619L, C781V, A892G, A894V
SrugCAR-69: P369S, G380E, G619L, K692R
(same as writing P369S G380E G619L K692R, i.e., without the commas separating each of the multiple mutations)

The resulting full length genes were then cloned into the expression vector and expressed under standard expression conditions (Example 1).

Example 5

Characterization of Specific Activity with Enzyme from *Segniliparus* Rugosus

These 9 recombination mutants were characterized towards their specific activity for pimelic acid and adipic acid by applying the optimised assay protocol (See Example 3). The resulting data show that recombinations over all domains implicate an additive improvement in some mutants SrugCAR-61, SrugCAR-65, SrugCAR-66, SrugCAR-69. According to these data, and under these conditions, SrugCAR-69 is the mutant showing the highest specific activity for pimelic acid and adipic acid. The specific activity of the best optimized mutant SrugCAR-69 with mutations P369S, G380E, G619L and K692R corresponds to 233% wt-activity for pimelic acid and 214% wt-activity for adipic acid.

These mutations affect primarily the AMP/adenylating domain. Only one of the four mutations (K692R) is in the PP-site.

Example 6

Search for New Carboxylic Acid Reductases from Biodiversity

Different approaches to identify new CAR enzymes active with adipic and pimelic acid from biodiversity were investigated. Database screening based on the domain architecture of CAR enzymes led to the identification of fragments for 7 novel putative CAR enzymes. Four of those genes were cloned into an expression vector and functionally analysed. Activity was obtained only with a gene from *S. rotundus* (SrotCAR, ADG99338). The newly identified SrotCAR was active with adipic and pimelic acid, which is just the second known wild type enzyme that shows significant activity with these two substrates. A preliminary comparison of both adipic and pimelic acid active enzymes resulted in sequence similarities of only 76% and no obvious sequence pattern which could explain this substrate specificity. However, a closer examination of the sequence probably together with a structure modelling could give further insights into substrate specificity and could give useful information for further engineering experiments. Analysis of the genomic context revealed striking similarities between the two enzymes with the desired activity, which may assist further database screenings. Therefore, one new active CAR enzyme with the desired activity was identified which could be used as a basis for improvement of the activity.

Example 7

Optimized SrotCAR Gene

For library generation, a very high (>60%) or very low GC-content (<40%) of the gene is problematic. The analysis of the SrotCAR gene showed that the native gene-sequence has a GC content of 68%. A detailed analysis showed several regions with a GC-content of over 80%. This can cause serious problems during library generation, when mutations are to be introduced in these specific areas.

Therefore, the gene sequence was optimized to avoid regions with extreme high GC-contents. Additionally, the codon-usage was adapted to the preferences of *E. coli*. The optimized gene sequence was ordered as a synthetic gene and cloned into c-LEcta's proprietary expression vector pLE1A17. *E. coli* BL21(DE3) cells, containing the PPTase-gene, were transformed with both constructs (SrotCAR_opt and SrotCAR_native gene).

The SrotCAR_biodiv (i.e., the native gene from biodiversity study of Example 6) (SEQ ID NO:5), SrotCAR_opt (SEQ ID NO:6), SrugCAR (SEQ ID NO:3) and SrugCAR_opt (SEQ ID NO:4) were expressed in shaking flasks and the expression levels of the CAR enzyme in the soluble fraction after cell-disruption were compared by SDS-PAGE. The optimized SrotCAR_opt gene thus showed an at least 4-fold higher expression-level compared to the native gene from biodiversity and also a ~50% higher soluble expression compared to the SrugCAR enzymes, as determined using Coomassie stained polyacrylamide gels containing denatured protein, the density of which was obtained following separation using a standard method.

Example 8

Transfer of the SrugCAR-69 Mutations to SrotCAR

The corresponding mutations of SrugCAR-69 variant (P369S-G380E-G619L-K692R) were transferred to the SrotCAR. After sequence-alignment of both enzymes the corresponding mutations in SrotCAR are P369S-G380E-Q623L-E696R, these mutations were generated and confirmed by sequence analysis.

The new SrotCAR-69 variant was expressed in shaking flask and its activity was compared to the SrotCAR template. The variant showed a specific activity improvement of 15-20%.

Example 9

Design and Screening of First Mutant Libraries with *Segniliparus rotundis* (SrotCAR)

The first SrotCAR mutant libraries were designed analogously to the first mutant libraries of the SrugCAR in the previous EXAMPLES. The homology model (FIG. 2) was generated utilising a number of structures including but not limited to 3NI2, 2D1S and 2D1T as scaffolds for the AMP-binding domain, 3EJE-E, 2VSQ-A and 1L0I-A as scaffolds for phosphopantetheine attachment site (PP-site) and 4DQV as a scaffold for the NAD-binding domain. Degenerate primers were used with in average 8.6 possible mutations per residue. The degenerate primers were designed to specifically include mutations calculated by c-LEcta's analysis with the aim to generate a high quality library with an optimized mutant to hit ratio. In total 3489 possible mutations at 404 positions:

AMP-Domain
- 1794 theoretical mutations at 220 different positions

PP-Domain
- 585 theoretical mutations at 57 different positions

NAD(P) Reductase domain
- 1110 theoretical mutations at 127 different positions

In total 4416 clones were screened. 77 of the most active hits were collected in a hit-plate, which was screened again towards adipic and pimelic acid using 4 replicates. All hit-variants were sequenced and compared to their activity. Several clusters or hot-spots (FIG. 2) were identified with multiple mutations in close proximity, e.g. between residues 331-338. Most of the very beneficial mutations are within one of these clusters. Some of these hot-spots encompass the following residues, relative to SEQ ID NO:2:

| Amino acid position | Active site region |
|---|---|
| 331-338 | ATP/AMP active site region 1a |
| 370-386 | ATP/AMP active site region 1b |
| 448-452 | ATP/AMP active site region 1c |
| 516-520 | ATP/AMP active site region 1d |
| 590-596 | ATP/AMP active site region 1e |
| 683-684 | PP binding region |
| 826-832 | NADP active site region 1a |
| 866-869 | NADP active site region 1b |

The most active single point mutants showed 60-100% higher activity compared to the SrugCAR_opt (E516F/V, L448E/V, M452I, I684V, V331M and E831I). The sequence analysis for W622 showed a mixture of both W and S at the position. It should be mentioned that nearly all selected hits proved to be more active compared to the WT (Z-factor >0). From 77 screening selected hits 71 different mutations (see FIG. 4) were identified. Those with a Z-factor >0 include S284I, V331L/M, M334G/V, L336F, H337D/I/V, E338N, T371F, L379V, L383T/V, G386A, L448E/V, M452I/L, F453A, V474R/G, V476L, N481D, V491L, A494V, K495V, L520T, E516F/V, G579E/V, L590V, R591G, P592A/G, E596G, D607S, E622W/S, D647G/S, I683Q, I684V, A709H, P711D, T780N/S, P826V, E831I, P832Y, Q866V, G869T, L893V, A902I, L1086A). Of these 28 variants showed a adipic or pimelic acid activity improvement over WT between one and two standard deviation: I684V, S284I, M452L, G869T H337I, M334V, G869T, P592G, K495V, I683Q, Q866V, K495V, L520T, G579E, L379V, V491L, D647S, P592G, T780S, V331L, M334G, P826V, D647G, D647S, H337V, L590V, R591G, E516V. An additional eight variants showed more than two standard deviations higher activity E516F, L448E, M452I, L448V, E622W/S, V331M, E831I, T371F for either or both acids.

Example 10

Second Generation Recombination of Beneficial Mutations with *Segniliparus rotundis* (SrotCAR)

After identification of the most interesting hot-spots for activity improvement, the mutations were recombined. Initially, two different approaches were chosen simultaneously:

Approach 1: Combination of the most active variants.
Approach 2: Complex recombination libraries using degenerate primers and mutating two, four and five positions simultaneously. As template, the L448E-variant was chosen.

Mutations at 331 and 516+L448E: 9 variants, 24 were screened

Mutations at 331, 516, 684, 831+L448E: 288 variants, 576 were screened

Mutations at 331, 371, 516, 684, 831+L448E: 2304 variants, 4608 were screened

By simultaneous mutation of several residues, possible cooperative/synergy might be observed, which otherwise would not be found by simple combination of the most active variants.

Several combinatorial variants were generated. The best combinations were:
L448E-M452I (ATP/AMP active site region 1 b)
E516F-L520T (ATP/AMP active site region 1d)
L448E-V331M (ATP/AMP active site region 1B+ATP/AMP active site region 1a)
L448E-E516F (ATP/AMP active site region 1 b+(ATP/AMP active site region 1d)
L448E-E622W (ATP/AMP active site region 1b+ATP/PP binding site linking region)

The complex recombination libraries were generated and screened as well. In total 5208 variants from the complex recombination libraries were screened. A triple mutant (V331M-L448E-E516V) and a quadruple mutant (V331M-L448E-E516V-E831D) were identified that suggested further improved, cooperative activity.

Example 11

Characterization of Final Hit-Variants
The following enzymes were expressed in shaking flasks being the final hit-variants:

| Enzyme | Mutations |
|---|---|
| SrotCAR_opt | |
| SrotCAR-02 | E516F |
| SrotCAR-03 | L448E |
| SrotCAR-04 | V331M-L448E-E516V |
| SrotCAR-05 | L448E-M452I |
| SrotCAR-06 | E516F-L520T |
| SrotCAR-07 | V331M-L448E |
| SrotCAR-08 = 03 | L448E |
| SrotCAR-09 | L448-E622W |
| SrotCAR-10 | V331M-L448E-E516V-E831D |

The expression levels of all variants were very similar and are still approximately 4-fold higher compared with the SrotCAR_biodiv gene and 50% higher compared to the SrugCAR and its variants.

For the specific activity measurements, the crude extract preparations were prepared and the activities towards pimelic- and adipic acid were measured. The enzyme amount was adjusted according to SDS-PAGE analysis of the expression level. The activity was compared to the SrotCAR wild-type.

The highest activity towards pimelic acid was shown by the double mutant SrotCAR-07 V331M-L448E, with nearly 2-fold increased activity compared to the template. This variant encompasses mutations in the ATP/AMP domain. The same variant also showed one of the highest activities using adipic acid, with 70% improvement compared to the template. Several variants showed similarly high activity improvements. The most active variant found in this engineering project was the SrotCAR-07 variant with V331M-L448E. It still shows ~50% higher expression in E. coli compared to the SrugCAR and its variants. According to this result, the specific activity of the SrotCAR-07 is approximately 50% higher compared to SrugCAR-69.

```
SEQ ID NO: 1: EFV11917|Native Segniliparas rugosus Amino Acid
Sequence
MGDGEERAKR FFQRIGELSA TDPQFAAAAP DPAVVEAVSD PSLSFTRYLD        50

TLMRGYAERP ALAHRVGAGY ETISYGELWA RVGAIAAAWQ ADGLAPGDFV       100

ATVGFTSPDY VAVDLAAARS GLVSVPLQAG ASLAQLVGIL EETEPKVLAA       150

SASSLEGAVA CALAAPSVQR LVVFDLRGPD ASESAADERR GALADAEEQL       200

ARAGRAVVVE TLADLAARGE ALPEAPLFEP AEGEDPLALL IYTSGSTGAP       250

KGAMYSQRLV SQLWGRTPVV PGMPNISLHY MPLSHSYGRA VLAGALSAGG       300

TAHFTANSDL STLFEDIALA RPTFLALVPR VCEMLFQESQ RGQDVAELRE       350

RVLGGRLLVA VCGSAPLSPE MRAFMEEVLG FPLLDGYGST EALGVMRNGI       400

IQRPPVIDYK LVDVPELGYR TTDKPYPRGE LCIRSTSLIS GYYKRPEITA       450

EVFDAQGYYK TGDVMAEIAP DHLVYVDRSK NVLKLSQGEF VAVAKLEAAY       500

GTSPYVKQIF VYGNSERSFL LAVVVPNAEV LGARDQEEAK PLIAASLQKI       550

AKEAGLQSYE VPRDFLIETE PFTTQNGLLS EVGKLLRPKL KARYGEALEA       600

RYDEIAHGQA DELRALRDGA GQRPVVETVV RAAVAISGSE GAEVGPEANF       650

ADLGGDSLSA LSLANLLHDV FEVEVPVRII IGPTASLAGI AKHIEAERAG       700

ASAPTAASVH GAGATRIRAS ELTLEKFLPE DLLAAAKGLP AADQVRTVLL       750

TGANGWLGRF LALEQLERLA RSGQDGGKLI CLVRGKDAAA ARRRIEETLG       800
```

-continued

```
TDPALAARFA ELAEGRLEVV PGDVGEPKFG LDDAAWDRLA EEVDVIVHPA         850

ALVNHVLPYH QLFGPNVVGT AEIIRLAITA KRKPVTYLST VAVAAGVEPS         900

SFEEDGDIRA VVPERPLGDG YANGYGNSKW AGEVLLREAH ELVGLPVAVF         950

RSDMILAHTR YTGQLNVPDQ FTRLVLSLLA TGIAPKSFYQ QGAAGERQRA        1000

HYDGIPVDFT AEAITTLGAE PSWFDGGAGF RSFDVFNPHH DGVGLDEFVD        1050

WLIEAGHPIS RIDDHKEWFA RFETAVRGLP EAQRQHSLLP LLRAYSFPHP        1100

PVDGSVYPTG KFQGAVKAAQ VGSDHDVPHL GKALIVKYAD DLKALGLL          1148
```

SEQ ID NO: 2: Codon Optimised *Segniliparus rotundus* CAR Amino Acid Sequence
```
MGSGADRAKL FFQKIEELTA ADPQFAAAVP DQEVVAAVSD PTLSFTRYLD          50

TLMRGYADRP ALAHRVGDGY ATISYGELWS RVGAIAAAWS ADGLEPGDFV         100

ATIGFTSPDY TALDLAATRS GLVSVPLQAG ASVAQLSAIL EETAPKVFAA         150

SAESLEGAVD CVLRTPSVQR LVIFDLRDDS PEHRAALAAA KAKLAQPQNP         200

EQARGPVAVE TLDELVARGA ALPEPPVFEP AEGEDPLALL IYTSGSTGTP         250

KGAMYSQRLV SRFWPRTPVV AQLPSISLHY MPLSHSYGRA VLCGTLAAGG         300

TAHFTAHSDL STLFEDIALA RPTFLALVPR VCEMLLHESR RARDLAELRE         350

RVLGERLLVA VCGSAPLAPE TRAFMEELLG FPLLDGYGST EALSLMRDGV         400

IQRPPVIDYK LVDVPELGYF TTDKPHPRGE LLIRSESLVS GYYKRPELTA         450

EMFDEQGYYK TGDVMAEIAP DRLVYVDRSK NVLKLSQGEF VAVAKLEAAF         500

GASPYVKQIF VYGNSERSFL LAVVVPNAEL VGRLDTVQAL AEVKPLIADS         550

LAAIAKESGL QSYEVPRDFI VETEPFTTGN GLLSEVGKLL RPKLKERYGE         600

RLEALYDQIA QGQADELRAL REQAGERPVI DTVRKAAAAV VGSSGADFRP         650

DANFADLGGD SLSALGFANL LQDVFGVETP VRIIIGPTAS LAGIAEHIER         700

ALGGRPGEAA PNSASVHGAG AEVIRASDLT LDKFLDAQAL EAAQSLPRPT         750

GSHRTVLLTG ANGWLGRFLA LEQLQRLEAT GGKLICLVRG KDAASARARV         800

EEALGTDPAL AARFAELAAD RLEVVPGDVG EPKFGLDDRT WDRLAGEVDA         850

VVHSGALVNH VLPYHQLFGS NVVGVAEIIR FAVASKLKPV AYLSTVAVAA         900

GADPAAFDED GDIREVVPQR PVDDSYANGY GNSKWAGEVL LREAHERTGL         950

PVRVFRSDMI LAHRQHTGQL NATDQFTRLI LSLLATGLAP KSFYQLDPQG        1000

RRQRAHYDGI PVDFTAEAIV ALAAEGNNGH RSYNVFNPHH DGVGLDEFVD        1050

WLIEAGHPIT RIEDHATWFA RFTTALRALP EKQRQLSLLP LAQVYSFPHP        1100

AVDGSPFRNA VFRADVQRAR IGKDHDIPHL TRELILKYAA DLAALGSL          1148
```

SEQ ID NO: 3: EFV11917|Native *Segniliparus rugosus* CAR Nucleotide Sequence

```
ATGGGCGACG GCGAAGAGCG GGCGAAGCGT TTCTTCCAGA GGATCGGGGA          50

GCTGAGCGCG ACGGACCCGC AGTTCGCGGC CGCCGCGCCG GACCCCGCCG         100

TGGTCGAGGC CGTGTCGGAC CCCTCGCTCT CGTTCACCCG CTACTTGGAC         150

ACGCTGATGC GCGGGTACGC CGAGCGCCCG GCGCTCGCCC ACCGGGTCGG         200

CGCGGGATAC GAGACGATCA GCTACGGGGA GCTGTGGGCG CGGGTCGGGG         250

CGATTGCGGC GGCGTGGCAG GCGGACGGCC TCGCGCCGGG CGACTTCGTC         300

GCCACGGTCG GTTTCACCAG CCCGGACTAC GTCGCCGTCG ACCTTGCGGC         350

CGCGAGGTCG GGGCTGGTGT CCGTGCCGTT GCAGGCGGGT GCTTCGCTCG         400

CCCAGCTCGT CGGGATCCTC GAGGAGACCG AGCCGAAGGT GCTCGCGGCG         450
```

```
                         -continued
AGCGCGAGCA GTCTCGAAGG GGCCGTTGCC TGCGCGCTGG CGGCCCCGAG          500

CGTGCAGCGG CTCGTCGTGT TCGACCTGCG CGGCCCGGAC GCTTCGGAGA          550

GCGCGGCGGA CGAGCGCCGA GGCGCCCTCG CCGATGCCGA GGAGCAGCTG          600

GCGCGGGCCG GGCGGGCCGT GGTCGTCGAG ACCCTCGCCG ACCTGGCGGC          650

CCGAGGCGAG GCGCTGCCGG AAGCCCCGCT GTTCGAGCCC GCCGAGGGCG          700

AAGACCCGCT GGCCCTCTTG ATCTACACGT CCGGCTCGAC CGGGGCCCCG          750

AAGGGGGCGA TGTACTCGCA GCGCCTGGTG TCCCAGCTCT GGGGGCGCAC          800

GCCGGTGGTG CCGGGGATGC CGAACATCTC GCTGCATTAC ATGCCGCTGA          850

GCCACTCCTA CGGGCGGGCG GTCCTCGCCG GGGCGCTCTC GGCGGCGGG           900

ACCGCCCACT TCACCGCGAA CAGCGACCTT TCCACCCTCT TCGAGGACAT          950

CGCGCTCGCC CGCCCCACCT TCCTCGCCCT GGTCCCCAGG GTCTGCGAGA         1000

TGCTGTTCCA GGAGAGCCAG CGCGGCCAGG ACGTCGCGGA GCTGCGCGAA         1050

CGGGTGCTCG GCGGTCGGCT GCTGGTCGCG GTGTGCGGCT CCGCCCCGCT         1100

GTCGCCGGAG ATGCGCGCGT TCATGGAGGA GGTGCTCGGC TTCCCGCTGC         1150

TCGACGGCTA CGGCTCGACC GAGGCGCTCG GCGTCATGCG CAACGGGATC         1200

ATCCAGCGCC CGCCGGTCAT CGACTACAAG CTGGTCGACG TGCCCGAGCT         1250

GGGCTATCGC ACCACTGACA AGCCCTACCC GAGGGGCGAG CTGTGCATCC         1300

GCTCGACGAG CCTGATCTCC GGCTACTACA AGCGCCCCGA GATCACAGCG         1350

GAGGTGTTCG ACGCGCAGGG CTACTACAAG ACCGGCGACG TGATGGCCGA         1400

GATCGCGCCG GACCACCTGG TGTACGTGGA CCGGAGCAAG AACGTCCTCA         1450

AACTCTCCCA AGGCGAGTTC GTCGCCGTCG CGAAGCTCGA AGCCGCGTAC         1500

GGCACGAGCC CGTACGTGAA GCAGATCTTC GTCTACGGCA ACAGCGAGCG         1550

CTCCTTCCTG CTCGCGGTCG TCGTGCCGAA CGCCGAAGTC CTCGGCGCGC         1600

GGGACCAGGA GGAGGCCAAG CCGCTCATCG CCGCCTCGCT GCAGAAGATC         1650

GCGAAAGAGG CTGGCCTGCA GTCTTACGAG GTCCCGCGCG ACTTCTTGAT         1700

CGAGACCGAG CCGTTCACCA CGCAGAACGG CCTGCTCTCC GAGGTCGGCA         1750

AGCTGCTGCG CCCGAAGCTC AAGGCCCGGT ACGGCGAGGC GCTGGAGGCG         1800

CGCTACGACG AGATCGCGCA CGGCCAGGCG GACGAGCTGC GCGCGCTGCG         1850

GGACGGCGCG GGACAGCGCC CGGTGGTCGA GACCGTCGTG CGGGCCGCCG         1900

TCGCGATCTC CGGCTCCGAG GGCGCGGAGG TCGGCCCTGA GGCGAACTTC         1950

GCCGACCTCG GCGGGACTC GCTCTCCGCG TTGAGCCTTG CGAACTTGCT          2000

GCACGACGTC TTCGAAGTCG AGGTGCCGGT GCGGATCATC ATCGGCCCGA         2050

CCGCCTCGCT CGCCGGGATC GCCAAGCACA TCGAGGCCGA GCGCGCCGGG         2100

GCGAGCGCCC CGACGGCGGC CTCCGTGCAC GGCGCGGGGG CGACGAGGAT         2150

CCGAGCGAGC GAGCTGACGC TGGAGAAATT CCTCCCTGAA GACCTGCTTG         2200

CCGCCGCGAA GGGCCTTCCG GCCGCCGACC AGGTCCGCAC GGTGCTCTTG         2250

ACGGGCGCGA ACGGCTGGCT CGGGCGTTTC CTCGCGTTGG AACAGCTCGA         2300

ACGGCTCGCC CGATCGGGGC AGGACGGCGG GAAGCTGATC TGCCTGGTCC         2350

GGGGAAAGA CGCGGCTGCG GCGCGCAGGC GGATCGAAGA AACGCTCGGC          2400

ACGGACCCGG CCCTGGCCGC CAGGTTCGCC GAACTTGCCG AGGGGCGGTT         2450
```

```
GGAAGTGGTC CCGGGGGACG TGGGCGAGCC GAAGTTCGGC TTGGACGACG       2500

CGGCATGGGA CCGGCTGGCC GAGGAGGTGG ACGTCATCGT CCACCCGGCG       2550

GCCCTTGTGA ACCACGTTCT GCCGTACCAC CAGCTGTTCG GGCCGAACGT       2600

GGTCGGCACG GCGGAGATCA TCCGGCTCGC GATCACCGCC AAGCGCAAGC       2650

CGGTCACCTA CCTCTCCACG GTGGCGGTCG CGGCGGGCGT GGAGCCCTCC       2700

TCCTTCGAGG AGGACGGCGA CATCCGGGCC GTGGTCCCCG AACGGCCCTT       2750

GGGCGATGGG TACGCGAACG GCTACGGCAA CAGCAAATGG GCGGGGGAGG       2800

TGCTGCTGCG CGAAGCGCAC GAGCTTGTGG GCCTGCCGGT GGCGGTGTTC       2850

CGCTCGGACA TGATCCTCGC GCACACCCGG TACACCGGAC AGCTCAACGT       2900

CCCCGACCAG TTCACCAGGC TCGTCCTGAG CCTTTTGGCC ACCGGGATCG       2950

CGCCCAAGTC CTTCTACCAG CAGGGCGCGG CGGGCGAACG CCAGCGGGCG       3000

CATTACGACG GCATCCCCGT GGACTTCACC GCCGAGGCCA TCACCACGCT       3050

CGGCGCGGAG CCGAGCTGGT TCGACGGCGG CGCGGGGTTC CGCAGCTTCG       3100

ACGTGTTCAA CCCGCACCAC GACGGGGTGG GCTTGGACGA GTTCGTGGAC       3150

TGGCTCATCG AGGCCGGGCA TCCGATCTCC AGGATCGACG ACCACAAGGA       3200

ATGGTTCGCC CGGTTCGAGA CCGCCGTGCG CGGCCTGCCC GAAGCGCAGC       3250

GCCAGCATTC CCTGCTGCCG CTGTTGCGCG CCTACTCGTT CCCGCATCCG       3300

CCCGTGGACG GCAGTGTCTA TCCGACCGGG AAGTTCCAGG GCGCGGTCAA       3350

AGCCGCGCAG GTGGGCTCCG ACCACGACGT GCCGCATCTC GGCAAGGCGC       3400

TGATCGTGAA ATACGCGGAC GACCTGAAGG CTCTCGGACT CCTCTGA          3447

SEQ ID NO: 4: Condon Optimised Segniliparus rugosus CAR Nucleotide
Sequence
ATGGGCGACG CGAAGAACG TGCGAAACGC TTTTTCCAAC GTATCGGTGA          50

ACTGTCTGCG ACCGATCCGC AGTTTGCAGC AGCAGCTCCG GACCCGGCTG        100

TGGTTGAAGC CGTGAGTGAT CCGTCACTGT CGTTCACCCG CTATCTGGAT        150

ACGCTGATGC GCGGCTACGC AGAACGTCCG GCTCTGGCAC ATCGTGTGGG        200

TGCAGGTTAT GAAACCATCA GCTACGGTGA ACTGTGGGCC CGTGTTGGTG        250

CAATTGCAGC AGCATGGCAG GCTGATGGTC TGGCACCGGG TGACTTCGTC        300

GCAACCGTGG GTTTTACGTC CCCGGATTAT GTTGCAGTCG ACCTGGCTGC        350

AGCACGTTCA GGTCTGGTGT CGGTTCCGCT GCAAGCCGGT GCATCACTGG        400

CCCAGCTGGT TGGCATTCTG GAAGAAACCG AACCGAAAGT CCTGGCAGCT        450

TCGGCAAGCT CTCTGGAAGG CGCTGTTGCG TGCGCACTGG CAGCACCGAG        500

CGTCCAGCGC CTGGTCGTGT TTGATCTGCG TGGTCCGGAC GCGAGCGAAT        550

CTGCAGCTGA TGAACGTCGC GGCGCACTGG CTGACGCAGA AGAACAGCTG        600

GCCCGCGCAG GTCGTGCAGT TGTCGTGGAA ACCCTGGCTG ATCTGGCAGC        650

GCGTGGCGAA GCCCTGCCGG AAGCACCGCT GTTTGAACCG GCGGAAGGTG        700

AAGATCCGCT GGCCCTGCTG ATCTATACCA GTGGCTCCAC GGGTGCTCCG        750

AAAGGTGCGA TGTACAGTCA ACGCCTGGTG TCCCAGCTGT GGGGTCGTAC        800

CCCGGTTGTC CCGGGTATGC CGAACATTTC CCTGCATTAT ATGCCGCTGT        850

CACACTCGTA CGGTCGTGCG GTTCTGGCTG GTGCACTGTC AGCCGGCGGT       900

ACCGCACATT TCACGGCTAA TAGCGATCTG TCTACCCTGT TTGAAGACAT        950

CGCACTGGCA CGTCCGACGT TCCTGGCACT GGTTCCGCGT GTCTGCGAAA       1000
```

-continued

```
TGCTGTTTCA GGAATCGCAA CGCGGCCAGG ATGTGGCCGA ACTGCGCGAA      1050

CGTGTTCTGG GCGGTCGTCT GCTGGTCGCA GTGTGTGGTA GCGCTCCGCT      1100

GTCTCCGGAA ATGCGCGCGT TCATGGAAGA AGTGCTGGGC TTTCCGCTGC      1150

TGGATGGCTA TGGTTCAACC GAAGCCCTGG GTGTGATGCG CAACGGCATT      1200

ATCCAGCGTC CGCCGGTTAT TGATTACAAA CTGGTTGACG TCCCGGAACT      1250

GGGTTATCGT ACCACGGATA AGCCGTACCC GCGCGGCGAA CTGTGTATCC      1300

GTAGCACGTC TCTGATTAGC GGTTATTACA AACGTCCGGA AATCACCGCG      1350

GAAGTGTTTG ACGCCCAGGG TTATTACAAG ACGGGCGATG TTATGGCGGA      1400

AATTGCCCCG GATCATCTGG TGTATGTTGA CCGTAGCAAA AATGTGCTGA      1450

AGCTGTCTCA AGGCGAATTC GTCGCTGTGG CGAAACTGGA AGCAGCTTAT      1500

GGTACCTCTC CGTACGTGAA GCAGATCTTC GTTTATGGCA ACAGTGAACG      1550

CTCCTTTCTG CTGGCAGTGG TTGTCCCGAA TGCAGAAGTG CTGGGTGCTC      1600

GTGATCAGGA AGAAGCGAAA CCGCTGATCG CGGCCTCCCT GCAAAAAATT      1650

GCAAAGGAAG CTGGCCTGCA GAGCTATGAA GTGCCGCGCG ATTTCCTGAT      1700

TGAAACCGAA CCGTTTACCA CGCAGAACGG TCTGCTGTCT GAAGTTGGCA      1750

AGCTGCTGCG CCCGAAACTG AAGGCGCGTT ATGGCGAAGC GCTGGAAGCC      1800

CGTTACGATG AAATCGCGCA TGGTCAAGCC GATGAACTGC GTGCGCTGCG      1850

TGACGGTGCC GGTCAGCGTC CGGTGGTTGA AACCGTCGTG CGTGCAGCTG      1900

TGGCAATTAG TGGCTCCGAA GGTGCTGAAG TTGGTCCGGA AGCAAACTTT      1950

GCTGATCTGG GCGGTGACTC ACTGTCGGCA CTGTCGCTGG CTAATCTGCT      2000

GCACGATGTG TTCGAAGTTG AAGTCCCGGT GCGCATTATC ATTGGTCCGA      2050

CCGCGAGCCT GGCAGGTATC GCAAAACATA TTGAAGCGGA ACGTGCAGGT      2100

GCATCAGCTC CGACGGCAGC CTCGGTTCAC GGCGCAGGTG CAACCCGTAT      2150

TCGTGCATCC GAACTGACGC TGGAAAAAAT TCTGCCGGAA GACCTGCTGG      2200

CAGCTGCAAA GGGTCTGCCG GCAGCAGATC AAGTGCGTAC CGTTCTGCTG      2250

ACGGGTGCAA ATGGTTGGCT GGGCCGTTTC CTGGCCCTGG AACAACTGGA      2300

ACGCCTGGCA CGTAGTGGTC AGGACGGCGG TAAACTGATC TGCCTGGTGC      2350

GTGGCAAGGA TGCTGCAGCA GCACGTCGCC GTATTGAAGA AACCCTGGGT      2400

ACGGATCCGG CACTGGCTGC ACGTTTTGCT GAACTGGCGG AAGGTCGTCT      2450

GGAAGTTGTC CCGGGTGATG TGGGCGAACC GAAATTCGGC CTGGATGACG      2500

CCGCATGGGA TCGTCTGGCG GAAGAAGTTG ACGTCATTGT GCATCCGGCT      2550

GCGCTGGTCA ACCATGTGCT GCCGTATCAC CAGCTGTTTG GTCCGAATGT      2600

GGTTGGCACC GCGGAAATCA TTCGCCTGGC CATCACGGCA AAACGTAAAC      2650

CGGTGACCTA CCTGAGCACG GTTGCCGTCG CCGCAGGTGT TGAACCGAGT      2700

TCCTTCGAAG AAGATGGCGA CATTCGTGCA GTCGTGCCGG AACGTCCGCT      2750

GGGTGATGGT TATGCAAACG GCTACGGTAA TTCTAAATGG GCAGGTGAAG      2800

TGCTGCTGCG TGAAGCACAT GAACTGGTTG GCCTGCCGGT GGCAGTTTTT      2850

CGCAGTGACA TGATCCTGGC GCACACCCGT TATACGGGTC AACTGAACGT      2900

CCCGGATCAG TTTACCCGTC TGGTGCTGTC GCTGCTGGCA ACGGGTATTG      2950

CACCGAAATC TTTTTATCAG CAAGGTGCTG CAGGTGAACG TCAGCGTGCA      3000
```

-continued

```
CACTACGATG GCATCCCGGT GGACTTTACC GCAGAAGCTA TTACCACGCT    3050

GGGTGCCGAA CCGTCTTGGT TCGATGGCGG TGCAGGCTTT CGCAGTTTCG    3100

ATGTTTTTAA TCCGCATCAC GACGGCGTTG GTCTGGATGA ATTTGTCGAC    3150

TGGCTGATCG AAGCGGGTCA TCCGATCAGT CGTATTGATG ACCACAAAGA    3200

ATGGTTCGCA CGCTTTGAAA CCGCTGTGCG TGGCCTGCCG GAAGCACAGC    3250

GCCAACATAG TCTGCTGCCG CTGCTGCGTG CCTATTCCTT TCCGCACCCG    3300

CCGGTTGATG GTTCAGTCTA CCCGACGGGT AAATTCCAAG GTGCAGTCAA    3350

GGCAGCACAA GTGGGTAGCG ATCATGACGT CCCGCACCTG GGCAAAGCCC    3400

TGATTGTGAA GTATGCGGAT GACCTGAAAG CCCTGGGCCT GCTGTAA       3447
```

SEQ ID NO: 5: ADG99338 Native *Segniliparus rotundus* CAR Nucleotide Sequence

```
ATGGGCAGCG GCGCGGATCG GGCGAAGCTT TTTTTCCAAA AGATCGAGGA      50

GCTGACCGCG GCGGACCCCC AGTTCGCGGC GGCAGTGCCG GACCAGGAGG     100

TCGTGGCGGC GGTTTCTGAT CCCACGCTCT CGTTCACCCG CTACCTGGAC     150

ACGCTCATGC GGGGCTATGC GGACCGCCCC GCCCTCGCCC ACCGGGTCGG     200

CGATGGTTAC GCGACGATCA GCTACGGGGA GCTGTGGTCG CGCGTCGGGG     250

CGATCGCGGC GGCTTGGAGC GCGGATGGCC TCGAACCCGG AGATTTCGTC     300

GCCACCATCG GCTTCACGAG CCCCGATTAC ACCGCTCTCG ACTTGGCGGC     350

GACCAGGTCC GGCCTGGTGT CCGTGCCGTT GCAGGCAGGA GCTTCTGTCG     400

CGCAGCTGTC CGCGATCCTC GAAGAAACCG CGCCGAAGGT CTTCGCGGCG     450

AGCGCCGAAA GCCTCGAAGG GGCGGTGGAC TGCGTGCTGC GGACCCCGAG     500

CGTCCAGCGG CTCGTCATCT TCGATCTGCG GGACGACTCG CCCGAGCACC     550

GGGCGGCCCT CGCGGCGGCG AAAGCCAAGC TCGCGCAGCC CCAGAATCCC     600

GAACAGGCGC GAGGACCCGT GGCCGTGGAG ACGCTCGACG AGCTGGTCGC     650

GCGCGGCGCG GCGCTGCCCG AGCCGCCTGT GTTCGAACCC GCCGAGGGCG     700

AGGACCCGTT GGCCCTGTTG ATTTACACGT CAGGCTCGAC CGGCACCCCC     750

AAGGGGGCCA TGTACTCGCA GCGCCTCGTG TCCCGGTTCT GGCCCAGGAC     800

CCCGGTCGTC GCCCAACTCC CGAGTATTTC GCTGCACTAC ATGCCCCTCA     850

GCCACTCCTA TGGCCGGGCG GTCCTGTGCG GGACGCTCGC CGCTGGCGGG     900

ACCGCGCATT TCACCGCCCA CAGCGACCTT TCGACCCTCT TCGAGGACAT     950

CGCGCTCGCC CGCCCCACGT TCCTCGCGCT GGTTCCCAGG GTGTGCGAGA    1000

TGCTGTTGCA CGAGAGCCGT CGGGCGCGGG ACCTCGCTGA ACTGCGCGAA    1050

CGGGTGCTCG GCGAGCGGCT GTTGGTGGCG GTGTGCGGCT CCGCGCCGTT    1100

GGCGCCCGAG ACGCGGGCCT TCATGGAGGA GCTGCTCGGC TTCCCCTTGC    1150

TCGACGGTTA CGGTTCGACC GAGGCGCTGT CGCTCATGCG GGACGGGGTG    1200

ATCCAACGCC CGCCGGTCAT CGATTACAAA CTGGTCGACG TGCCCGAGCT    1250

CGGCTATTTC ACCACCGACA AGCCGCACCC CCGGGGGGAG CTGCTCATCC    1300

GCTCCGAAAG CCTCGTCTCC GGCTACTACA AGCGCCCCGA GCTGACAGCG    1350

GAGATGTTCG ACGAGCAGGG CTACTACAAA ACCGGCGACG TGATGGCCGA    1400

GATCGCGCCG GACCGCCTCG TCTACGTGGA CCGGAGCAAA AACGTCCTCA    1450

AGCTCTCCCA GGGCGAGTTC GTCGCGGTCG CGAAGCTGGA GGCCGCCTTC    1500

GGCGCGAGCC CGTATGTCAA GCAGATCTTC GTCTACGGCA ACAGCGAGCG    1550
```

```
CTCGTTCCTG CTCGCGGTGG TCGTGCCGAA CGCCGAACTC GTCGGCCGGC       1600

TCGACACCGT CCAGGCGCTG GCCGAAGTGA AGCCGCTCAT CGCGGACTCG       1650

CTCGCCGCGA TCGCCAAAGA GTCTGGCCTG CAGTCCTATG AGGTCCCGCG       1700

CGACTTCATC GTCGAGACCG AGCCGTTCAC CACCGGCAAC GGACTGCTCT       1750

CCGAAGTCGG CAAGCTTTTG CGCCCGAAGC TCAAGGAGCG GTACGGCGAA       1800

CGGCTCGAAG CGCTCTACGA CCAGATCGCG CAGGGCCAGG CGGATGAACT       1850

GCGCGCGTTG CGCGAGCAGG CGGGGGAGCG CCCGGTGATC GACACAGTCC       1900

GCAAAGCCGC CGCAGCAGTG GTGGGCTCCA GCGGCGCGGA CTTTCGGCCT       1950

GACGCGAATT TCGCCGACCT CGGCGGAGAC TCGCTCTCCG CGTTGGGTTT       2000

CGCGAACCTT TTGCAGGACG TGTTCGGGGT CGAGACGCCC GTTCGGATCA       2050

TCATCGGCCC GACCGCGTCG CTCGCCGGGA TCGCCGAGCA CATCGAGCGC       2100

GCGTTGGGCG GTCGCCCGGG CGAGGCGGCG CCGAACTCGG CCTCGGTGCA       2150

CGGCGCCGGG GCCGAGGTGA TCCGCGCGAG CGATCTGACG TTGGACAAAT       2200

TCCTGGACGC GCAGGCGCTC GAAGCTGCGC AGAGCCTGCC CAGGCCCACC       2250

GGCTCCCATC GCACCGTGCT GCTCACCGGC GCGAACGGCT GGCTCGGACG       2300

GTTTCTCGCG CTCGAGCAGC TTCAGCGGCT CGAAGCCACC GGCGGGAAGC       2350

TGATCTGCTT GGTCAGGGGC AAAGACGCGG CCTCGGCGCG CGCGCGGGTC       2400

GAAGAAGCGC TCGGCACCGA CCCGGCGCTC GCGGCCCGGT CGCCGAACT        2450

CGCCGCAGAC CGGCTCGAAG TGGTTCCCGG CGACGTCGGC GAGCCGAAGT       2500

TCGGCCTGGA CGATCGCACC TGGGACCGGC TTGCGGGCGA GGTGGACGCT       2550

GTGGTGCACT CCGGCGCCTT GGTGAACCAC GTTCTGCCGT ACCACCAGCT       2600

CTTCGGGTCG AACGTGGTCG GCGTCGCCGA GATCATCCGC TTCGCCGTCG       2650

CCTCGAAGCT CAAACCTGTC GCCTACCTCT CCACCGTCGC CGTCGCGGCA       2700

GGCGCCGACC CCGCCGCATT CGACGAGGAC GGCGACATCC GCGAAGTCGT       2750

GCCCCAACGA CCTGTCGACG ACAGCTACGC CAACGGCTAC GGCAACAGCA       2800

AATGGGCCGG CGAGGTCCTG CTCCGCGAAG CGCACGAGCG CACCGGCCTG       2850

CCTGTGCGCG TCTTCCGCTC CGACATGATC CTCGCCCACC GGCAACACAC       2900

CGGCCAGCTC AACGCCACCG ACCAATTCAC ACGGCTCATC CTCAGCCTCC       2950

TCGCCACCGG CCTCGCCCCG AAGTCCTTCT ACCAACTCGA CCCCCAAGGC       3000

AGACGGCAAC GGGCCCACTA CGACGGCATT CCCGTGGACT TCACCGCCGA       3050

GGCCATCGTC GCCCTCGCCG CCGAAGGCAA CAACGGCCAC CGCAGCTACA       3100

ACGTCTTCAA CCCCCACCAC GACGGCGTCG GCTTGGACGA GTTCGTCGAC       3150

TGGCTCATCG AAGCCGGACA TCCCATCACC CGCATCGAAG ACCACGCGAC       3200

ATGGTTCGCC CGTTTCACGA CCGCGCTCCG CGCCCTCCCG GAAAAACAAC       3250

GCCAGCTGTC GCTGTTGCCG CTTGCGCAGG TGTACTCGTT CCCGCATCCG       3300

GCTGTTGACG GCTCGCCGTT CCGGAACGCC GTGTTCCGGG CCGATGTGCA       3350

GAGGGCGAGG ATCGGCAAGG ACCACGATAT TCCGCATCTG ACGCGGGAGC       3400

TGATCCTGAA ATACGCCGCC GACCTGGCAG CGCTCGGCTT GTTGTAG         3447

SEQ ID NO: 6: Codon Optimised SegnMpaws rotundus CAR Nucleotide
Sequence
ATGGGCTCTG GAGCGGATCG CGCGAAGCTG TTCTTTCAGA AAATTGAAGA        50
```

-continued

```
ACTGACTGCA GCGGACCCAC AATTTGCAGC AGCCGTGCCC GATCAGGAAG          100

TGGTGGCCGC CGTAAGCGAC CCAACTCTGT CGTTTACCCG TTATCTCGAT          150

ACCCTGATGC GTGGCTATGC GGATCGTCCG GCACTGGCGC ATCGCGTTGG          200

TGACGGTTAT GCGACCATCT CTTACGGGGA ACTGTGGTCA CGCGTTGGAG          250

CGATTGCTGC AGCCTGGAGC GCGGATGGAC TGGAGCCGGG TGATTTTGTG          300

GCTACGATTG GGTTCACTAG TCCGGACTAT ACCGCCCTGG ATCTGGCAGC          350

GACCCGTTCC GGGCTCGTTA GCGTTCCGCT GCAGGCGGGC GCTAGTGTGG          400

CGCAGCTGTC GGCGATCCTG GAGGAAACAG CCCCTAAAGT TTTCGCAGCG          450

AGCGCCGAAA GCCTGGAAGG TGCTGTGGAT TGCGTTTTGC GCACCCCGAG          500

TGTGCAGCGC CTGGTCATTT TCGACTTACG GGATGATAGC CCTGAGCATC          550

GCGCTGCCTT AGCGGCTGCA AAAGCGAAAC TTGCTCAGCC GCAGAATCCC          600

GAACAGGCCC GCGGGCCGGT AGCGGTAGAG ACACTGGATG AACTGGTTGC          650

TCGTGGTGCG GCACTTCCGG AACCTCCTGT CTTTGAACCA GCGGAAGGTG          700

AAGATCCGCT GGCCCTCCTG ATCTACACCA GCGGTTCCAC CGGCACGCCG          750

AAAGGGGCAA TGTACTCGCA GCGCCTTGTA TCTCGCTTCT GGCCCCGCAC          800

GCCGGTCGTT GCGCAGCTGC CATCCATCTC ACTTCACTAC ATGCCGCTTA          850

GCCACAGCTA TGGCCGTGCC GTGCTGTGTG GCACCCTGGC GGCTGGTGGT          900

ACAGCGCACT TTACGGCTCA TAGCGATCTG TCCACGCTGT TTGAAGATAT          950

TGCCCTCGCA CGCCCGACGT TTCTGGCACT GGTCCCGCGT GTCTGCGAAA         1000

TGCTGCTCCA CGAGTCGCGC CGCGCGCGTG ACTTAGCAGA ACTGCGCGAA         1050

CGGGTTTTGG GTGAACGCCT GCTCGTGGCG GTTTGTGGTA GTGCGCCTCT         1100

TGCGCCAGAA ACCCGCGCGT TTATGGAAGA GCTGCTGGGC TTTCCACTGC         1150

TGGATGGCTA TGGCTCAACC GAAGCGTTGA GCCTGATGCG CGATGGCGTG         1200

ATTCAGCGTC CTCCGGTAAT TGACTACAAA TTGGTGGACG TCCCGGAACT         1250

GGGTTACTTT ACCACCGATA AACCGCATCC CCGTGGCGAA CTGTTGATTC         1300

GCTCTGAATC TCTTGTAAGC GGTTACTATA AACGTCCAGA ATTGACAGCG         1350

GAGATGTTCG ATGAGCAAGG TTACTACAAG ACCGGCGATG TAATGGCCGA         1400

AATTGCCCCG GACCGCCTGG TCTACGTTGA CCGCTCCAAG AACGTCCTGA         1450

AACTGTCGCA AGGGGAATTT GTTGCCGTGG CAAAATTGGA GGCCGCATTC         1500

GGCGCAAGCC CGTATGTCAA GCAGATTTTC GTCTATGGTA ACAGTGAACG         1550

CTCTTTTCTG CTTGCAGTAG TCGTACCAAA CGCCGAATTA GTGGGCCGTC         1600

TTGACACAGT TCAAGCCCTG GCCGAAGTCA AACCCTTAAT CGCAGATAGT         1650

TTAGCGGCTA TTGCGAAAGA AAGCGGCTTG CAATCCTATG AAGTCCCGCG         1700

CGACTTTATC GTTGAAACCG AGCCGTTTAC GACGGGCAAT GGCCTGCTTT         1750

CTGAAGTTGG CAAACTCCTG CGGCCCAAAC TCAAGGAACG TTACGGTGAG         1800

CGCCTGGAGG CGCTGTACGA TCAGATTGCA CAGGGCCAAG CTGACGAGTT         1850

GCGTGCATTG CGTGAACAGG CGGGCGAACG CCCAGTGATC GATACGGTGC         1900

GCAAAGCCGC TGCCGCGGTG GTGGGGTCAT CAGGGGCCGA TTTTCGCCCA         1950

GATGCTAATT TCGCAGATCT GGGAGGTGAT AGCCTGTCAG CGCTGGGGTT         2000

CGCCAATTTA CTGCAAGATG TGTTCGGCGT TGAAACTCCG GTCCGGATCA         2050

TTATTGGACC TACTGCGAGT CTGGCGGGCA TTGCCGAACA TATCGAACGC         2100
```

-continued

GCTTTAGGCG GTCGCCCTGG CGAAGCGGCA CCAAATTCGG CAAGTGTGCA 2150

TGGCGCGGGT GCAGAAGTAA TCCGCGCATC TGACCTGACG TTAGACAAAT 2200

TCTTGGACGC TCAAGCCTTA GAAGCCGCGC AGTCGTTACC ACGTCCGACA 2250

GGCAGCCATC GGACGGTCCT GTTGACTGGA GCGAATGGAT GGTTAGGGCG 2300

CTTCCTGGCG CTCGAGCAGT TGCAGCGCTT AGAAGCCACG GGCGGAAAAC 2350

TGATCTGCTT AGTGCGCGGT AAAGACGCAG CGTCAGCGCG TGCACGCGTG 2400

GAGGAAGCGC TGGGCACCGA TCCCGCATTA GCAGCGCGCT TTGCCGAGCT 2450

GGCCGCAGAT CGTCTGGAAG TTGTTCCGGG TGACGTGGGC GAACCGAAGT 2500

TCGGTCTGGA CGATCGCACG TGGGATCGGC TGGCTGGTGA GGTAGATGCG 2550

GTAGTCCATT CTGGCGCGCT GGTTAACCAC GTTTTGCCCT ATCACCAGCT 2600

GTTCGGCAGT AACGTGGTGG GCGTGGCAGA AATCATCCGT TTCGCTGTGG 2650

CCTCTAAACT TAAACCGGTG GCCTATCTCT CCACTGTTGC TGTGGCTGCG 2700

GGCGCCGATC CTGCCGCGTT TGATGAAGAT GGTGACATTC GGGAGGTAGT 2750

GCCGCAACGC CCGGTCGATG ACTCGTATGC CAACGGCTAT GGCAACAGCA 2800

AGTGGGCGGG TGAGGTGCTG TTACGCGAAG CACACGAACG TACCGGGCTG 2850

CCGGTGCGTG TCTTTCGCAG TGACATGATT CTGGCCCATC GCCAACACAC 2900

CGGCCAGCTC AATGCGACCG ACCAGTTTAC CCGTCTGATT CTGTCCTTAC 2950

TGGCTACTGG TTTGGCTCCA AAATCGTTCT ATCAGTTAGA TCCGCAAGGT 3000

CGTCGCCAGC GTGCACATTA CGACGGTATT CCGGTCGATT TTACGGCTGA 3050

GGCGATCGTT GCCCTTGCCG CCGAGGGAAA TAATGGGCAC CGTTCCTATA 3100

ACGTCTTTAA CCCGCACCAT GATGGGGTTG GGCTGGACGA GTTTGTGGAT 3150

TGGCTGATCG AAGCCGGTCA TCCGATTACC CGCATTGAGG ATCACGCCAC 3200

ATGGTTCGCC CGTTTTACCA CTGCGCTGCG GGCGCTTCCT GAGAAACAAC 3250

GCCAGTTGTC GTTGCTCCCT CTGGCTCAGG TGTATAGCTT TCCCCATCCG 3300

GCGGTTGATG GATCCCCGTT CCGTAACGCA GTATTTCGTG CGGACGTGCA 3350

ACGTGCGCGT ATTGGTAAAG ATCATGATAT TCCGCATCTC ACCCGTGAAC 3400

TGATCCTGAA ATATGCTGCC GATCTGGCCG CTCTCGGCTC ACTTTAA 3447

SEQ ID NO: 7: Condon Optimised *Segniliparus rugosus* CAR Amino Acid Sequence

MGDGEERAKR FFQRIGELSA TDPQFAAAAP DPAVVEAVSD PSLSFTRYLD 50

TLMRGYAERP ALAHRVGAGY ETISYGELWA RVGAIAAAWQ ADGLAPGDFV 100

ATVGFTSPDY VAVDLAAARS GLVSVPLQAG ASLAQLVGIL EETEPKVLAA 150

SASSLEGAVA CALAAPSVQR LVVFDLRGPD ASESAADERR GALADAEEQL 200

ARAGRAVVVE TLADLAARGE ALPEAPLFEP AEGEDPLALL IYTSGSTGAP 250

KGAMYSQRLV SQLWGRTPVV PGMPNISLHY MPLSHSYGRA VLAGALSAGG 300

TAHFTANSDL STLFEDIALA RPTFLALVPR VCEMLFQESQ RGQDVAELRE 350

RVLGGRLLVA VCGSAPLSPE MRAFMEEVLG FPLLDGYGST EALGVMRNGI 400

IQRPPVIDYK LVDVPELGYR TTDKPYPRGE LCIRSTSLIS GYYKRPEITA 450

EVFDAQGYYK TGDVMAEIAP DHLVYVDRSK NVLKLSQGEF VAVAKLEAAY 500

GTSPYVKQIF VYGNSERSFL LAVVVPNAEV LGARDQEEAK PLIAASLQKI 550

AKEAGLQSYE VPRDFLIETE PFTTQNGLLS EVGKLLRPKL KARYGEALEA 600

```
RYDEIAHGQA DELRALRDGA GQRPVVETVV RAAVAISGSE GAEVGPEANF          650
ADLGGDSLSA LSLANLLHDV FEVEVPVRII IGPTASLAGI AKHIEAERAG          700
ASAPTAASVH GAGATRIRAS ELTLEKFLPE DLLAAAKGLP AADQVRTVLL          750
TGANGWLGRF LALEQLERLA RSGQDGGKLI CLVRGKDAAA ARRRIEETLG          800
TDPALAARFA ELAEGRLEVV PGDVGEPKFG LDDAAWDRLA EEVDVIVHPA          850
ALVNHVLPYH QLFGPNVVGT AEIIRLAITA KRKPVTYLST VAVAAGVEPS          900
SFEEDGDIRA VVPERPLGDG YANGYGNSKW AGEVLLREAH ELVGLPVAVF          950
RSDMILAHTR YTGQLNVPDQ FTRLVLSLLA TGIAPKSFYQ QGAAGERQRA         1000
HYDGIPVDFT AEAITTLGAE PSWFDGGAGF RSFDVFNPHH DGVGLDEFVD         1050
WLIEAGHPIS RIDDHKEWFA RFETAVRGLP EAQRQHSLLP LLRAYSFPHP         1100
PVDGSVYPTG KFQGAVKAAQ VGSDHDVPHL GKALIVKYAD DLKALGLL          1148
```

SEQ ID NO: 8: ADG99338 Native *Segniliparus rotundus* CAR Amino Acid
Sequence
```
MGSGADRAKL FFQKIEELTA ADPQFAAAVP DQEVVAAVSD PTLSFTRYLD           50
TLMRGYADRP ALAHRVGDGY ATISYGELWS RVGAIAAAWS ADGLEPGDFV          100
ATIGFTSPDY TALDLAATRS GLVSVPLQAG ASVAQLSAIL EETAPKVFAA          150
SAESLEGAVD CVLRTPSVQR LVIFDLRDDS PEHRAALAAA KAKLAQPQNP          200
EQARGPVAVE TLDELVARGA ALPEPPVFEP AEGEDPLALL IYTSGSTGTP          250
KGAMYSQRLV SRFWPRTPVV AQLPSISLHY MPLSHSYGRA VLCGTLAAGG          300
TAHFTAHSDL STLFEDIALA RPTFLALVPR VCEMLLHESR RARDLAELRE          350
RVLGERLLVA VCGSAPLAPE TRAFMEELLG FPLLDGYGST EALSLMRDGV          400
IQRPPVIDYK LVDVPELGYF TTDKPHPRGE LLIRSESLVS GYYKRPELTA          450
EMFDEQGYYK TGDVMAEIAP DRLVYVDRSK NVLKLSQGEF VAVAKLEAAF          500
GASPYVKQIF VYGNSERSFL LAVVVPNAEL VGRLDTVQAL AEVKPLIADS          550
LAAIAKESGL QSYEVPRDFI VETEPFTTGN GLLSEVGKLL RPKLKERYGE          600
RLEALYDQIA QGQADELRAL REQAGERPVI DTVRKAAAAV VGSSGADFRP          650
DANFADLGGD SLSALGFANL LQDVFGVETP VRIIIGPTAS LAGIAEHIER          700
ALGGRPGEAA PNSASVHGAG AEVIRASDLT LDKFLDAQAL EAAQSLPRPT          750
GSHRTVLLTG ANGWLGRFLA LEQLQRLEAT GGKLICLVRG KDAASARARV          800
EEALGTDPAL AARFAELAAD RLEVVPGDVG EPKFGLDDRT WDRLAGEVDA          850
VVHSGALVNH VLPYHQLFGS NVVGVAEIIR FAVASKLKPV AYLSTVAVAA          900
GADPAAFDED GDIREVVPQR PVDDSYANGY GNSKWAGEVL LREAHERTGL          950
PVRVFRSDMI LAHRQHTGQL NATDQFTRLI LSLLATGLAP KSFYQLDPQG         1000
RRQRAHYDGI PVDFTAEAIV ALAAEGNNGH RSYNVFNPHH DGVGLDEFVD         1050
WLIEAGHPIT RIEDHATWFA RFTTALRALP EKQRQLSLLP LAQVYSFPHP         1100
AVDGSPFRNA VFRADVQRAR IGKDHDIPHL TRELILKYAA DLAALGLL          1148
```

SEQ ID NO: 9: Condon Optimised *Segniliparus rugosus* CAR-69 Nucleotide
Sequence
```
ATGGGCGACG GCGAAGAACG TGCGAAACGC TTTTTCCAAC GTATCGGTGA           50
ACTGTCTGCG ACCGATCCGC AGTTTGCAGC AGCAGCTCCG GACCCGGCTG          100
TGGTTGAAGC CGTGAGTGAT CCGTCACTGT CGTTCACCCG CTATCTGGAT          150
ACGCTGATGC GCGGCTACGC AGAACGTCCG GCTCTGGCAC ATCGTGTGGG          200
TGCAGGTTAT GAAACCATCA GCTACGGTGA ACTGTGGGCC CGTGTTGGTG          250
```

```
CAATTGCAGC AGCATGGCAG GCTGATGGTC TGGCACCGGG TGACTTCGTC      300

GCAACCGTGG GTTTTACGTC CCCGGATTAT GTTGCAGTCG ACCTGGCTGC      350

AGCACGTTCA GGTCTGGTGT CGGTTCCGCT GCAAGCCGGT GCATCACTGG      400

CCCAGCTGGT TGGCATTCTG GAAGAAACCG AACCGAAAGT CCTGGCAGCT      450

TCGGCAAGCT CTCTGGAAGG CGCTGTTGCG TGCGCACTGG CAGCACCGAG      500

CGTCCAGCGC CTGGTCGTGT TTGATCTGCG TGGTCCGGAC GCGAGCGAAT      550

CTGCAGCTGA TGAACGTCGC GGCGCACTGG CTGACGCAGA AGAACAGCTG      600

GCCCGCGCAG GTCGTGCAGT TGTCGTGGAA ACCCTGGCTG ATCTGGCAGC      650

GCGTGGCGAA GCCCTGCCGG AAGCACCGCT GTTTGAACCG GCGGAAGGTG      700

AAGATCCGCT GGCCCTGCTG ATCTATACCA GTGGCTCCAC GGGTGCTCCG      750

AAAGGTGCGA TGTACAGTCA ACGCCTGGTG TCCCAGCTGT GGGGTCGTAC      800

CCCGGTTGTC CCGGGTATGC CGAACATTTC CCTGCATTAT ATGCCGCTGT      850

CACACTCGTA CGGTCGTGCG GTTCTGGCTG GTGCACTGTC AGCCGGCGGT      900

ACCGCACATT TCACGGCTAA TAGCGATCTG TCTACCCTGT TTGAAGACAT      950

CGCACTGGCA CGTCCGACGT TCCTGGCACT GGTTCCGCGT GTCTGCGAAA     1000

TGCTGTTTCA GGAATCGCAA CGCGGCCAGG ATGTGGCCGA ACTGCGCGAA     1050

CGTGTTCTGG GCGGTCGTCT GCTGGTCGCA GTGTGTGGTA GCGCTCCGCT     1100

GTCTTCTGAA ATGCGCGCGT TCATGGAAGA AGTGCTGGAA TTTCCGCTGC     1150

TGGATGGCTA TGGTTCAACC GAAGCCCTGG GTGTGATGCG CAACGGCATT     1200

ATCCAGCGTC CGCCGGTTAT TGATTACAAA CTGGTTGACG TCCCGGAACT     1250

GGGTTATCGT ACCACGGATA AGCCGTACCC GCGCGGCGAA CTGTGTATCC     1300

GTAGCACGTC TCTGATTAGC GGTTATTACA AACGTCCGGA AATCACCGCG     1350

GAAGTGTTTG ACGCCCAGGG TTATTACAAG ACGGGCGATG TTATGGCGGA     1400

AATTGCCCCG GATCATCTGG TGTATGTTGA CCGTAGCAAA AATGTGCTGA     1450

AGCTGTCTCA AGGCGAATTC GTCGCTGTGG CGAAACTGGA AGCAGCTTAT     1500

GGTACCTCTC CGTACGTGAA GCAGATCTTC GTTTATGGCA ACAGTGAACG     1550

CTCCTTTCTG CTGGCAGTGG TTGTCCCGAA TGCAGAAGTG CTGGGTGCTC     1600

GTGATCAGGA AGAAGCGAAA CCGCTGATCG CGGCCTCCCT GCAAAAAATT     1650

GCAAAGGAAG CTGGCCTGCA GAGCTATGAA GTGCCGCGCG ATTTCCTGAT     1700

TGAAACCGAA CCGTTTACCA CGCAGAACGG TCTGCTGTCT GAAGTTGGCA     1750

AGCTGCTGCG CCCGAAACTG AAGGCGCGTT ATGGCGAAGC GCTGGAAGCC     1800

CGTTACGATG AAATCGCGCA TGGTCAAGCC GATGAACTGC GTGCGCTGCG     1850

TGACCTGGCC GGTCAGCGTC CGGTGGTTGA AACCGTCGTG CGTGCAGCTG     1900

TGGCAATTAG TGGCTCCGAA GGTGCTGAAG TTGGTCCGGA AGCAAACTTT     1950

GCTGATCTGG GCGGTGACTC ACTGTCGGCA CTGTCGCTGG CTAATCTGCT     2000

GCACGATGTG TTCGAAGTTG AAGTCCCGGT GCGCATTATC ATTGGTCCGA     2050

CCGCGAGCCT GGCAGGTATC GCACGTCATA TTGAAGCGGA ACGTGCAGGT     2100

GCATCAGCTC CGACGGCAGC CTCGGTTCAC GGCGCAGGTG CAACCCGTAT     2150

TCGTGCATCC GAACTGACGC TGGAAAAAAT TCTGCCGGAA GACCTGCTGG     2200

CAGCTGCAAA GGGTCTGCCG GCAGCAGATC AAGTGCGTAC CGTTCTGCTG     2250
```

-continued

```
ACGGGTGCAA ATGGTTGGCT GGGCCGTTTC CTGGCCCTGG AACAACTGGA 2300

ACGCCTGGCA CGTAGTGGTC AGGACGGCGG TAAACTGATC TGCCTGGTGC 2350

GTGGCAAGGA TGCTGCAGCA GCACGTCGCC GTATTGAAGA AACCCTGGGT 2400

ACGGATCCGG CACTGGCTGC ACGTTTTGCT GAACTGGCGG AAGGTCGTCT 2450

GGAAGTTGTC CCGGGTGATG TGGGCGAACC GAAATTCGGC CTGGATGACG 2500

CCGCATGGGA TCGTCTGGCG GAAGAAGTTG ACGTCATTGT GCATCCGGCT 2550

GCGCTGGTCA ACCATGTGCT GCCGTATCAC CAGCTGTTTG GTCCGAATGT 2600

GGTTGGCACC GCGGAAATCA TTCGCCTGGC CATCACGGCA AAACGTAAAC 2650

CGGTGACCTA CCTGAGCACG GTTGCCGTCG CCGCAGGTGT TGAACCGAGT 2700

TCCTTCGAAG AAGATGGCGA CATTCGTGCA GTCGTGCCGG AACGTCCGCT 2750

GGGTGATGGT TATGCAAACG GCTACGGTAA TTCTAAATGG GCAGGTGAAG 2800

TGCTGCTGCG TGAAGCACAT GAACTGGTTG GCCTGCCGGT GGCAGTTTTT 2850

CGCAGTGACA TGATCCTGGC GCACACCCGT TATACGGGTC AACTGAACGT 2900

CCCGGATCAG TTTACCCGTC TGGTGCTGTC GCTGCTGGCA ACGGGTATTG 2950

CACCGAAATC TTTTTATCAG CAAGGTGCTG CAGGTGAACG TCAGCGTGCA 3000

CACTACGATG GCATCCCGGT GGACTTTACC GCAGAAGCTA TTACCACGCT 3050

GGGTGCCGAA CCGTCTTGGT TCGATGGCGG TGCAGGCTTT CGCAGTTTCG 3100

ATGTTTTTAA TCCGCATCAC GACGGCGTTG GTCTGGATGA ATTTGTCGAC 3150

TGGCTGATCG AAGCGGGTCA TCCGATCAGT CGTATTGATG ACCACAAAGA 3200

ATGGTTCGCA CGCTTTGAAA CCGCTGTGCG TGGCCTGCCG GAAGCACAGC 3250

GCCAACATAG TCTGCTGCCG CTGCTGCGTG CCTATTCCTT TCCGCACCCG 3300

CCGGTTGATG GTTCAGTCTA CCCGACGGGT AAATTCCAAG GTGCAGTCAA 3350

GGCAGCACAA GTGGGTAGCG ATCATGACGT CCCGCACCTG GGCAAAGCCC 3400

TGATTGTGAA GTATGCGGAT GACCTGAAAG CCCTGGGCCT GCTGTAA 3447
```

SEQ ID NO: 10: Condon Optimised *Segniliparus rugosus* CAR-69 Amino Acid Sequence

```
MGDGEERAKR FFQRIGELSA TDPQFAAAAP DPAVVEAVSD PSLSFTRYLD 50

TLMRGYAERP ALAHRVGAGY ETISYGELWA RVGAIAAAWQ ADGLAPGDFV 100

ATVGFTSPDY VAVDLAAARS GLVSVPLQAG ASLAQLVGIL EETEPKVLAA 150

SASSLEGAVA CALAAPSVQR LVVFDLRGPD ASESAADERR GALADAEEQL 200

ARAGRAVVVE TLADLAARGE ALPEAPLFEP AEGEDPLALL IYTSGSTGAP 250

KGAMYSQRLV SQLWGRTPVV PGMPNISLHY MPLSHSYGRA VLAGALSAGG 300

TAHFTANSDL STLFEDIALA RPTFLALVPR VCEMLFQESQ RGQDVAELRE 350

RVLGGRLLVA VCGSAPLSSE MRAFMEEVLE FPLLDGYGST EALGVMRNGI 400

IQRPPVIDYK LVDVPELGYR TTDKPYPRGE LCIRSTSLIS GYYKRPEITA 450

EVFDAQGYYK TGDVMAEIAP DHLVYVDRSK NVLKLSQGEF VAVAKLEAAY 500

GTSPYVKQIF VYGNSERSFL LAVVVPNAEV LGARDQEEAK PLIAASLQKI 550

AKEAGLQSYE VPRDFLIETE PFTTQNGLLS EVGKLLRPKL KARYGEALEA 600

RYDEIAHGQA DELRALRDLA GQRPVVETVV RAAVAISGSE GAEVGPEANF 650

ADLGGDSLSA LSLANLLHDV FEVEVPVRII IGPTASLAGI ARHIEAERAG 700

ASAPTAASVH GAGATRIRAS ELTLEKFLPE DLLAAAKGLP AADQVRTVLL 750

TGANGWLGRF LALEQLERLA RSGQDGGKLI CLVRGKDAAA ARRRIEETLG 800
```

-continued

```
TDPALAARFA ELAEGRLEVV PGDVGEPKFG LDDAAWDRLA EEVDVIVHPA        850

ALVNHVLPYH QLFGPNVVGT AEIIRLAITA KRKPVTYLST VAVAAGVEPS        900

SFEEDGDIRA VVPERPLGDG YANGYGNSKW AGEVLLREAH ELVGLPVAVF        950

RSDMILAHTR YTGQLNVPDQ FTRLVLSLLA TGIAPKSFYQ QGAAGERQRA       1000

HYDGIPVDFT AEAITTLGAE PSWFDGGAGF RSFDVFNPHH DGVGLDEFVD       1050

WLIEAGHPIS RIDDHKEWFA RFETAVRGLP EAQRQHSLLP LLRAYSFPHP       1100

PVDGSVYPTG KFQGAVKAAQ VGSDHDVPHL GKALIVKYAD DLKALGLL         1148
```

SEQ ID NO: 11: Condon Optimised Segniliparusrotundus CARV331M + L448E Nucleotide Sequence

```
ATGGGCTCTG GAGCGGATCG CGCGAAGCTG TTCTTTCAGA AAATTGAAGA          50

ACTGACTGCA GCGGACCCAC AATTTGCAGC AGCCGTGCCC GATCAGGAAG         100

TGGTGGCCGC CGTAAGCGAC CCAACTCTGT CGTTTACCCG TTATCTCGAT         150

ACCCTGATGC GTGGCTATGC GGATCGTCCG GCACTGGCGC ATCGCGTTGG         200

TGACGGTTAT GCGACCATCT CTTACGGGGA ACTGTGGTCA CGCGTTGGAG         250

CGATTGCTGC AGCCTGGAGC GCGGATGGAC TGGAGCCGGG TGATTTTGTG         300

GCTACGATTG GGTTCACTAG TCCGGACTAT ACCGCCCTGG ATCTGGCAGC         350

GACCCGTTCC GGGCTCGTTA GCGTTCCGCT GCAGGCGGGC GCTAGTGTGG         400

CGCAGCTGTC GGCGATCCTG GAGGAAACAG CCCCTAAAGT TTTCGCAGCG         450

AGCGCCGAAA GCCTGGAAGG TGCTGTGGAT TGCGTTTTGC GCACCCCGAG         500

TGTGCAGCGC CTGGTCATTT TCGACTTACG GGATGATAGC CCTGAGCATC         550

GCGCTGCCTT AGCGGCTGCA AAAGCGAAAC TTGCTCAGCC GCAGAATCCC         600

GAACAGGCCC GCGGGCCGGT AGCGGTAGAG ACACTGGATG AACTGGTTGC         650

TCGTGGTGCG GCACTTCCGG AACCTCCTGT CTTTGAACCA GCGGAAGGTG         700

AAGATCCGCT GGCCCTCCTG ATCTACACCA GCGGTTCCAC CGGCACGCCG         750

AAAGGGGCAA TGTACTCGCA GCGCCTTGTA TCTCGCTTCT GGCCCCGCAC         800

GCCGGTCGTT GCGCAGCTGC CATCCATCTC ACTTCACTAC ATGCCGCTTA         850

GCCACAGCTA TGGCCGTGCC GTGCTGTGTG GCACCCTGGC GGCTGGTGGT         900

ACAGCGCACT TTACGGCTCA TAGCGATCTG TCCACGCTGT TTGAAGATAT         950

TGCCCTCGCA CGCCCGACGT TTCTGGCACT GGTCCCGCGT ATGTGCGAAA        1000

TGCTGCTCCA CGAGTCGCGC CGCGCGCGTG ACTTAGCAGA ACTGCGCGAA        1050

CGGGTTTTGG GTGAACGCCT GCTCGTGGCG GTTTGTGGTA GTGCGCCTCT        1100

TGCGCCAGAA ACCCGCGCGT TTATGGAAGA GCTGCTGGGC TTTCCACTGC        1150

TGGATGGCTA TGGCTCAACC GAAGCGTTGA GCCTGATGCG CGATGGCGTG        1200

ATTCAGCGTC CTCCGGTAAT TGACTACAAA TTGGTGGACG TCCCGGAACT        1250

GGGTTACTTT ACCACCGATA AACCGCATCC CCGTGGCGAA CTGTTGATTC        1300

GCTCTGAATC TCTTGTAAGC GGTTACTATA AACGTCCAGA AGAAACAGCG        1350

GAGATGTTCG ATGAGCAAGG TTACTACAAG ACCGGCGATG TAATGGCCGA        1400

AATTGCCCCG GACCGCCTGG TCTACGTTGA CCGCTCCAAG AACGTCCTGA        1450

AACTGTCGCA AGGGGAATTT GTTGCCGTGG CAAAATTGGA GGCCGCATTC        1500

GGCGCAAGCC CGTATGTCAA GCAGATTTTC GTCTATGGTA ACAGTGAACG        1550

CTCTTTTCTG CTTGCAGTAG TCGTACCAAA CGCCGAATTA GTGGGCCGTC        1600
```

-continued

```
TTGACACAGT TCAAGCCCTG GCCGAAGTCA AACCCTTAAT CGCAGATAGT    1650
TTAGCGGCTA TTGCGAAAGA AAGCGGCTTG CAATCCTATG AAGTCCCGCG    1700
CGACTTTATC GTTGAAACCG AGCCGTTTAC GACGGGCAAT GGCCTGCTTT    1750
CTGAAGTTGG CAAACTCCTG CGGCCCAAAC TCAAGGAACG TTACGGTGAG    1800
CGCCTGGAGG CGCTGTACGA TCAGATTGCA CAGGGCCAAG CTGACGAGTT    1850
GCGTGCATTG CGTGAACAGG CGGGCGAACG CCCAGTGATC GATACGGTGC    1900
GCAAAGCCGC TGCCGCGGTG GTGGGGTCAT CAGGGGCCGA TTTTCGCCCA    1950
GATGCTAATT TCGCAGATCT GGGAGGTGAT AGCCTGTCAG CGCTGGGGTT    2000
CGCCAATTTA CTGCAAGATG TGTTCGGCGT TGAAACTCCG GTCCGGATCA    2050
TTATTGGACC TACTGCGAGT CTGGCGGGCA TTGCCGAACA TATCGAACGC    2100
GCTTTAGGCG GTCGCCCTGG CGAAGCGGCA CCAAATTCGG CAAGTGTGCA    2150
TGGCGCGGGT GCAGAAGTAA TCCGCGCATC TGACCTGACG TTAGACAAAT    2200
TCTTGGACGC TCAAGCCTTA GAAGCCGCGC AGTCGTTACC ACGTCCGACA    2250
GGCAGCCATC GGACGGTCCT GTTGACTGGA GCGAATGGAT GGTTAGGGCG    2300
CTTCCTGGCG CTCGAGCAGT TGCAGCGCTT AGAAGCCACG GGCGGAAAAC    2350
TGATCTGCTT AGTGCGCGGT AAAGACGCAG CGTCAGCGCG TGCACGCGTG    2400
GAGGAAGCGC TGGGCACCGA TCCCGCATTA GCAGCGCGCT TTGCCGAGCT    2450
GGCCGCAGAT CGTCTGGAAG TTGTTCCGGG TGACGTGGGC GAACCGAAGT    2500
TCGGTCTGGA CGATCGCACG TGGGATCGGC TGGCTGGTGA GGTAGATGCG    2550
GTAGTCCATT CTGGCGCGCT GGTTAACCAC GTTTTGCCCT ATCACCAGCT    2600
GTTCGGCAGT AACGTGGTGG GCGTGGCAGA AATCATCCGT TTCGCTGTGG    2650
CCTCTAAACT TAAACCGGTG GCCTATCTCT CCACTGTTGC TGTGGCTGCG    2700
GGCGCCGATC CTGCCGCGTT TGATGAAGAT GGTGACATTC GGGAGGTAGT    2750
GCCGCAACGC CCGGTCGATG ACTCGTATGC CAACGGCTAT GGCAACAGCA    2800
AGTGGGCGGG TGAGGTGCTG TTACGCGAAG CACACGAACG TACCGGGCTG    2850
CCGGTGCGTG TCTTTCGCAG TGACATGATT CTGGCCCATC GCCAACACAC    2900
CGGCCAGCTC AATGCGACCG ACCAGTTTAC CCGTCTGATT CTGTCCTTAC    2950
TGGCTACTGG TTTGGCTCCA AAATCGTTCT ATCAGTTAGA TCCGCAAGGT    3000
CGTCGCCAGC GTGCACATTA CGACGGTATT CCGGTCGATT TTACGGCTGA    3050
GGCGATCGTT GCCCTTGCCG CCGAGGGAAA TAATGGGCAC CGTTCCTATA    3100
ACGTCTTTAA CCCGCACCAT GATGGGGTTG GGCTGGACGA GTTTGTGGAT    3150
TGGCTGATCG AAGCCGGTCA TCCGATTACC CGCATTGAGG ATCACGCCAC    3200
ATGGTTCGCC CGTTTTACCA CTGCGCTGCG GGCGCTTCCT GAGAAACAAC    3250
GCCAGTTGTC GTTGCTCCCT CTGGCTCAGG TGTATAGCTT TCCCCATCCG    3300
GCGGTTGATG GATCCCCGTT CCGTAACGCA GTATTTCGTG CGGACGTGCA    3350
ACGTGCGCGT ATTGGTAAAG ATCATGATAT TCCGCATCTC ACCCGTGAAC    3400
TGATCCTGAA ATATGCTGCC GATCTGGCCG CTCTCGGCTC ACTTTAA       3447
```

SEQ ID NO: 12: Condon Optimised Segniliparusrotundus CARV331M + L448E Amino Acid sequence

```
MGSGADRAKL FFQKIEELTA ADPQFAAAVP DQEVVAAVSD PTLSFTRYLD     50
TLMRGYADRP ALAHRVGDGY ATISYGELWS RVGAIAAAWS ADGLEPGDFV    100
ATIGFTSPDY TALDLAATRS GLVSVPLQAG ASVAQLSAIL EETAPKVFAA    150
```

```
-continued

SAESLEGAVD CVLRTPSVQR LVIFDLRDDS PEHRAALAAA KAKLAQPQNP         200

EQARGPVAVE TLDELVARGA ALPEPPVFEP AEGEDPLALL IYTSGSTGTP         250

KGAMYSQRLV SRFWPRTPVV AQLPSISLHY MPLSHSYGRA VLCGTLAAGG         300

TAHFTAHSDL STLFEDIALA RPTFLALVPR MCEMLLHESR RARDLAELRE         350

RVLGERLLVA VCGSAPLAPE TRAFMEELLG FPLLDGYGST EALSLMRDGV         400

IQRPPVIDYK LVDVPELGYF TTDKPHPRGE LLIRSESLVS GYYKRPEETA         450

EMFDEQGYYK TGDVMAEIAP DRLVYVDRSK NVLKLSQGEF VAVAKLEAAF         500

GASPYVKQIF VYGNSERSFL LAVVVPNAEL VGRLDTVQAL AEVKPLIADS         550

LAAIAKESGL QSYEVPRDFI VETEPFTTGN GLLSEVGKLL RPKLKERYGE         600

RLEALYDQIA QGQADELRAL REQAGERPVI DTVRKAAAAV VGSSGADFRP         650

DANFADLGGD SLSALGFANL LQDVFGVETP VRIIIGPTAS LAGIAEHIER         700

ALGGRPGEAA PNSASVHGAG AEVIRASDLT LDKFLDAQAL EAAQSLPRPT         750

GSHRTVLLTG ANGWLGRFLA LEQLQRLEAT GGKLICLVRG KDAASARARV         800

EEALGTDPAL AARFAELAAD RLEVVPGDVG EPKFGLDDRT WDRLAGEVDA         850

VVHSGALVNH VLPYHQLFGS NVVGVAEIIR FAVASKLKPV AYLSTVAVAA         900

GADPAAFDED GDIREVVPQR PVDDSYANGY GNSKWAGEVL LREAHERTGL         950

PVRVFRSDMI LAHRQHTGQL NATDQFTRLI LSLLATGLAP KSFYQLDPQG        1000

RRQRAHYDGI PVDFTAEAIV ALAAEGNNGH RSYNVFNPHH DGVGLDEFVD        1050

WLIEAGHPIT RIEDHATWFA RFTTALRALP EKQRQLSLLP LAQVYSFPHP        1100

AVDGSPFRNA VFRADVQRAR IGKDHDIPHL TRELILKYAA DLAALGSL         1148
```

We claim:

1. A polypeptide having at least 95% sequence identity to the amino acid sequence of SEQ ID NO: 1, wherein the polypeptide comprises at least one mutation selected from the group consisting of: P369S/G/V, S284A/G/T, G380D/E, G619Y/F/L, K692R, A894G/V, A892V/S, P849 G, A880V and C781V/A/S and wherein the polypeptide has carboxylic acid reductase activity.

2. The polypeptide of claim 1, wherein the polypeptide comprises the following mutations:
P369S G380E G619L K692R;
S284G P369V G619Y;
E220K S284A P369S G380E K692R;
P369S G380E G619L;
K692R P849G A892G A894V;
C781V A892G A894V;
K692R P849G A894G;
S284G P369V G619Y K692R P849G A892G A894V;
S284G P369V G619Y C781V A892G A894V;
S284G P369V G619Y K692R P849G A894G;
S284G P369V G619Y K692R;
S284A P369S G380E K692R P849G A892G A894V;
S284A P369S G380E C781V A892G A894V;
S284A P369S G380E K692R P849G A894G;
P369S G380E G619L K692R P849G A892G A894V; or
P369S G380E G619L C781V A892G A894V.

3. The polypeptide of claim 1, wherein the polypeptide has at least 99% sequence identity to SEQ ID NO: 1.

4. A composition comprising the polypeptide of claim 1.

* * * * *